US007625565B2

(12) United States Patent
Zhabilov et al.

(10) Patent No.: US 7,625,565 B2
(45) Date of Patent: Dec. 1, 2009

(54) ANTIVIRAL COMPOSITIONS COMPRISING LYSINE-RICH HISTONE FRACTIONS PREPARED BY PEPSIN TREATMENT OF THYMIC CELL NUCLEI

(75) Inventors: Harry P. Zhabilov, San Marino, CA (US); Jordanka Zhabilov, legal representative, San Marino, CA (US); Harry H. Zhabilov, San Marino, CA (US)

(73) Assignee: Viral Genetics, Inc., San Marino, CA (US)

( * ) Notice: Subject to any disclaimer, the term of this patent is extended or adjusted under 35 U.S.C. 154(b) by 402 days.

(21) Appl. No.: 10/336,512

(22) Filed: Jan. 3, 2003

(65) Prior Publication Data

US 2004/0018639 A1    Jan. 29, 2004

Related U.S. Application Data

(63) Continuation-in-part of application No. 08/641,936, filed on May 1, 1996, now abandoned, which is a continuation-in-part of application No. 08/485,548, filed on Jun. 7, 1995, now abandoned, which is a continuation-in-part of application No. 08/431,883, filed on May 1, 1995, now abandoned.

(51) Int. Cl.
*A61K 39/38* (2006.01)
*A61K 35/26* (2006.01)

(52) U.S. Cl. .................................. 424/184.1; 424/580
(58) Field of Classification Search ................... 424/580
See application file for complete search history.

(56) References Cited

U.S. PATENT DOCUMENTS 4,415,553 A * 11/1983 Zhabilov et al. ......... 424/277.1
5,783,557 A     7/1998 Burstein et al.

FOREIGN PATENT DOCUMENTS

| EP | A 0 149 468 | 7/1985 |
|----|-------------|--------|
| EP | A 0 392 315 | 10/1990 |
| WO | WO A 89 05455 | 6/1989 |
| WO | WO A 93 21943 | 11/1993 |

OTHER PUBLICATIONS

Antonsen, K. P., et al., 1992, Immunoadsorption.strategies for antigen elution and production of reusable adsorbents, Biotech. 8(3):168-178.*
Jack, G. W., 1994, Immunoaffinity chromatography, Mol. Biotech. 1(1):59-86.*
Sanz-Nebot, V., et al., 1999, Fractionation and characterization of a crude peptide mixture from the synthesis of eledoisin by liquid chromatography-electrospray ionization mass spectrometry, J. Chromat. A, 846(1-2):25-38.*
Lajmi, A. R., et al., 2000, Short, hydrophobic, alanine-based proteins based on the basic region/leucine zipper protein motif: Overcoming inclusion body formation and protein aggregation during overexpression, purification, and renaturation, Prot. Exp. Purif. 18(3):394-403.*
Scopes, R.K., 2000, Overview of protein purification and characterization, Curr. Prot. Prot. Sci., John Wiley & Sons, Inc., 1.1.1- 1.1.6.*
Navratilova, I., et al., 2005, Solublization, stabilization, and purification of chemokine receptors using biosensor technology, Anal. Biochem. 339(2):271-281.*
Harvima, R. J., et al., 1988, Hydrolysis of histones by proteinases, Biochem. J. 250(3):859-864.*
Hayashi, H., and K. Iwai, 1976, Calf thymus histone H2A, J. Biochem. 80(4):681-692 (abstract only provided).*
Schnittman et al., "Human Immunodeficiency Virus and Acquired Immunodeficiency Syndrome: An Update," Adv. Int. Med., vol. 39, pp. 305-355 (1994).
Dorner et al., "Minimum Safety Requirements for Preclinical Testing," Dev. Biol. Stand., vol. 81, pp. 245-252 (1993).
Saag, M., "Clinical Spectrum of Human Immunodeficiency Virus Diseases," AIDS: Biology, Diagnosis, Treatment and Prevention, fourth edition, Lippincott-Raven Publ., pp. 203-213 (1997).
Graham et al., "Candidate AIDS Vaccines," New England Journal of Medicine, vol. 333, pp. 1331-1339, (1995).
Haynes, B., "Scientific and Social Issues of Human Immunodeficiency Virus Vaccine Development," Science, vol. 260, pp. 1279-1286 (1993).
Gait et al., "Progress in Anti-HIV Structure-Based Drug Design," Tibtech, vol. 13, pp. 430-438.
Anderson, et al., "Effect of Dose and Immunization Schedule on Immune Response of Baboons to Recombinant Glycoprotein 120 of HIV-1," J. Infect. Diseases, 160:960 (1989).
Jacobson et al., "Surrogate Markers for Survival in Patients with AIDS and AIDS related complex treated with Zidovudine," BMJ, 302:73 (1991).
Stein, et al., "CD4+ Lymphocyte Cell Enumeration for Prediction of Clinical Course of Human Immunodeficiency Virus Disease: A Review," J. Infect. Diseases 165:352 (1992).
Yarchoan et al., "Clinical Aspects of Infection with AIDS Retrovirus: Acute HIV Infection, Persistant Generalized Lymphadenopathy, and AIDS-Related Complex," in AIDS: etiology, diagnosis, treatment and prevention, eds. DeVita et al., pp. 107-120 (1988).
Fasman, G., "CRC Handbook of Biochemistry and Molecular Biology," CRC Press Inc., Boca Rotan, Florida, pp. 294-300 (1989).
Stollar, David et al., "Separation of Anti-histone Antibodies from Noninnune Hitone-precipitating Serum Proteins, Predominantly a2-Macroglobulin," Arch. Biochem. & Biophys., vol. 190(2) pp. 398-404 (1978).
Stein, D. et al., Immune-Based Therapeutics: Scientific Rationale and the Promising Approaches to the Treatment of the Human Immunodeficiency Virus-Infected Individual.

(Continued)

*Primary Examiner*—Jeffrey S. Parkin
(74) *Attorney, Agent, or Firm*—Berliner & Associates

(57) ABSTRACT

This invention relates to the area of immunology and virology, and specifically relates to compositions obtainable from mammalian thymus cells which are useful as diagnostics, vaccines, and therapeutics for human immunodeficiency virus (HIV) infection and related diseases such as acquired immunodeficiency syndrome (AIDS) and AIDS-related complex (ARC). The diagnostic, vaccination, and therapeutic methods, and devices, using these compositions are also disclosed.

12 Claims, 20 Drawing Sheets

OTHER PUBLICATIONS

Saag, Michael, "Use of Virologic Markers in Clinical Practice," Journal of Acquired Immune Deficiency Syndrome and Human Retrovirology, vol. 15, pp. S3-S13 (1997).

Shohat et al., Immune Modulation of a T-Suppressor Cell Lymphoma by Thymic Humoral Factor, a Thymic Hormone, Biochemistry, vol. 27, pp. 4066-4071 (1988).

Burstein et al., "Thymic Humoral Factor λ 2: Purification and Amino Acid Sequence of an Immunoregulatory Peptide from Calf Thymus," American Chemical Society, vol. 27(11) pp. 4066-4071 (1988).

Saag, Michael, "Candidate Antiretroviral Agents for Use in Postexposure Prophylaxis," American Journal of Medicine, Vol. 102(5B) Supplement, pp. 25-30 (1997).

Kisselev et al., "Human Immunodeficiency Virus Type 1 Proteinase Is Rapidly and Efficiently Inactivated in Human Plasma by Macroglobulin," vol. 375, pp. 711-714 (1994).

Athauda et al., "Entrapment and Inhibition of Human Immunodeficiency Virus Proteinase by $\alpha_2$-Macroglobulin and Structural Changes in the Inhibitor," J. Biochem, vol. 113, pp. 742-746 (1993).

Trainin, Nathan, Prospects of AIDS Therapy by Thymic Humoral Factor, a Thymic Hormone, Nat. Immun Cell Growth Regul, pp. 155-159 (1990).

Rager-Zisman et al., 'Thymic Humoral Factor, THF-λ2, Enhances Immunotherapy of Murine Cytomegalovirus (MCMV) Infection by Both $CD4^+$ $CD8^+$ Immune T Cells, Immunology Letters, pp. 23-31 (1994).

Pecht et al., "Potentiation of Myeloid Colony-Formation in Bone Marrow of Intact and Neonatally Thymectomized Mice by the Thymic Hormone THF-λ2," Experimental Hematology, vol. 21, pp. 277-282 (1993).

* cited by examiner

ANTIVIRAL COMPOSITIONS COMPRISING LYSINE-RICH HISTONE FRACTIONS PREPARED BY PEPSIN TREATMENT OF THYMIC CELL NUCLEI

CROSS REFERENCE TO RELATED APPLICATIONS

This is a continuation-in-part patent application of U.S. patent application Ser. No. 08/641,936, filed on May 1, 1996, now abandoned, which is a continuation-in-part of U.S. patent application Ser. No. 08/485,548, filed on Jun. 7, 1995, now abandoned, which in turn is a continuation-in-part of U.S. patent application Ser. No. 08/431,883, filed on May 1, 1995, now abandoned.

BACKGROUND

1. Field of Invention

This invention relates to the area of immunology and virology, and specifically relates to compositions obtainable from mammalian thymus cells which are useful as diagnostics, vaccines, and therapeutics for human immunodeficiency virus (HIV) infection and related diseases such as acquired immunodeficiency syndrome (AIDS) and AIDS-related complex (ARC). The diagnostic, vaccination, and therapeutic methods, and devices, using these compositions are also disclosed.

2. Related Art

Bone marrow produces cells which are destined to become immune cells. These cells become lymphocytes or phagocytes. Lymphocytes are small white blood cells that bear the major responsibility for carrying out the activities of the immune system. The two major classes of lymphocytes are B cells and T cells. B cells mature in the bone (thus the term "B cells") marrow. T cells migrate to the thymus (thus the term "T cells") where they multiply and mature into cells capable of immune response. Upon exiting the bone marrow and thymus, both B and T cells travel widely and continuously throughout the body.

There are two types of T cells, regulatory and cytotoxic T cells, which contribute to the immune defenses in two major ways. Chief among the T cells are "helper/inducer" cells. Identifiable by the T4 cell marker, helper T cells are essential for activating B cells and other T cells as well as natural killer cells and macrophages. Cytotoxic T cells are killer cells which, for example, directly attack and rid the body of cells that have been infected by viruses or transformed by cancer.

Important phagocytes are monocytes and macrophages. Monocytes circulate in the blood, then migrate into tissues where they develop into macrophages ("big eaters"). Macrophages are found throughout the body tissues and are versatile cells that play many roles. As scavengers, they rid the body of worn-out cells and other debris. Foremost among cells that present antigen to T cells, having first digested and processed it, macrophages play a crucial role in initiating the immune response. As secretory cells, monocytes and macrophages are vital to the regulation of immune responses. They also carry receptors for lymphokines that allow them to be "activated" to pursue microbes and tumor cells.

Acquired Immunodeficiency Syndrome (AIDS) is caused by a virus, the human immunodeficiency virus (HIV). HIV destroys helper T cells and is harbored in macrophages and monocytes. AIDS is characterized by various unusual infections and otherwise rare cancers. HIV also damages tissue of the brain and spinal cord, producing progressive dementia. Entry of HIV-1 into helper T cells involves the primary receptor CD4 and co-receptors CCR5 and CXCR4. The first step in cell entry occurs when the HIV-1 glycoprotein gp120 binds to the CD4 receptors on target cells. The next step is an interaction between the HIV-1 envelope protein and the co-receptor CCR5. Once gp120 interacts with receptor and co-receptor, the HIV-1 envelope protein gp41 undergoes a conformational change and literally brings the viral membrane into close proximity with the cell membrane. Fusion of two lipid bilayers then occurs, allowing intracellular entry of the viral contents.

When HIV infects a human patient, it incorporates itself into the deoxyribonucleic acid (DNA) of the immune cells and for a variable period of between 3 months to years, the patient may not exhibit any immunodeficiency symptoms and sometimes does not produce a detectable level of antibodies against AIDS. Since an initial HIV infection may not immediately lead to detectable clinical disease symptoms or a detectable level of antibodies, the term "HIV infection" as used herein encompasses both the infection and any disease resulting therefrom, the latter being termed "HIV-related diseases". Examples of HIV-related diseases are AIDS and ARC. After the above incubation period, the HIV multiplies within the infected cell and eventually bursts the host cells which release the newly formed viruses. Since the host cells are destroyed in the process, the patient's immune system is impaired and the host is susceptible to opportunistic diseases that a human with intact immune system is not susceptible to. In human, generally the AIDS virus will multiply and the human will eventually die from severe immunodeficiency. Interestingly, only humans suffer from AIDS. When a non-human mammal, such as a rabbit, mouse, rat or cow, is injected with HIV, the animal may temporarily have some T cells destroyed. However, 14 to 21 days post-infection, the animal would mount an antibody attack and does not succumb to AIDS. Thus, there is no animal model for AIDS.

Currently, there is no cure or effective therapeutic for AIDS. Research in this area is underway.

There is also a continuous search for a method for accurately diagnosing AIDS at an earlier stage of the disease. Currently, the commercially available diagnostic tests are generally directed to detecting the patients antibodies against HIV. Such tests have a window of about 14 to 21 days from the time the patient is infected with AIDS to the time the patient produces antibodies against the virus. Therefore, if a patient is tested during this window of time, the tests will produce a false negative result. On the other hand, some of these tests may also give false positive results due to non-specific binding of the antibodies. Another means for detecting the viral infection is through nucleic acid hybridization.

Unless otherwise noted, the following is based on Stein, D. S, et al., . Infect. Diseases, 165: 3 52 (1992). The surrogate marker that most closely correlates with the stage of HIV infection is the $CD4^+$, or T helper, cell count. HIV-1 envelope glycoprotein, gp120, specifically binds to the CD4 receptor that is expressed in greatest concentration in a subset of T lymphocytes and in lower amounts on monocytes and macrophages. Cells expressing CD4 receptors are termed the "helper/inducer" subset, reflecting their role as both helper cells for B cell responses for antigens expressed on cells bearing human leukocyte antigen (HLA) class II receptors and inducer cells that cause T cells to suppress immune responses. The selective loss of $CD4^+$ cells results in numerous immune defects associated with susceptibility to the opportunistic infections that are the hallmark of AIDS.

The HIV core antigen p24 can be detected before the appearance of HIV antibodies. After the appearance of HIV antibodies by the screening enzyme-linked immunosorbent assay (ELISA), p24 antigenemia generally becomes undetectable, though it can occasionally persist and often will recur later in the disease. HIV-I titers found in plasma and peripheral blood mononuclear cell cultures also fall rapidly as specific antibodies are detectable, suggesting at least a transiently effective host immune response. Markers of immune stimulation includes $\beta_2$-microglobulin.

In patients followed from the time of seroconversion, CD4+ cell decline has been correlated with progression to AIDS. Serum levels of $\beta_2$-microglobulin and detection of p24 antigen in blood were also both independently correlated with rates of progression. Combined with CD4 cell counts, use of $\beta_2$-microglobulin and p24 antigen increased prognostic accuracy for progression to AIDS compared with CD4+ cell count alone.

However, it was rare for seroconverters to have a consistent decline in their percentage of CD4+ cells over the next three years. In the interval between visits, stable or declining levels of CD4+ cell percentages were found in 38% of subjects, with 12% experiencing declines followed by a leveling in their rates of loss of CD4 cells. Overall, 62% experienced declines in their CD4+ cell percentage over three years of follow-up.

In a study of 306 HIV-infected seropositive homosexual men with unknown times of seroconversion, both a CD4+ cell count <500/μl and p24 antigen detection were predictive of AIDS within 30 months.

Increased CD8+ cell counts were found to be somewhat predictive of subsequent development of AIDS.

To better correlate clinical end points, such as survival and progression to AIDS, with surrogate markers of antiviral therapy effects, analysis of additional markers such as neopterin and $\beta_2$-microglobulin, among others, have been combined with the CD4 cell count and p24 antigen.

In a limited study {Jacobson, M. A., *BNJ*, 302:73 (1991)} of patients with AIDS and ARC who tolerated an anti-AIDS drug, zidovudine, and who survived for 12 weeks, the following was found.

After controlling for three factors (age, diagnosis of AIDS at baseline, log of the baseline serum neopterin concentration), the log of the CD4+ cell count at 8-12 weeks, but not the change over time, best predicted subsequent survival. A decrease in $\beta_2$-microglobulin concentration at 8-12 weeks significantly predicted survival and, combined with the log of the CD4+ cell count, provided the best predictive model. Decreases in p24 antigenemia, serum neopterin concentrations, and the Karhofsky performance status (a measure of function in routine activities) did not significantly correlate with survival on therapy.

Stein, D. S., et al., above, conclude that changes in CD4+ cell counts and other surrogate markers may be increasingly used as the sole end point for investigations of antiretroviral activity, of a drug or therapy, in patients with early HIV infection.

SUMMARY OF THE INVENTION

One aspect of the invention presents compositions useful for diagnosing and treating HIV infections such as AIDS and ARC.

Another aspect of the invention presents methods for detecting HIV infection using the above compositions.

Another aspect of the invention presents methods for treating HIV infection using the above compositions.

Another aspect of the invention presents methods for preparing the above composition from thymus cells of non-human mammals.

Another aspect of the invention presents devices for in vitro detection of HIV infection using the above compositions.

DETAILED DESCRIPTION

Figure 1:
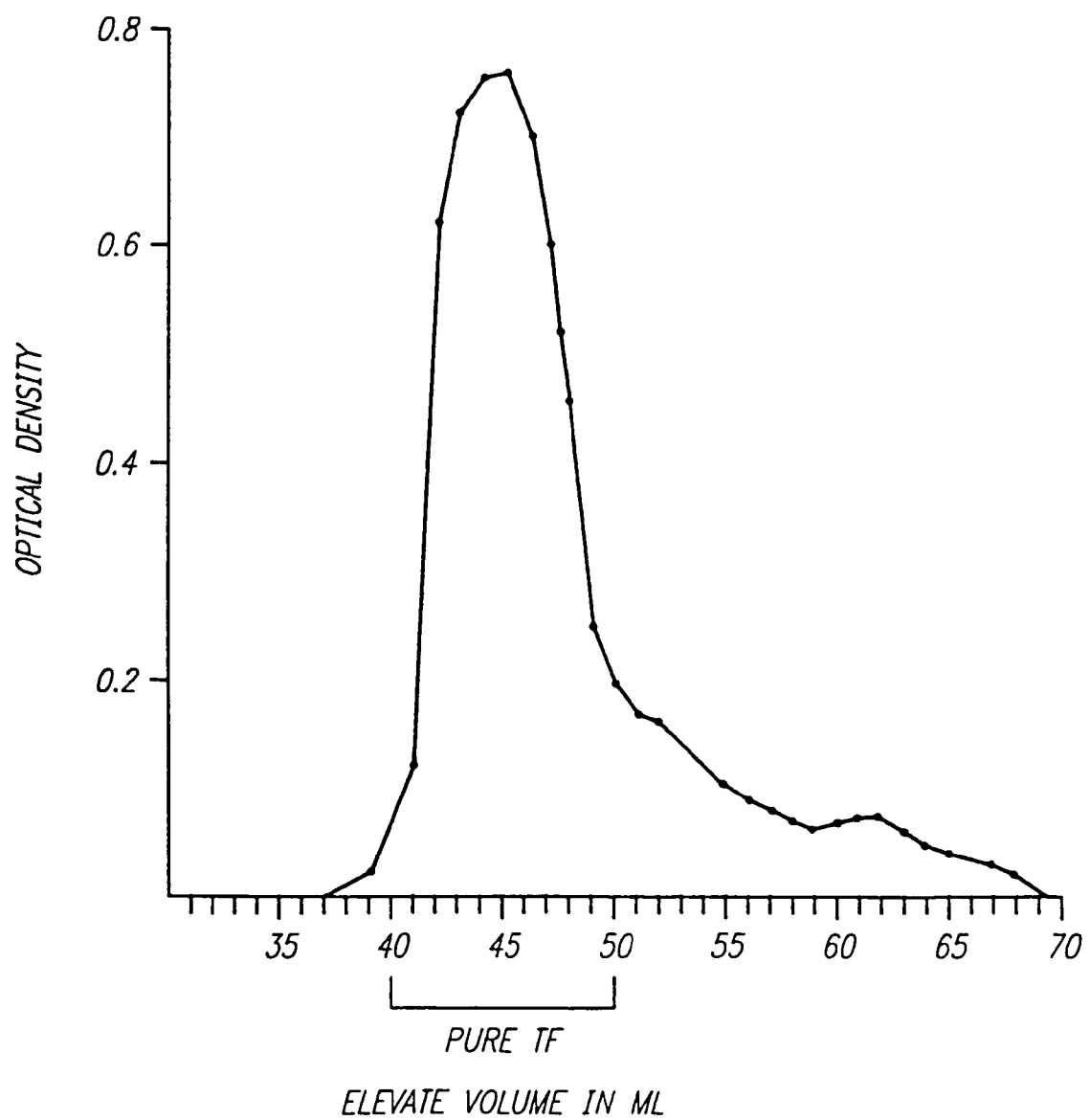
FIG. 1 presents the chromatogram of the Thymus Factor ("TF") preparation.

The present invention presents a protein, herein referred to as Thymus Factor ("TF"), which is useful for the detection of HIV which causes the fragmentation of another protein, herein referred to as aTF, which is capable of being bound to TF.

It is postulated that HIV causes the fragmentation of aTF. Thus, an individual uninfected by the HIV will have intact aTF, whereas an individual infected with HIV will have fragments of aTF. It is further postulated that, at an earlier stage of infection, the amount of aTF that are fragmented are less than at a later stage of infection. Similarly, the fragments are smaller in size in later stages of infection. Thus, detection of aTF fragments indicates an infection by HIV. The amount and size of the aTF fragments indicate the stage of the infection. aTF and its fragments can be detected by their precipitation patterns with TF, in particular, by the locations of the precipitates in relation to $\beta_2$-, $a_1$- and $a_2$-macroglobulins, e.g., in a gel electrophoresis, as described in EXAMPLE 2 below.

It was observed on a two-dimensional electrophoretic gel that TF interacted with serum from a human uninfected with HIV to form a continuous precipitation spur with $\beta_2$-, $a_{-1}$, and $a_2$ macroglobulins in the serum. The precipitation spur was broken or absent alongside one or more of the macroglobulins when TF interacted with serum from HIV-infected humans. The difference in precipitation pattern between serum from uninfected and HIV-infected individuals can be used as a method for detecting HIV infection.

It is postulated that TF precipitates aTF, found in the $\beta_2$-, $\alpha_1$-, and $\alpha_2$-macroglobulins of healthy humans, which links the $\beta_2$-, $\alpha_1$,-, and $\alpha_2$-macroglobulins and thus the precipitation spur is continuous alongside $\beta_2$-, $\alpha_1$-, and $\alpha_2$ macroglobulins. In the case of HIV-infected humans, aTF is fragmented, thus causing broken precipitation spurs or the absence of precipitation spurs with the macroglobulins.

Thus, TF precipitates with aTF found in human biological samples. Examples of the biological samples are bodily fluids such as: blood, serum and plasma. Besides the two-dimensional gel electrophoresis described in EXAMPLE 2, the precipitation pattern can be detected using a number of techniques known to one skilled in the art, including methods-used for detecting the immunoprecipitation pattern between antibodies and their antigen, examples of such techniques are described in Oudin, ., *C.R. Acad Sci*., 222:115 (1946); Oudin, ., *Methods in Medical Research*, V: 335-78, Corcoran A. C., ed., Year Book Publishers Inc. (1952); Ouchterlony, O., *Acta. Path. Microbiol. Scand*., 25:186 (1948); Ouchterlony, O., Progress in Allergy, V:1-78, Kallos P. & Wakeman B. H., Basel and Karger, New York (1958); Ouchterlony, O., Progress in Allergy, VI: 30-154, Kallos P. & Wakeman B. H., ed., Basel and Karger, New York (1962); Mancini, G. et al., *Prot. Biol. Fluids* 11*th Colloqu. Bruges*, pp. 370-3, Peters, H., ed. (1964): Mancini, G. et al., *Immunochemistry*, 2:235 (1965).

TF purified as described in EXAMPLE 5 below can bind to fragment 579-601 of HIV-1 envelope protein gp41 in a rocket gel electrophoresis assay. The binding of TF with the gp41 fragment can be used as an assay of TF activity.

TF can also be used to treat HIV infections, such as AIDS and ARC. TF can exist in a methylated or an unmethylated state. The term "TF" as used herein, unless otherwise modified, e.g. as "methylated TF", covers both the methylated and unmethylated TF.

The present invention also presents methods for obtaining TF, in particular, from thymus cells. The thymus cells are preferably from non-human mammals regardless of whether they are infected by HIV, though HIV infected non-human mammals have higher titers of TF. Examples of the non-human mammals are: monkeys, gorillas, chimpanzees, guinea pigs, cows, rabbits, dogs, mice and rats.

Both methylated and unmethylated TF can bind aTF and thus can be used to diagnose HIV infection, in particular to AIDS. However, at least in the case of sera from human test subjects, the methylated TF suffers less from non-specific binding with other proteins, compared to the unmethylated TF. Thus, methylated TF is preferred. Unmethylated TF can be chemically methylated using methods known in the art, for example, as described in EXAMPLE 1 below. Methylated TF can be used as a therapeutic for HIV infection, in particular AIDS.

TF is preferably purified from the thymus cells of freshly sacrificed, i.e., 4 hours or less after sacrifice, mammals such as monkeys, gorillas, chimpanzees, guinea pigs, cows, rabbits, dogs, mice and rats. The nuclei from the thymus cells are isolated using method known in the art. Part of their lysine-rich histone fractions are extracted using the pepsin degradation method of U.S. Pat. No. 4,415,553, which is hereby incorporated by reference. Other degradative methods such as trypsin degradation, papain degradation, BrCN degradation appear ineffective in extracting TF. The protein rich fragment of the isolate is purified by cation exchange chromatography. The proteins in the TF fractions (methylated and unmethylated) can be concentrated by any one of several techniques well known to those skilled in the art, including high salt precipitation, for example, with ammonium sulfate, or by ultrafiltration. If TF is concentrated by precipitation, it is preferably subsequently resuspended in a suitable physiologically balanced salt solution containing protease inhibitor(s).

TF Administration As Therapeutics Against HIV Infections.

Applicants observed that non-human mammals, such as cows, which were infected with HIV but did not develop AIDS, have intact TF. This invention postulates that TF plays a role in preventing the progression of HIV infections, in particular AIDS. Therefore, it would be therapeutic to administer TF to HIV infected human. The TF is preferably from non-human mammals which do not develop AIDS when infected with HIV. Methylated non-mammalian TF is preferred. Further, it is preferable to provoke an immunoresponse in the infected human under treatment. To that end, TF is preferably delivered with an adjuvant, or TF is chemically conjugated to an immunogenic carrier that would provoke an antibody response in the patient. Examples of immunogenic-carriers are: keyhole limpet and bovine serum albumin.

In one aspect of the invention, TF is used to vaccinate against, to treat, or cure HIV infections, especially AIDS and ARC. For example, TF is prepared for administration by mixing it at the desired degree of purity with adjuvants or physiologically acceptable carriers, i.e. carriers which are nontoxic to recipients at the dosages and concentrations employed. Although TF is desirably administered with an adjuvant, in situations where the initial inoculation is delivered with TF, boosters with TF may not require adjuvant.

Injections (intramuscular or subcutaneous) will be the primary route for therapeutic administration of the vaccines of this invention. However, intravenous delivery, delivery through catheter, or other surgical tubing may also be used. Alternative routes include tablets and the like, liquid formulations, and inhalation of lyophilized or aerosolized receptors. Liquid formulations may be utilized after reconstitution from powder formulations.

TF may also be administered via microspheres, liposomes, other microparticulate delivery systems or sustained release formulations placed in certain tissues including blood.

The dosage of TF administered will depend upon the properties of the formulation employed, e.g. its binding activity and in vivo plasma half-life, the concentration of TF in the formulation, the administration route, the site and rate of dosage, the clinical tolerance of the patient involved, the pathological condition afflicting the patient and the like, as is well within the skill of the physician.

Different dosages are utilized during a series of sequential inoculations; the practitioner may administer an initial inoculation and then boost with relatively smaller doses of TF.

The following is an example of a TF formulation, dosage and administration schedule. The patient is administered an intramuscular or subcutaneous injection containing 8 mg of TF (preferably 2 ml of a formulation containing 4 mg/ml of TF in a physiologically acceptable solution) or 57 µg of TF protein per 1 kg body weight of the patient. Each treatment course consists of 16 injections; with two injections on consecutive days per week for 8 weeks. The patient's disease condition is monitored by means described further below. Three months after the last injection, if the patient is still suffering from the disease, the treatment regimen is repeated. The treatment regimen may be repeated until satisfactory result is obtained, e.g. a halt or delay in the progress of the t disease, an alleviation of the disease or a cure is obtained. Preferably, TF is formulated in an aluminum hydroxide adjuvant. The final 1 ml of the final TF formulation contains: 4 mg TF, 0.016 M AlPO$_4$ (or 0.5 mg Al$^{3+}$), 0.14 M NaCl, 0.004 M CH$_3$COONa, 0.004 M KCl, pH 6.2.

Alternatively, the HIV infected patient or uninfected subject may be inoculated five months later, more preferably six months to two years later, and even more a preferably eight months to one year later to enhance the patient's "immune memory". See Anderson et al., *Infectious Diseases*, 160 (6): 960-969 (1989). Generally, infrequent immunizations with TF spaced at relatively long intervals is more preferred than frequent immunizations in eliciting maximum immune responses, and in eliciting a protective effect.

TF can be administered in various ways and to different classes of recipients. TF can also be used to vaccinate individuals who may or may not be at risk of exposure to HIV, and additionally, the vaccines are desirably administered to seropositive individuals and to individuals who have been previously exposed to HIV.

TF can be administered in combination with other antigens in a single inoculation "cocktail". TF can also be administered as in a series of inoculations administered over time. Such a series may include inoculation with the same or different preparations of HIV antigens or other vaccines.

The adequacy of the treatment parameters chosen, e.g. dose, schedule, adjuvant choice and the like, is determined by taking aliquots of serum from the patient and assaying for antibody and/or T cell titers during the course of the treatment program. T cell titer may be monitored by conventional methods. For example, T lymphocytes can be detected by E-rosette formation as described in Bach, F., *Contemporary Topics in Immunology*, Vol. 2: Thymus Dependency, p. 189, Plenum Press, New York, 1973; Hoffmnan, T. & Kunkel, H. G., and Kaplan, M. E., et al., both papers are in *In vitro Methods in Cell Mediated and Tumor Immunity*, B. R. Bloom & R. David eds., Academic Press, New York (1976). For example, the amount of T cell rosette formation may be assayed after the third but before the tenth week of TF treatment. An over sixty-five percent rosette formation indicates a good cell mediated immune response in the patient. A further indicator to monitor is aTF produced by the patient, this may be monitored by the two dimensional electrophoresis method described further below.

In addition, the clinical condition of the patient can be monitored for the desired effect, e.g. anti-infective effect. If inadequate anti-infective effect is achieved then the patient can be boosted with further TF treatment and the treatment parameters can be modified, e.g. to potentiate the immune response, such as by increasing the amount of TF and/or adjuvant, complexing TF with a carrier or conjugating it to an immunogenic protein, or varying the route of administration.

TF may optionally be administered along with other pharmacologic agents used to treat HIV infections such as AIDS and ARC. Examples of these pharmacologic agents are: AZT, antibiotics, immunomodulators such as interferon, anti-inflammatory agents and anti-tumor agents.

Diagnostic Devices for Detecting HIV Infections

Another aspect of the invention presents diagnostic devices useful for in vitro detection of HIV infection. The device is designed to allow detection of the interaction between TF and aTF in a biological sample. More preferably, in the case where the biological sample is blood, serum, or plasma the device allows for the detection of precipitation pattern of TF in relation to $\beta$-, $a_1$,- and $a_2$-macroglobulins in the sample. Thus, preferably, the device contains a site for TF and a site for the test sample. Since a two-dimensional gel electrophoresis, as described in the following EXAMPLE 2 is preferred, the device most preferably consists of a gel with slots for containing TF and the test sample such as serum sample, respectively. The device is also preferably packaged with a kit with containers for the reagents necessary for conducting the test, such as buffer solution and TF. Preferably, the device has its own electrical source, such as a battery, to allow for a two-dimensional electrophoresis to be conducted. Otherwise, it is preferably designed such that it can be connected to outside electrical source.

Having described what the applicants believe their invention to be, the following examples are presented to illustrate the invention, and are not to be construed as limiting the scope of the invention.

EXAMPLE 1

Isolation and Purification of Thymus Factor

The following experiment shows the isolation, purification, and characterization of TF from calf thymus 4 hours after sacrifice.

Extraction(s) of Lysine-Rich Histone Fraction from Thymus Cells with Enzyme Degradation by Pepsin All the buffers and solutions used in this section have been sterilized by filtration. If needed, the buffers' denoted pas were adjusted by 0.2 N Noah or 0.1 N HCl. All the chemicals, including the distilled water, for the preparation of the buffers and solutions were USP grade.

The thymus tissue and its associated connective tissues were separated from a calf within 4 hours of its sacrifice. The tissues were washed with a solution containing 0.14 M NaCl, and 0.005 M EDTA-Na$_3$ at 4° C. for 5 minutes. The wash solution was decanted and the tissues were washed a second time under the same conditions. After decantation of the wash solution, the tissues were weighed. The tissues were homogenized in 0.14 M NaCl, 0.005 M KCl, 0.005 M MgCl$_2$, 0.003 M CaCl$_2$, 0.15 M TRIS-HCl, pH 7.6, 0.25 M sucrose in a tissue homogenizes (Brinkman Polytron Homogenizes, Brinkman Instruments, Inc., Westbury, N.Y.), at 4° C. and at an rpm and for the duration of time recommended by the manufacturer of the homogenizes for removal of cell nuclei. The ratio of the tissue to the buffer was 1:4 (weight/weight).

The tissue homogenate was then filtered through gauze pad by vacuum. The filtrate was centrifuged at 1,000 g at 4° C. for 90 minutes. The supernatant was discarded. The pellet was resuspended in 0.008 NaCl, 0.003 M CaCl$_2$, 0.003 M MgCl$_2$, 0.08 M NaH$_2$PO$_4$, 0.002 M TRIS-HCl, 0.25 M sucrose, pH 5.2. The ratio of the pellet to the buffer was 1:4 (weight/weight). The resuspension was homogenated in a beaker with a magnetic stirrer at 200 rpm, at 4° C. for 5 minutes. The homogenate was then centrifuged at 3500 g, at 4° C., for 60 minutes. The supernatant was discarded. The pellet was resuspended in 0.014 M NaCl, 0.001 M CaCl$_2$, 0.002 M MgCl$_2$, 0.001 M EDTA-Na$_3$, 0.002 M TRIS-HCl, 0.25 M sucrose, pH 4.2 at a ratio of pellet to buffer of 1:4 (weight/weight). The resuspension was homogenated in a beaker with a magnetic stirrer at 200 rpm, at 4° C. for 5 minutes. The homogenate was then centrifuged at 8000 g, at 4° C. for 60 minutes. The supernatant was discarded.

The pellet was resuspended at a ratio of 1:4 (weight/weight) with a previously prepared buffer containing: 1 part volume/volume) Solution 1, 2 parts Solution 2, and 17 parts Buffer 4. Solution 1 consisted of: 10% sodium dodecyl sulfate in water/ethanol (at 55:45 v/v). Solution 2 consisted of 10% Tween 80 (in distilled water). Buffer 4 consisted of: 0.011 M $NaH_2PO_4$ and 0.19 M $Na_2HPO_4$, pH 7.4.

The resuspension was homogenated in a beaker with a magnetic stirrer at 200 rpm, at 4° C. for 15 minutes. The homogenate was then centrifuged at 12,000 g, at 4° C. for 60 minutes. The supernatant was discarded. The pellet was weighed and resuspended in 0.05 M $Na_3C_6H_5O_7$, 0.05 M $CH_3COONa$, 0.1 N HCl, pH 2.8 at a ratio of pellet to buffer of 1:4 (weight/weight). The resuspension was homogenized by tissue homogenizer at 1000 rpm, at 4° C. for 1 minute.

Pepsin (catalog number P 7000, Sigma Chemical Company, St. Louis, Mo.) diluted in distilled water at 1:10,000, with activity of 800-2500 units per mg protein, was added to the homogenate at a pepsin (powder) to pellet after homogenization weight ratio of 100:1.8. The mixture was placed in a beaker and stirred, under nitrogen atmosphere, with a magnetic stirrer at 45 rpm, at 4° C. for 12 hours.

The resulting mixture was then centrifuged at 12,000 g, at 4° C. for 60 minutes. The pellet was discarded. The supernatant was removed and precipitated with a solution consisting of saturated $(NH_4)_2SO_4$. One part of the supernatant was mixed with one part of the solution and stirred with a magnetic stirrer at 600 rpm for 6 hours at 4° C. The mixture was then centrifuged at 12,000 g, at 4° C. G for 60 minutes. The supernatant was discarded. The pellet was dissolved in a solution containing a minimal quantity of 0.1 M NaCl, 0.1 M $CH_3COONa$, 0.02 M thiodiglycol. The resulting solution was dialyzed against 0.01 M NaCl, 0.01 M $CH_3COONa$, pH 6:4 until the ammonium sulfate was removed from the dialysate.

The protein in the dialysate was measured by the Lowry method. The solution was diluted to obtain 2 mg/ml of protein. The pH of the solution was then adjusted to 7.2 by 0.1 N NaOH. A solution of 0.2 M bromoacetic acid was prepared separately by dissolving bromoacetic acid in 10 ml or less of water and the pH was adjusted to 7.0 by 0.1 N NaOH. The resulting bromoacetic acid solution was added to the protein solution and the mixture was stirred by magnetic stirrer for 48 hours under nitrogen atmosphere. The pH of the mixture was maintained at 7.2 throughout the reaction. At the end of the reaction, the ammonium sulfate precipitation step was repeated up to the step of measuring the protein concentration by the Lowry method. The final solution was diluted or concentrated, as needed, to obtain 4 mg/ml of the protein TF from 200 g of calf thymus cells.

Carboxymethyl Column Chromatography

One ml of the TF solution containing 4 mg of protein was applied to 0.9×14 cm carboxymethyl column equilibrated with 0.05 M sodium acetate. The column was washed and eluted by applying a linear gradient of sodium chloride in 0.05 M sodium acetate, pH 6.8. To create the gradient, siphon was used to connect two flasks of the same size and shape. One flask contained 50 ml of 0.05 sodium acetate, pH 6.8 and the other flask contained 50 ml of 0.05 sodium acetate containing 0.5 M sodium chloride, pH 6.8. Only the flask containing 0.5 M sodium chloride was connected to the column. The gradient was from 0 to 0.5 M sodium chloride. The two flasks must be stirred vigorously to insure good mixing. Fractions of 1 ml each were collected. The eluate was examined by a flow spectrometer adjusted to 280 nm of absorbance reading. Eluate fraction 45 was determined to contain protein (see FIG. 1). The TF fraction was centrifuged at 10,000 rpm and two bands of precipitates were observed. Fraction 45 was collected and concentrated by ammonium sulfate precipitation.

The resulting concentrated fraction was further analyzed as follows.

i) Determination of Molecular Weight

The molecular weight of the collected TF fraction was determined by silver stained 11% non-reducing SDS-PAGE (sodium dodecyl sulfate-polyacrylamide gel electrophoresis) using the Laemmli method {Laemmli, U.K., *Nature*, 227:680 (1970)} and according to the instruction disclosed in Sigma Technical Bulletin MWS-877L (Sigma Chemical Company, St. Louis, Mo.). Rapid Silver Stain (RSK-1, Sigma Chemical Company) was used to stain the proteins. Low molecular weight standard (M 5630, Sigma Chemical Company) was used, it contained a mixture of five proteins (total protein concentration 1 ng/ml): bovine serum albumin (66,000 molecular weight, MW); porcine heart fumarose (48,500 MW); bovine erythrocytes carbonic anhydrase (29,000 MW); bovine milk β-lactoglobulin (18,400 MW); and bovine milk a-lactalbumin (14,200 MW).

Two bands were observed on the gel. The larger band was unmethylated TF which constituted 98% of the TF fraction. The smaller band was methylated TF which constituted the remaining 2% of the TF fraction. Based on the protein calibration curve, unmethylated TF was determined to have a molecular weight of about 35 Kilodalton (Kd) and methylated TF has a molecular weight of about 28 Kd.

The TF composition (including methylated and unmethylated TF) has a pH of between about 7.64 and 8.6 by pH titration. The isoelectric point of the TF composition is about 5.6±0.1 as determined by immunoelectrical focusing.

Methylation of the Protein Found in the TF Fraction

The TF was methylated to form a methylated TF preparation for use in the following EXAMPLES. The methylation was conducted as follows.

TF was mixed with $CH_2BrCOOH$ insufficient quantity to produce a final solution of 0.2 M $CH_2BrCOOH$. For example, 2.78 g $CH_2BrCOOH$ was dissolved in 10 ml distilled water and added to 100 ml TF containing 700 mg TF (7 mg/ml). The pH of the mixture was adjusted to and maintained at 7.24 with 0.1 M in NaOH. The mixture was allowed to incubate from 6 to 8 hours. The TF protein in the resulting aqueous fraction was concentrated by ammonium sulfate precipitation, using techniques known in the art. To 10 ml of the methylated TF fraction was added an equal volume of saturated ammonium sulfate. The mixture was refrigerated 12 hours and then centrifuged 20,000 rpm for 60 minutes. The pellet was removed and dissolved in a final buffer containing 0.1 M NaCl, 0.1 M sodium citrate, 0.02 M thiodiglycol. The mixture was then dialyzed against the same buffer, to remove the ammonium sulfate, for 24 hours.

EXAMPLE 2

Diagnosis of HIV Infections

The methylated TF obtained from EXAMPLE 1 was used to determine whether a given human serum sample was from a patient infected with HIV. The experiment was conducted as follows:

The human serum samples in this Example were provided by AIDS Health Foundation, Los Angeles, Calif. The Foundation had tested the samples using commercially available enzyme-linked immunosorbent assay (ELISA) and Western blot which detected the patient's antibodies against the HIV.

The ELISA was conducted first. If the ELISA indicated HIV infection (HIV-positive), Western blot was conducted as a confirmation test.

Using the present invention, the above samples were tested using two-dimensional electrophoresis. The equipment used was a submarine mini gel electrophoresis unit. (Catalog No. E 0638, Sigma Chemical Company). The unit contained a buffer chamber with a capacity for 800 ml of buffer. The unit was also equipped with a peristaltic pump for recycling the buffer. The power source had an output range of 20 to 240 V, 0 to 100 mA, with a constant current and voltage output.

Figures 2, 3:
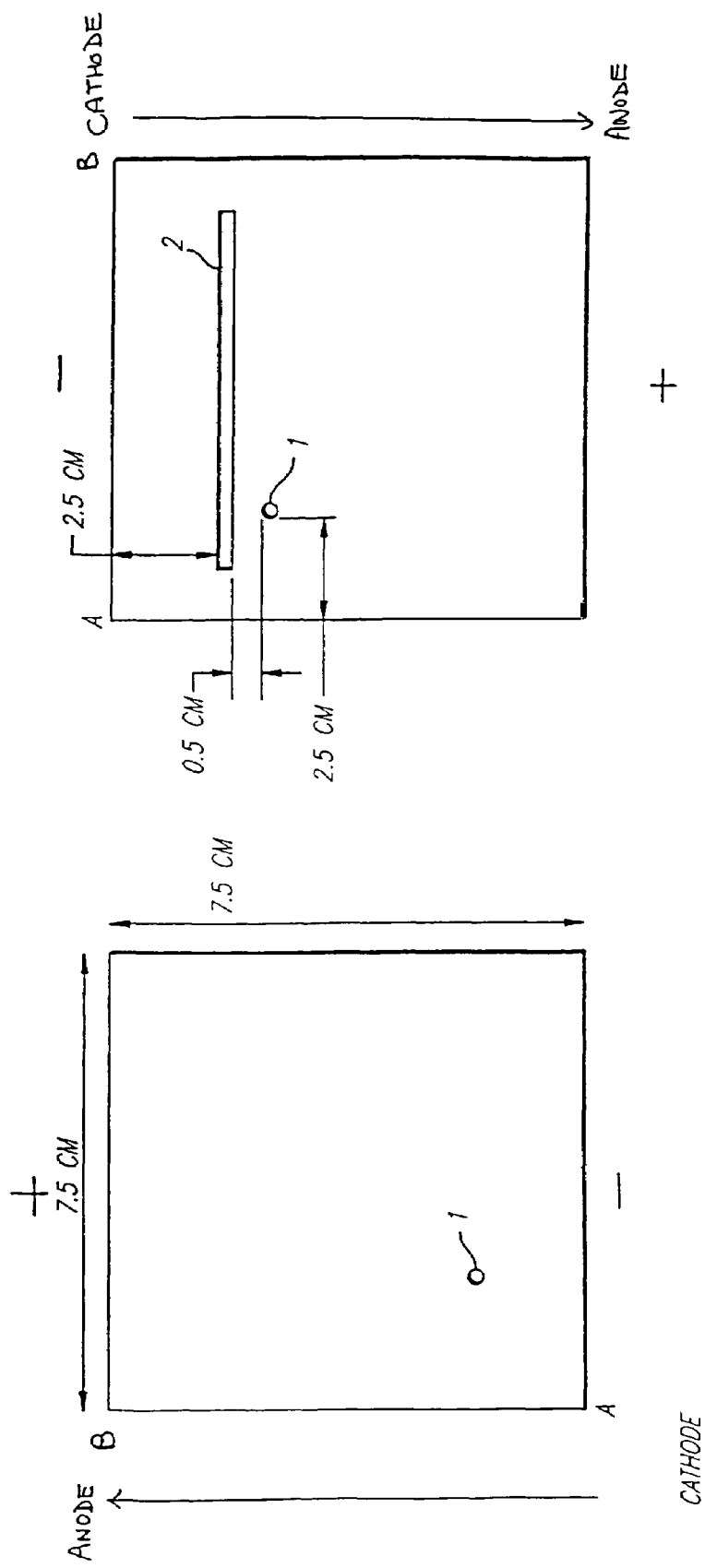
FIG. 2 graphically presents the placement of the two-dimensional gel in its first-dimension.
FIG. 3 graphically presents the placement of the two-dimensional gel in its second-dimension.

The gel was prepared with 1% agarose (Catalog No. A 4679, Sigma Chemical Company). The gel buffer consisted of: 0.0257 M TRIS-HCl, 0.009 M sodium borate decahydrate, 0.067 M glycine, 0.0034 M sodium acetate trihydrate, 0.015 M 2-mercaptoethanol.and 0.015 M thiodiglycol, pH 7.64. 14.25 ml of the 1% melted agarose gel was applied to the electrophoretic gel plate. The solidified gel was 0.2 cm thick and at a dimension of 7.5 cm×7.5 cm. The gel was overlaid with the same buffer. A well of 0.9 mm radius was punctuated in the gel using a syringe needle (with a bore of 0.9 mm in diameter) which delivered 5 µl of the serum sample. For the first-dimension run, to separate the serum proteins, the voltage used was 9 V/cm, the current was 27 mA/cm$^2$, and the electricity was applied for 90 minutes at 14° C. FIG. 2 schematically presents the arrangement for the first-dimension gel, 1 denotes the well for the serum sample. For the second-dimension run, the gel plate was turned 90° and a 0.9×45 mm trough was removed from the gel from the side of the new cathode position, between the new cathode position and the serum hole and perpendicular to the cathode-anode line. FIG. 3 schematically presents the arrangement for the second-dimension gel, 2 denotes the trough. The trough was filled with 100 µl of methylated TF of EXAMPLE 1. The same voltage and current was applied to the gel for 50 minutes at 14° C. Throughout the two-dimensional electrophoresis, the buffer was recirculated at 25 ml/min. After the last run, the power was turned off, and the gel was removed after a few seconds. The gel was then simultaneously fixed and stained, for 45 minutes, in a solution containing: 3 parts methanol, 1 part ethanol, 12% acetic acid and 0.1% bromophenol blue (Catalog No. B-8026, Sigma Chemical Company). The gel was destained by soaking it in distilled water for 3 to 4 hours and dried.

For molecular weight determination, a control two-dimensional electrophoresis was separately conducted under the same conditions but using the silver stain low, molecular weight markers instead of serum and TF described in EXAMPLE 1.

Figure 4:
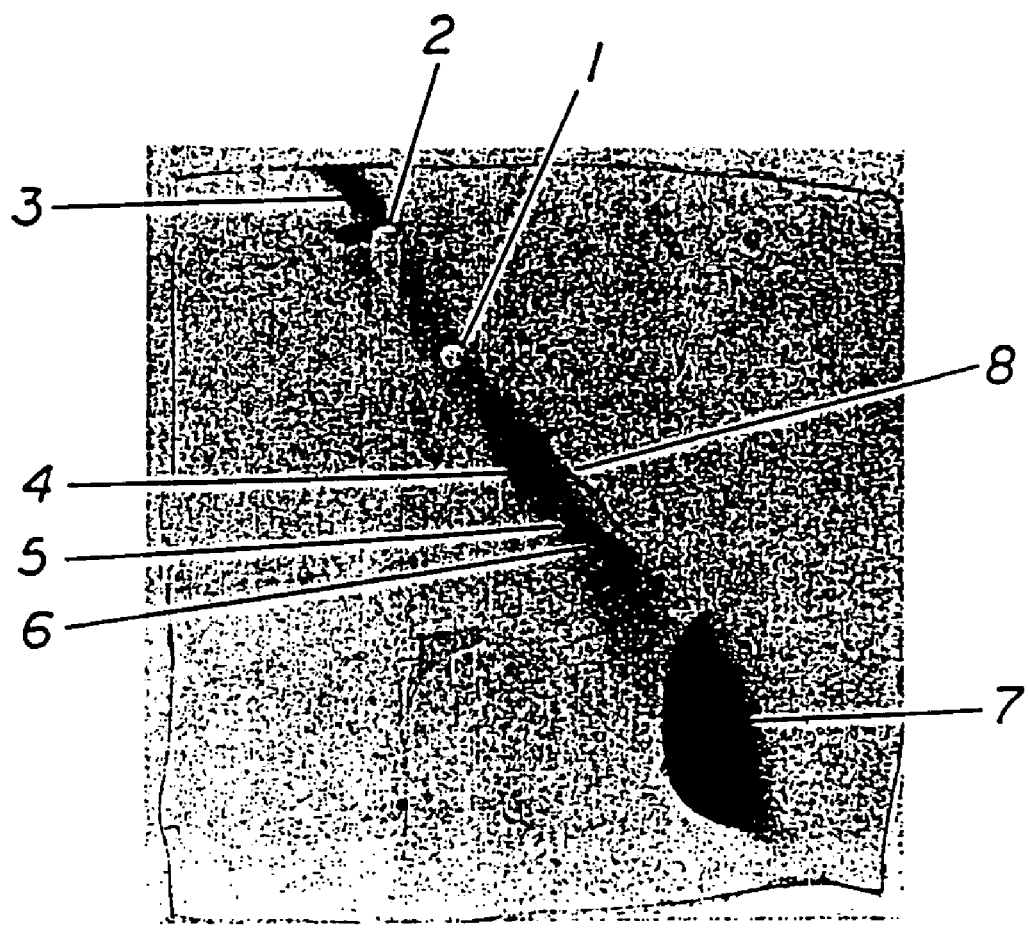
FIGS. 4 to 11, are photographs of two-dimensional gels showing the precipitation patterns of TF with serum samples from HIV-positive or AIDS human subjects and a healthy human subject.

The positions of serum proteins on the two-dimensional electrophoretic gel were shown in FIG. 4. In FIG. 4, the immunoglobulin stain 3 appeared next to the serum well 1 containing the patient's serum sample, so did β-macroglobulin 4, further from the serum well were a2-macroglobulin 5, $a_1$-macroglobulin 6, and albumin 7.

Precipitations of TF with aTF in the sera were detected by the appearance of fine opaque lines (precipitation spurs). The patterns of these precipitation spurs indicate whether the test subject has HIV infection:

A continuous precipitation spur 8 continuing alongside β- and $\alpha_1$-macroglobulins, to alongside $\alpha_2$-macroglobulins, as shown in FIG. 4, indicates that the test subject is not infected with HIV: a non-continuous (i.e. broken) precipitation spur alongside β-, $\alpha_1$-, and $\alpha_2$-macroglobulins, and/or spurs) that are not alongside any or all of the macroglobulins indicate HIV infection.

Further, as the test subject's HIV infection (such as AIDS) progresses, the precipitates were less and thus the precipitation spurs became fainter.

The above observation suggests that aTF, found in healthy sera, was fragmented during HIV infection resulting in broken spurs of precipitation between TF and the fragmented aTF. The fragments were of smaller molecular weights than the whole aTF, thus they migrate further in the electric field. Thus the precipitation spurs were further from the TF trough. Without wishing to be bound by this hypothesis, it is hypothesized that the aTF would be fragmented into more parts when the AIDS, the HIV-related disease or the HIV infection is more advanced, thus there would be more broken precipitation spurs at greater distances from the groove containing TF. Thus, the pattern of precipitation is also indicative of the stage of the disease's progression.

Figure 5:
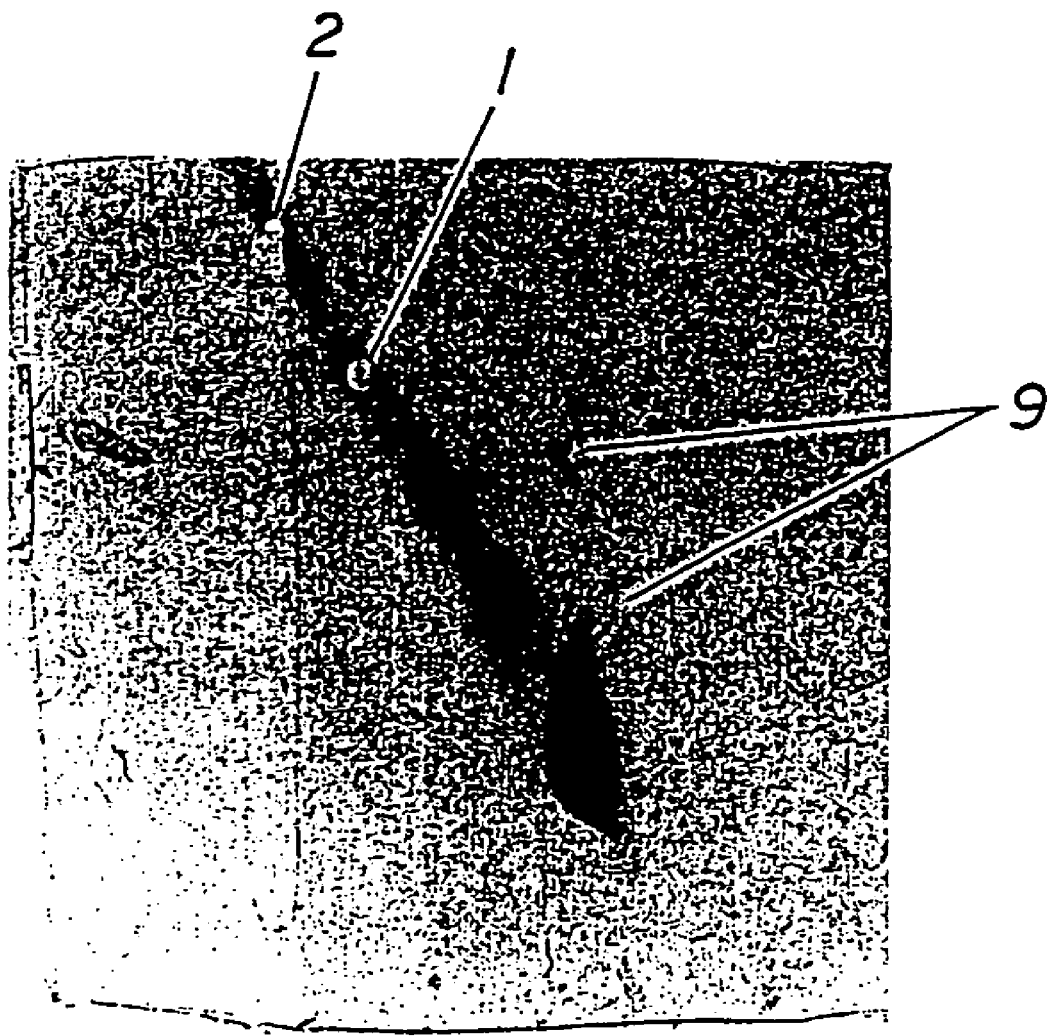

Thus, the gels shown in the drawings are interpreted as follows:

FIG. 5 shows broken precipitation spurs 9 which indicate that the subject was HIV-positive. This subject's serum was taken and tested HIV-positive by ELISA and the test of the present invention. At the time the serum was taken, the subject did not show any clinical symptoms of AIDS.

FIGS. 6 to 9 show position 10, where β-macroglobulin was located and where a healthy subject's precipitation spur would be adjacent to, and the spur would be a continuous spur spanning alongside the locations of β-, $\alpha_1$-, and $\alpha_2$ macroglobulins (as in FIG. 4). In contrast, in FIGS. 6 to 9, the subjects' precipitation spurs 11 were broken (i.e. not continuous alongside the locations of β-, $\alpha_1$-, and $a_2$ macroglobulins) and below position 10. The positions of the test subject's precipitation spurs indicated that they were of lesser molecular weight than the precipitation spurs of a healthy subject. The broken fragments and spurs and their lesser molecular weights indicated that the test subjects were HIV-positive. Between three to six months before the present tests, these subjects were tested HIV-positive by ELISA. The present test used the sera taken at the same time as that for the ELISA test. At the time of the present tests, the subjects exhibited clinical symptoms of AIDS. The severity of the disease among the subjects were in the order of subject of FIG. 6 (most severe case of AIDS), FIG. 7, FIG. 8 and FIG. 9 (least severe case of AIDS). The clinically observed severity of the disease was consistent with the patterns of the precipitations in the figures shown. First, gels with precipitation spurs that are further away in distance, from the location of spurs expected of a healthy subject, indicate smaller fragments of aTF and thus a more severe case of AIDS than gels with precipitation spurs that are closer to the expected location of the spurs of a healthy patient. For example, this distance can be determined based on the relative distance of the first precipitation spur, i.e. the spur closest in vertical distance to the serum hole 1, from the expected spur of a healthy subject should be. The further the relative distance, in both the horizontal and vertical directions from the location of the health subject's spur, the more severe the disease. Second, if the above factors cannot distinguish between the gels of two AIDS subjects, the disease is less severe for the subject who has a gel showing spurs) that are more intense and lesser in number. Lesser number of precipitation spurs and a heavier precipitation indicate aTF that is less fragmented and at a higher level, and therefore, a less severe case of AIDS.

Figure 6:
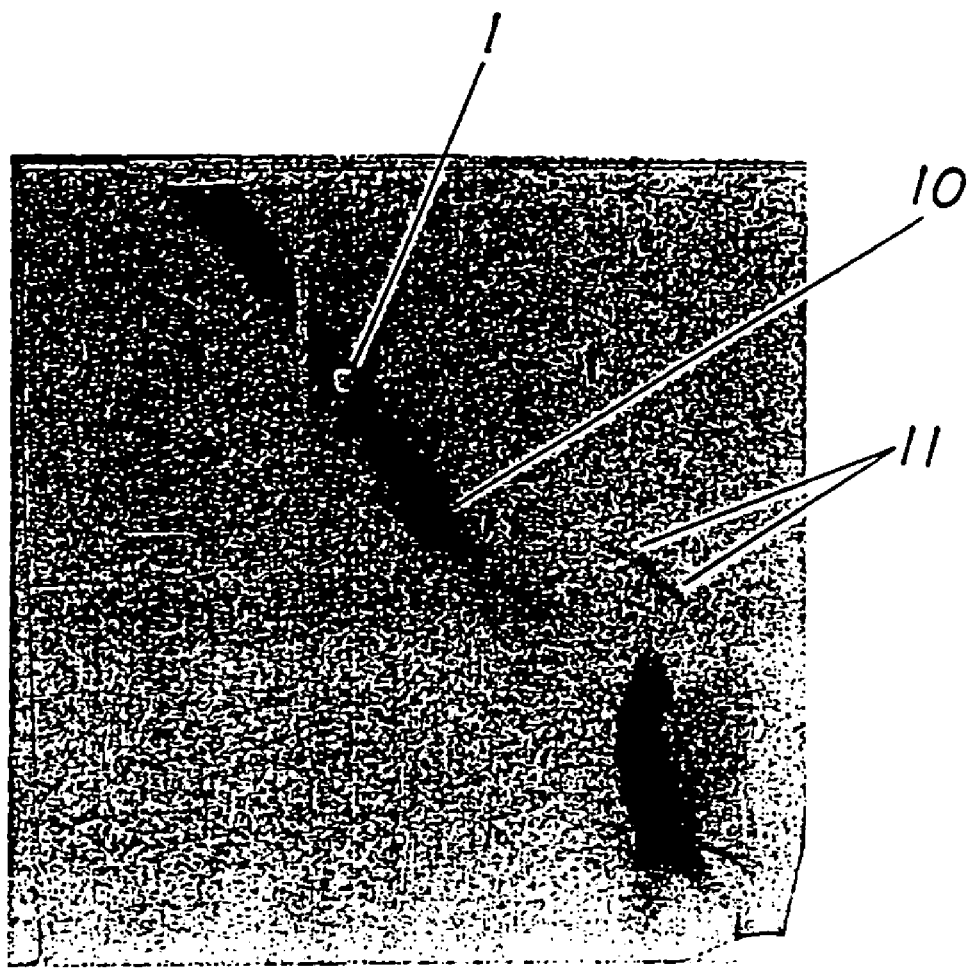
Figure 7:
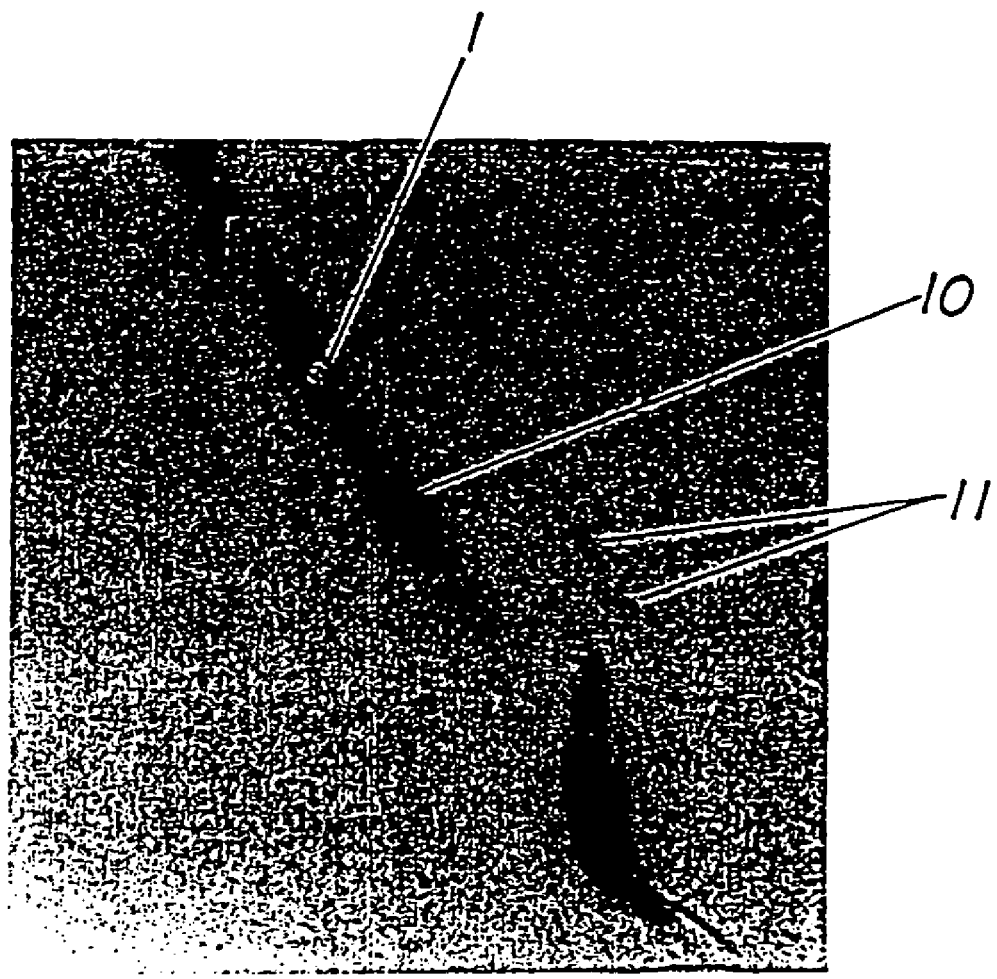
Figure 8:
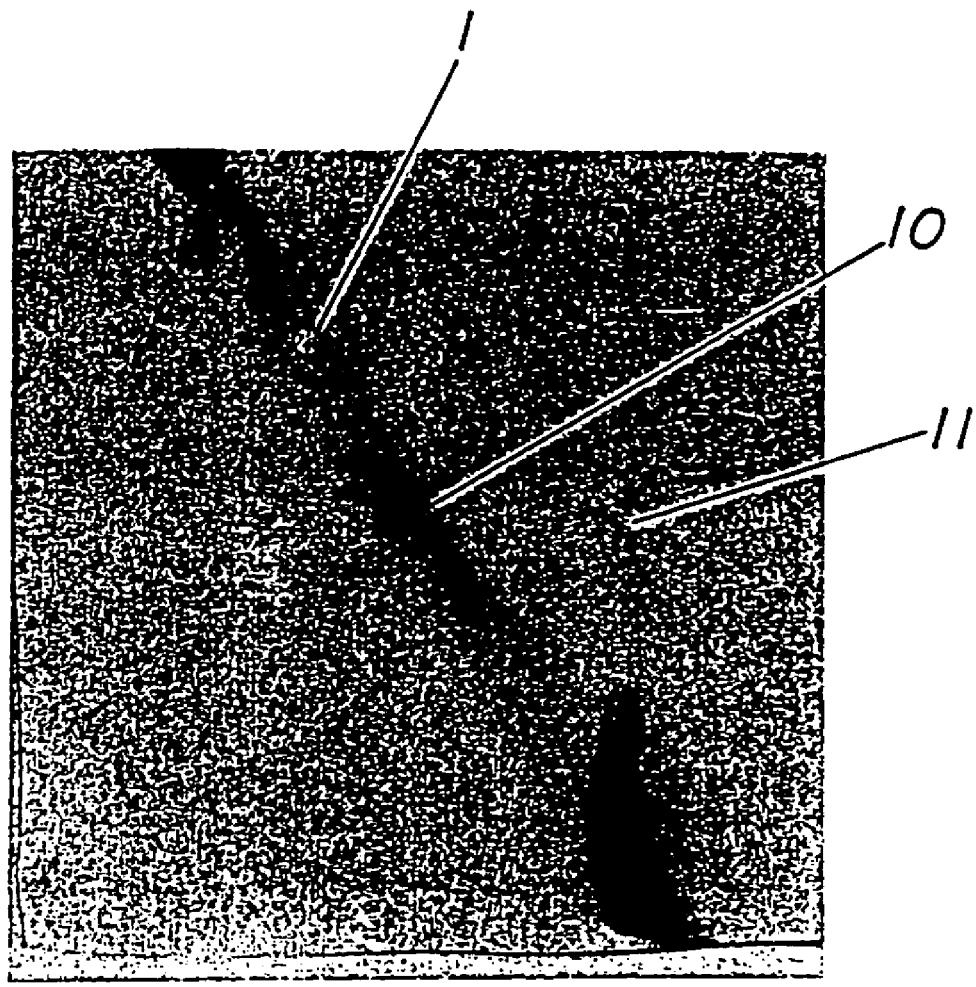
Figure 9:
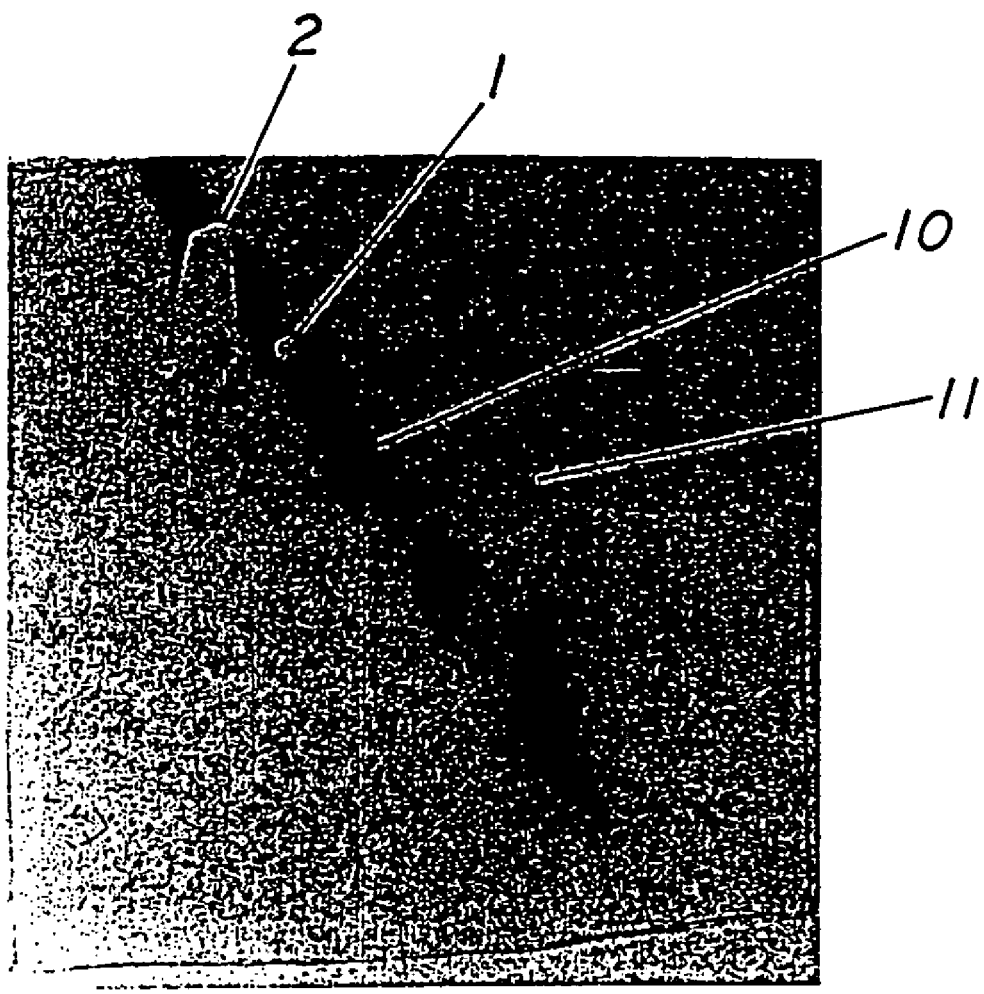
Figure 12:
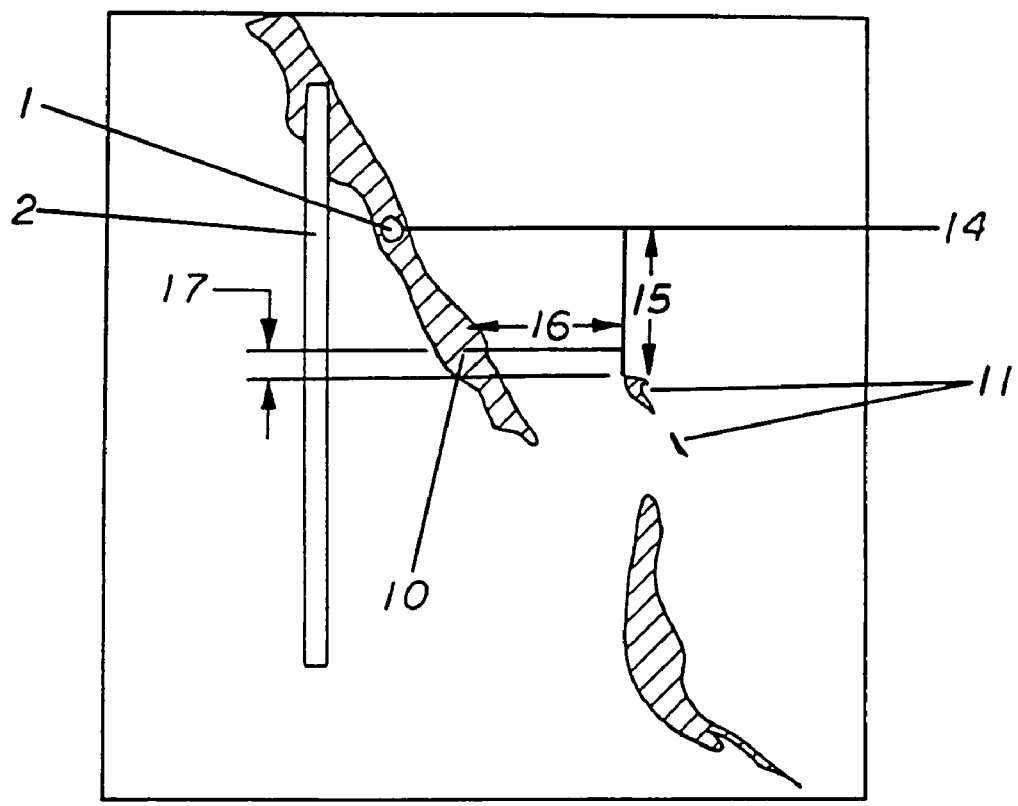
FIG. 12 graphically presents FIG. 7, and the distances measured for its analysis.

An example of the application of the first analysis is applied to analyzing FIGS. 6 to 10. In order to normalize the comparison of these figures, a fixed point for all the figures, in this case, serum hole 1 is chosen as the baseline 14. The first precipitation spur is the one closest in vertical distance 15 from the baseline 14 (see FIG. 12). Since a healthy subject's precipitation spur would stretch from adjacent to the locations of β- and $α_1$-macroglobulins, to the location of $α_2$-macroglobulins (as in FIG. 4), one can measure the relative distance from either the location of β-, $α_1$-, or $α_2$-macroglobulins. In this case, the location of β-macroglobulin 10 was chosen. Both the vertical 17 and horizontal 16 distances of the spur from the location of β-macroglobulin 10 (see FIG. 12) were measured and compared for these series of figures. Subjects whose sera produced gels with greater vertical 17 and/or horizontal 16 distances of the spur from the location of β-macroglobulin 10 have more severe case of the disease than those with lesser distances. The comparison showed the following: FIG. 6 (most severe case of AIDS), FIG. 7, FIG. 8 and FIG. 9 (least severe case of AIDS). This is an example of the application of the first analysis. One skilled in the art will realize that the baseline can be another position that is standardized for all the gel photographs, and the relative distances can be measured from another point that is located in the spread of the serum, as long as these points are consistent for all the photographs being compared and consistently used to measure the relative distances. Other variations that do not depart from the spirit of the first analysis can be used.

Figure 10:
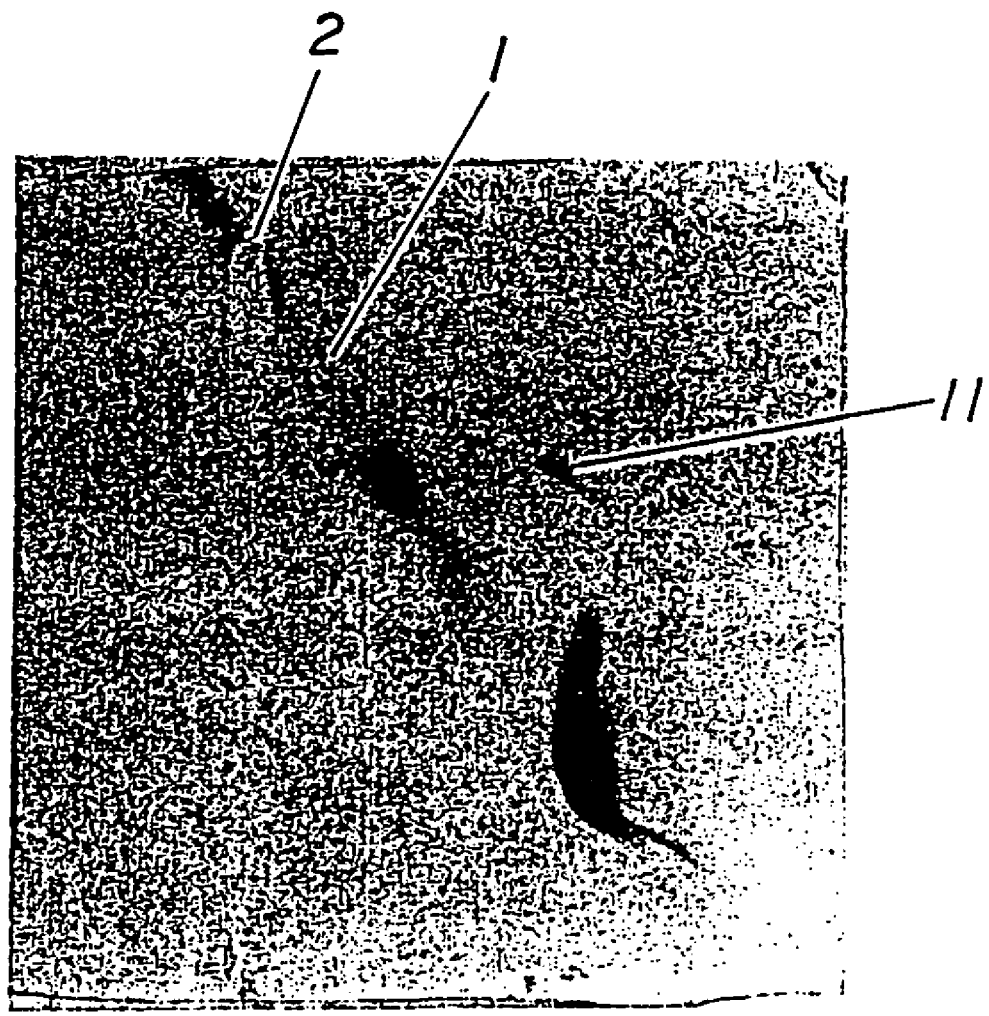

FIG. 10 is significant in that at the time the serum for this test was taken, the subject tested HIV-negative on the ELISA. However, the test of the present invention indicated that the subject was HIV-positive as shown by broken precipitation spur 11. Two months after the serum for the test was drawn, the subject tested HIV-positive on the ELISA. Thus, the figure confirms that the test of the present invention is capable of an earlier detection of HIV infection than the conventional ELISA.

Figure 11:
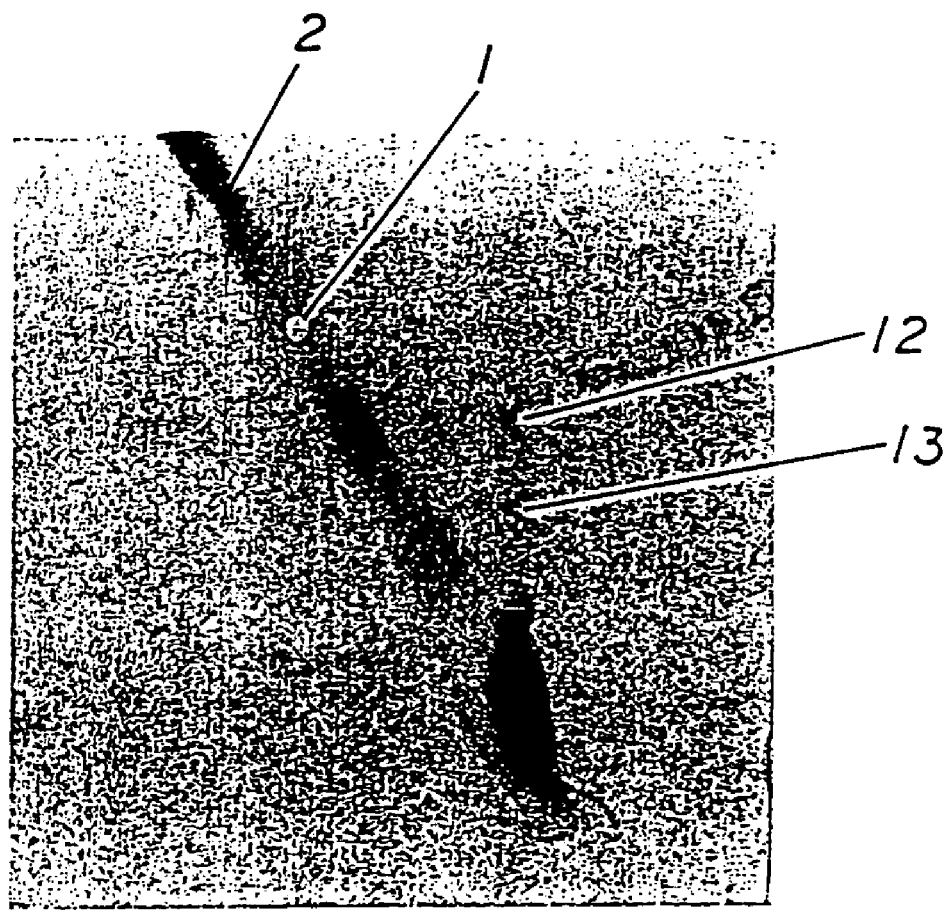

FIG. 11 is significant in that the serum sample was taken after a clinically diagnosed AIDS subject had been transfused with blood from a healthy donor. The precipitation spur caused by the donor's serum is indicated by the arrow 12 at the location of higher molecular weight, which tends to show that the initial small amount of fragmentation of whole aTF from the healthy donor, and thus the location of the spur was closer to the molecular weight expected of a healthy subject and more indicative of an earlier stage of infection, as shown by the relatively similar locations of this spur with the spur in FIG. 10. The precipitation spur caused by the serum of the AIDS subject is indicated by the arrow 13, at a location of lower molecular weight, which indicates fragmented and thus smaller aTF from the patient and HIV-infection.

The two-dimensional gel electrophoresis shown herein can be mass-produced as an in vitro device for testing of biological fluid samples for the presence of HIV infection from the test subjects. The gels can be dried for easy packaging and transportation. The packaged gel may contain a preformed well for samples, and a trough for TF. The TF can be stored in a container and sold separately or together with the gel as a kit. Additionally, the kit may also contain containers for the electrophoretic buffer, the stains and/or molecular weight standards. For the control, the kit may further contain containers with serum samples) from healthy subject(s).

Besides the above specified assay, included in the present invention are variations of the above assay and any assay which allows for the determination of the precipitation pattern of a subject's biological fluid sample with aTF, preferably in relation to β-, $α_1$-, and $α_2$ macroglobulins. Kits, containing reagents and materials needed for these assays are also included in the present invention.

EXAMPLE 3

This example describes a study in which an AIDS patient (also referred to as "test subject" in this EXAMPLE 3) was therapeutically treated with the TF composition of the present invention. The patient did not receive any other treatments or drugs during the study.

The patient was a 27 year old White homosexual male, weighing 138 pounds at the beginning of the trial. Eighteen months ago, the, patient's serum tested positive for HIV antibodies. The patient was also diagnosed as HIV positive based on his clinical symptoms, p24 antigen count, $CD4^+$ and $CD8^+$ on cell counts in absolute numbers (cells/μl) and lymphocyte subset percentages, as shown in TABLE 1 below for the tests conducted on the patient's blood sample taken on Apr. 12, 1995, two weeks before he started his TF treatment. The patient was not suffering from AIDS before and during the TF treatment.

The treatment started on Apr. 27, 1995. The patient received 14 mg of TF per week in two intramuscular injections, one injection on Tuesday and another on Wednesday. Each injection contained 7 mg of TF (in 2 ml of a formulation containing 3.5 mg/ml of TF). The TF was purified as described in Example 1 above and the sterilized TF formulation contained: 3.5 mg/ml methylated TF, 8.1 mg/ml sodium chloride, 1.9 mg/ml sodium acetate, 2.6 mg/ml sodium triphosphate, 2.1 mg/ml aluminum chloride, pH 6.2.

TABLE 1 presents the results of the experiment. The dates are the dates on which blood samples were taken from the patient. The tests were conducted by Unilab Corporation (Tarzana, Calif.), using generally accepted clinical assays.

TABLE 1

| TEST NAME | SAMPLE DATE | | | | | |
|---|---|---|---|---|---|---|
| | Apr. 12, 1995 | Apr. 27, 1995 | May 64, 1995 | May 11, 1995 | May 18, 1995 | May 24, 1995 |
| RBC | 4.94 | 4.62 | 4.77 | 4.85 | 4.79 | 4.66 |
| HEMOGLOBIN | 15.3 | 16.6 | 14.5 | 15.5 | 14.8 | 14.7 |
| PLATELET COUNT | 233 | 221 | 236 | 206 | 186 | 208 |
| WBC | 4.3 | 4.5 | 6.2 | 6 | 5.7 | 5.5 |
| POLYS | 53 | 61 | 58 | 52 | 64 | 57 |
| LYMPHOCYTES | 32 | 27 | 33 | 24 | 26 | 27 |
| MONOCYTES | 12 | 10 | 7 | 12 | 8 | 10 |
| EOSINOPHILS | 2 | 1 | 1 | 11 | 2 | 4 |
| BASOPHILS | 1 | 1 | 1 | 1 | 0 | 2 |
| CD4 % | 33 | 32 | 25 | 31 | 31 | 33 |

TABLE 1-continued

| | SAMPLE DATE | | | | | |
|---|---|---|---|---|---|---|
| TEST NAME | Apr. 12, 1995 | Apr. 27, 1995 | May 64, 1995 | May 11, 1995 | May 18, 1995 | May 24, 1995 |
| CD4 ABS. | 468 | 397 | 531 | 446 | 459 | 498 |
| CD8 % | | | 52 | 56 | 52 | 56 |
| CD8 ABS. | | | 1108 | 806 | 979 | 848 |
| RATIO H/S | | | 0.47 | 0.6 | 0.6 | 0.6 |
| TOTAL PROT. | 7.7 | 7.4 | 7.6 | 8 | 7.3 | 7.2 |
| ALB. | 4.8; 62% | 3.8; 51.3 | 3.9; 51.3% | 4.3; 53.7% | 3.9; 53.3% | 3.6 |
| ALPHA-1 | | 0.1; 1.35% | 0.2; 2.63% | 0.2; 1.9% | 0.1; 1.7% | 0.1 |
| ALPHA-2 | | 0.7; 9.45% | 0.7; 9.21% | 0.8; 10.1% | 0.5; 7.3% | 0.7 |
| BETA | 2.9; 38% | 0.9; 12.5% | 0.9; 11.84% | 0.8; 10.0% | 0.8; 11.4% | 0.9 |
| GAMMA | | 1.9; 25.66% | 1.9; 25.00% | 1.9; 24.3% | 1.9; 26.3% | 1.9 |
| P/24 | POSITIVE | POSITIVE | NOT TESTED | NEGATIVE | NEGATIVE | ,NEGATIVE |

The tests are as follows:

"RBC" and "WBC" denotes red and white blood cell counts, respectively ($\times 10^3/mm^3$).

"HEMOGLOBIN" and "PLATELET COUNT" denote the haemoglobin counts (in g/dL) and platelets counts ($\times 10^3/mm^3$), respectively.

"POLYS" denotes neutrophil cell counts measured, as a percentage of white blood cell counts.

The "LYMPHOCYTES", "MONOCYTES", "EOSINOPHILS", and "BASOPHILS" counts were each measured as a percentage of white blood cell counts. The above complete blood counts were determined using hematology analyzer.

"CD4%" and "CD8%" denote the lymphocyte subset percentages of $CD4^+$ and $CD8^+$ cells, respectively. "CD4 ABS" and "CD8 ABS" denote the absolute cell numbers (in cells/µl) of $CD4^+$ and $CD8^+$ cells, respectively. The $CD4^+$ and $CD8^+$ cell counts were determined by flow cytometry.

"RATIO H/S" denotes the ratio of the Helper versus the Suppressor cells and was obtained by dividing the number of "CD4 ABS" With the number for "CD8 ABS".

"TOTAL PROT." denotes the total blood serum protein in g/dL in the patient's sample, as determined by colorimetric method using Olympus AU 5000 instrument (Olympus Co., Ltd., Tokyo, Japan).

"ALB." denotes albumin "ALPHA-1" denotes alpha-1 globulin; "ALPHA-2" denotes alpha-2 globulin; "BETA" denotes beta-globulin "GAMMA" denotes gamma-globulin. These serum proteins were determined by serum protein electrophoresis. For each column of a specific serum protein, the number to the left is in g/dL, and the number to the right indicates the percentage distribution of the specific serum globulin among all the serum globulins.

"P/24" denotes p24 viral core antigen which was determined by p24 antigen EIA test kit (Abbott Laboratories, Abbott Park, Ill.).

Further, the blood samples collected on the time points specified in TABLE 1 also tested positive for HIV-1 antibodies as determined by HIV ELISA test kit of Organon Technica (Raleigh, N.C.). The patient gained 7 pounds in weight between his first TF injection and up to May 24, 1995.

The above tests show a trend of increasing $CD4^+$ cell counts and decreasing $CD8^+$ cell counts after the start of the TF treatment. Additionally, the p24 antigen tests showed negative results after the start of the TF treatment, though the test subject tested positive before and at the start of the TF treatment. The HIV antibody assays remained positive as residual antibodies remained in the test subject. These test results tend to suggest that the TF treatment was effective in combating HIV-infection and the progression of the disease caused by HIV.

In addition to the above tests conducted by Unilab Corporation, applicant also conducted the HIV diagnostic tests, two-dimensional electrophoresis, described in EXAMPLE 2, above, on the serum samples collected at the time points stated in TABLE 1.

Figure 13:
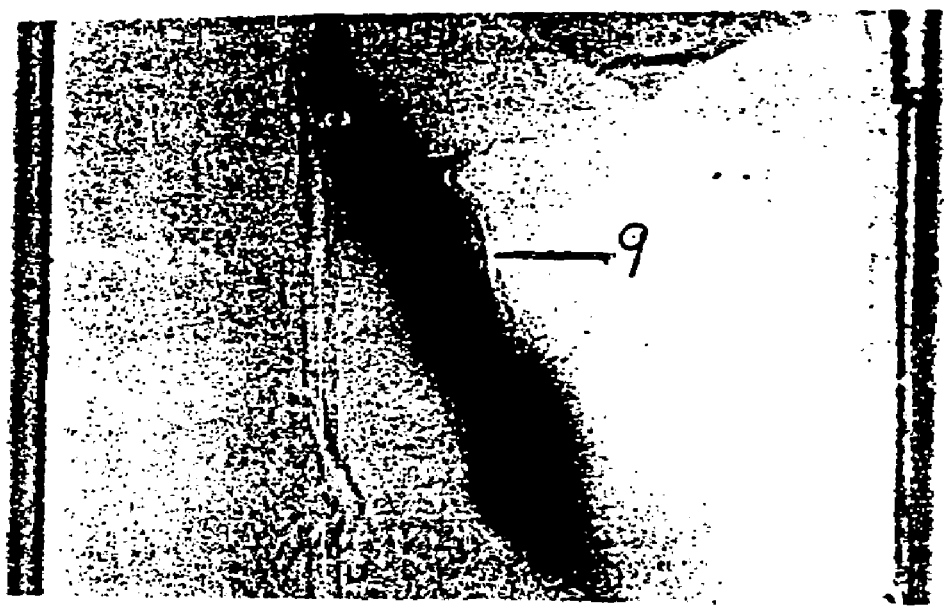
FIG. 13 is a photograph of a two-dimensional electrophoretic gel showing the precipitation pattern of TF with a serum sample from an HIV-negative human subject.
Figure 14:
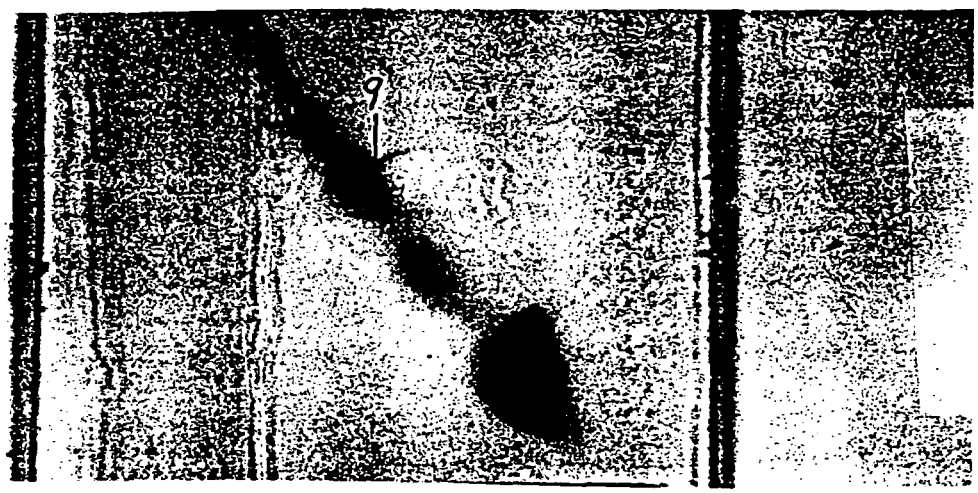
FIG. 14 is a photograph of a two-dimensional electrophoretic gel showing the precipitation pattern of TF with a serum sample from an HIV-positive human subject.

FIGS. 13 and 14 are photographs of two-dimensional electrophoretic gels of serum samples from two controls: a human subject whose serum sample tested negative for HIV antibodies in the ELISA test of Organon Technica, and a human subject whose serum sample tested positive in the same ELISA test. It can be seen that in FIG. 13, the precipitation spur 9 is a continuous spur spanning alongside the lotions of $\beta$-, $\alpha_1$-, and $\alpha_2$-macroglobulins, which indicate a healthy HIV negative subject. In contrast, the precipitation spur 9 in FIG. 14 is discontinuous, indicating HIV infection in the subject.

FIGS. 15 to 19 present the resulting photographs of the two-dimensional electrophoretic gel tests for the test subject, on the serum samples collected on May 11, May 18, May 24 and May 31, 1995, respectively.

Figure 15:
FIG. 15 is a photograph of a two-dimensional electrophoretic gel of the serum sample collected on May 4, 1995 from the test subject of Example 3.

As shown in FIG. 15, after a week of receiving the above TF treatment, on May 4, 1995 the test subject's serum sample tested negative for HIV infection, as indicated by the continuous precipitation spur 9 alongside the locations of $\beta$-, $\alpha_1$-, and $\alpha_2$-macroglobulins.

Figure 16:
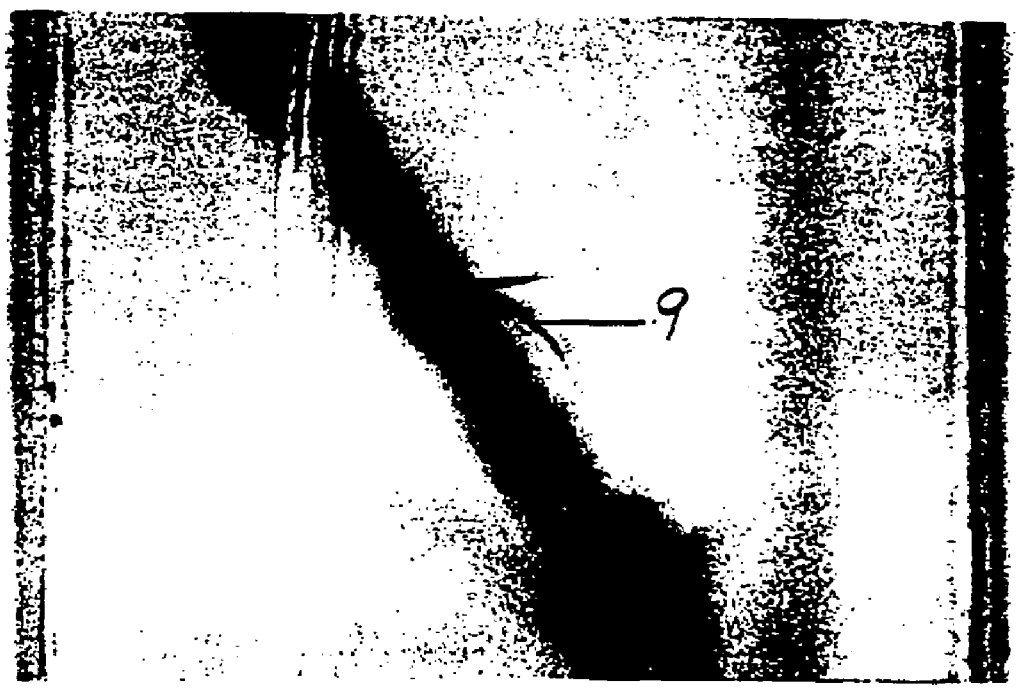
FIG. 16 is a photograph of a two-dimensional electrophoretic gel of the serum sample collected on May 11, 1995 from the test subject of Example 3.

As shown in FIG. 16, in the second week of treatment, on May 11, 1995, the test subject's serum formed a continuous precipitation spur 9 alongside the locations of $\beta$-, and $\alpha_1$, -macroglobulins, which is a more continuous precipitate spur than that observed for the control HIV-positive patient of FIG. 14.

Figure 17:
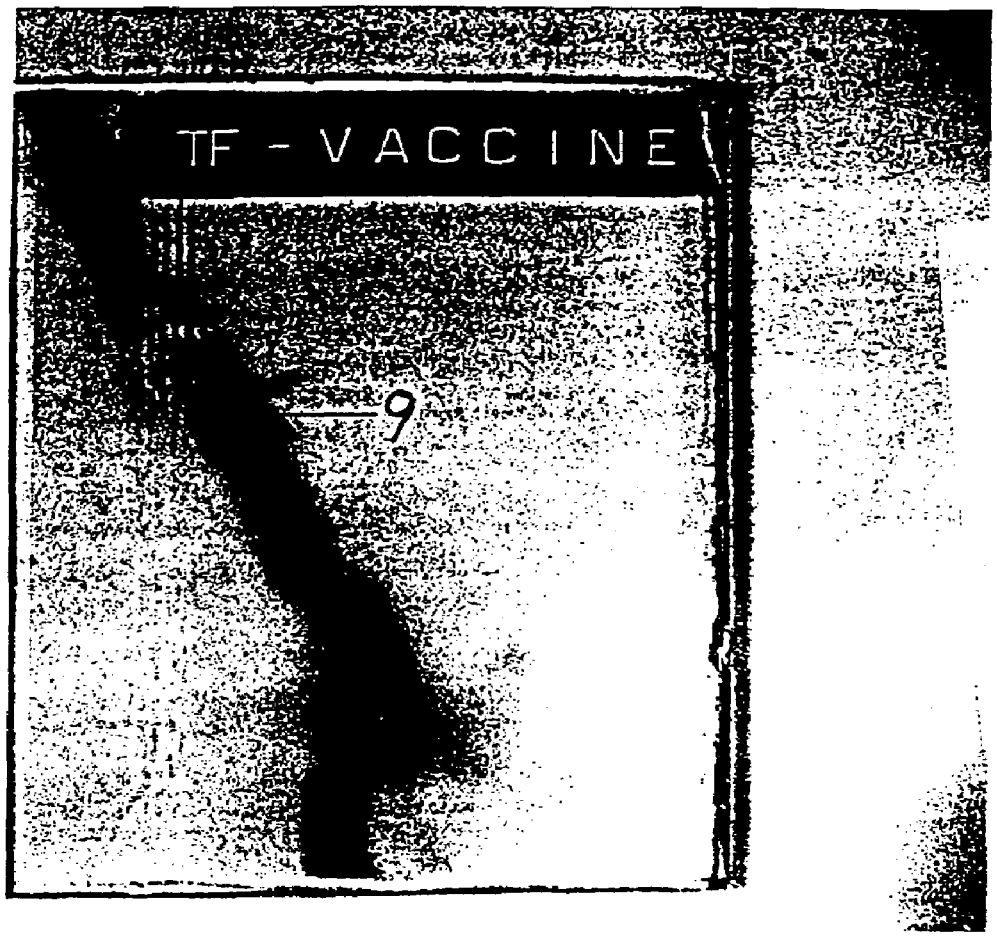
FIG. 17 is a photograph of a two-dimensional electrophoretic gel of the serum sample collected on May 18, 1995 from the test subject of Example 3.
Figure 18:
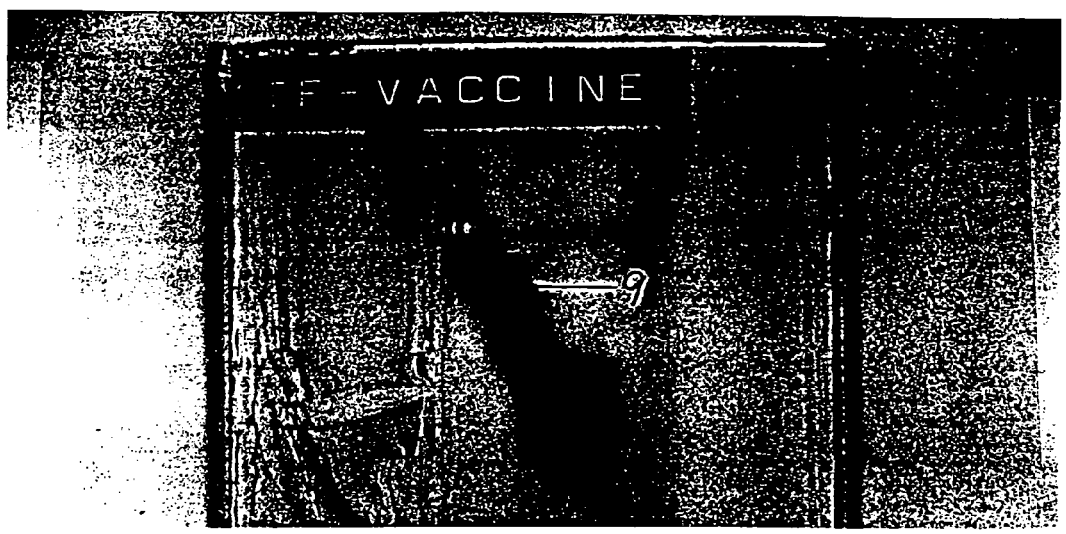
FIG. 18 is a photograph of a two-dimensional electrophoretic gel of the serum sample collected on May 24, 1995 from the test subject of Example 3.
Figure 19:
FIG. 19 is a photograph of a two-dimensional electrophoretic gel of the serum sample collected on May 31, 1995 from the test subject of Example 3.

As shown in FIGS. 17 and 18, in the third and fourth weeks of treatment, on May 18 and 24, 1995, the test subject's serum formed a less continuous precipitation spur 9. However, in the fifth week, on May 31, 1995, a continuous precipitation spur 9 is again observed alongside the locations of $\beta$-, $\alpha_1$-, and $\alpha_2$-macroglobulins (as shown in FIG. 19), indicating HIV-negative status. The two-dimensional electrophoretic tests tend to suggest that the TF treatments of the present invention is effective against HIV-infection and/or disease progression.

EXAMPLE 4

This Example provides further data regarding six human patients who were therapeutically treated with the TF composition of the present invention. These patients did not receive any other treatments or drugs during and after the six weeks of treatment period. The TABLES below also show patients' data at nine months (for Patient Nos. 1-5), and two months (for Patient No. 6) after the end of the treatment period.

For six consecutive weeks, each patient received 14 mg of TF per week in two intramuscular (IM) injections, one injection on Tuesday and another on Wednesday per week. Each injection contained 7 mg of TF (in 2 ml of a formulation containing 3.5 mg/ml of TF). The TF was purified as described in EXAMPLE 1 above and the sterilized TF formulation contained: 3.5 mg/ml methylated TF, 8.1 mg/ml sodium chloride, 1.9 mg/ml sodium acetate, 2.6 mg/ml sodium tri-phosphate, 2.1 mg/ml aluminum chloride, pH 6.2.

TABLES 2 to 7 present the results of the study for each patient. The tests were conducted by laboratories using generally accepted clinical assays. In the TABLES, "HIV-Ab, ELISA" denotes HIV-1 antibodies as determined by ELISA. "CD4 abs." and "CD8 abs." denote the absolute cell numbers (in cells/µl) of CD4 and CD8 cells, respectively. "p24 Ag" denotes p24 viral core antigen which was determined by p24 antigen immune complex disruption (ICD) EIA; this EIA for HIV-1 antigen detects p24 core protein after disruption of immune complexes. "HIV-1 RNA, PCR" denotes quantitative estimate of number of copies of HIV-1 ribonucleic acid (RNA) per ml of plasma tested by polymerase chain reaction (PCR) amplification. Increases/decreases in the number of copies of viral RNA detected are associated with increases/decreases in plasma viremia. "HIV-1 Plasma Culture" denotes HIV-1 titers found in plasma and peripheral blood mononuclear cell cultures. "HIV-1 Plasma Quantitative" denotes HIV-1 viral infectivity expressed as infectious unit per ml (IU/ml). "Poly Cells" denotes white blood cell counts in absolute numbers (cells/µl). The α-1 macroglobulin (denoted as "alpha-1 Macro"), α-2 macroglobulin (denoted as "alpha-2 Macro"), and gamma-immunoglobulin ("IgG") were determined by serum protein electrophoresis. The number (with %) indicated is the percentage distribution of the specific serum globulin among all the serum globulins. In TABLE 7 "IgA" and "IgM" denote immunoglobulins A and M, respectively. In TABLE 7, the IgG, IgA and IgM are expressed in mg/DL serum. "HLA-DR" denotes a product of Human Major Histocompatibility complex located on chromosome 6.

Further definitions as used in TABLES 2-7 are:

inc. normal level for a healthy person:

pos. positive;

+ positive, increased positive level is denoted by additional "+";

neg. negative;

– not tested;

nt not tested;

× multiple of the normal level for a healthy person, e.g., "2×" denotes twice the normal level.

The following describes in detail the conditions of each patients.

Patient No. 1

The following TABLE 2 summarizes the results of clinical tests conducted on Patient No. 1.

At the start of treatment, Patient No. 1 (a 21-year old female) had full blown AIDS with cerebral damage and mental disorders, a CD4 count of 36, and a life expectancy in the range of six-twelve months. Her CD4 count increased from 36 (at the start of treatment) to 108 (nine months after the end of the treatment period). Beginning in the fourth week of treatment, the p24 core antigen was negative, i.e., at less that 5 µg/ml. This negative p24 core antigen reading indicates lack of viral activity as of the fourth week of treatment. The plasma HIV-1 culture tested negative as of the fourth month of treatment. The negative plasma HIV-culture reading indicates that this patient's T-cells isolated from plasma were non-infective when mixed with T-cells of uninfected control blood in the in vitro assay—i.e. negative plasma culture. In contrast, positive plasma culture was produced when T-cells from control HIV-1 infected blood were mixed with uninfected control blood in the in vitro assay. Increases in IgG, α-1 and α-2 macroglobulin activities were observed during and after TF treatment. Nine months after treatment, the patient no longer had full blown AIDS (e.g., no opportunistic diseases), though she was still HIV positive (i.e., tested positive for antibodies against HIV in an ELISA).

TABLE 2

Patient #1. HUMAN CLINICAL AND LABORATORY TEST RESULTS

| Test Performed | Pre-Treatment | Results during treatment i.m. Injection two x/week | | | Post Treatment results No other Treatment - Months | | | | | | |
|---|---|---|---|---|---|---|---|---|---|---|---|
| | | 2 | 4 | 6 | 1 | 2 | 4 | 5 | 6 | 7 | 9 |
| HIV-Ab, ELISA | + | ++ | +++ | +++ | — | — | ++++ | ++++ | — | — | ++++ |
| CD4 abs. | 36 | 23 | 34 | 49 | — | — | 53 | 61 | — | — | 108 |
| CD8 abs. | 672 | 237 | 775 | 539 | — | — | 1209 | 1162 | — | — | 983 |
| P24 Ag | pos. | pos. | neg. | neg. | — | — | neg. | neg. | — | — | neg. |
| HIV-1 RNA, PCR copies per ml. | 88200 | — | — | 17300 | — | — | 11900 | — | — | — | 6500 |
| HIV-1 Plasma Culture | pos. | — | — | neg. | — | — | neg. | — | — | — | neg. |
| HIV-1 Culture Quantitative | — | — | — | — | — | — | — | — | — | — | — |
| Poly Cells × 10³ | 2.23 | 2.8 | 4.76 | 57 | — | — | 6.6 | 6.4 | — | — | 6.9 |
| alpha-1 Macro | 1.35 | 1.24% | 2.66% | 2.70% | — | — | 2.70% | 2.70 | — | — | 1.9% |
| alpha-2 Macro | 8.12 | 7.91% | 5.22% | 11.1% | — | — | 9.30% | 8.80% | — | — | 8.80% |
| IgG | 14.20% | 23.60% | 25.00% | 26.2% | — | — | 26.00% | 25.20% | — | — | 22.00% |
| Delta/gamma chain | | 2x | 2x | 1.5x | — | — | inc. | inc. | — | — | inc. |
| HLA-DR | | 2x | 2x | 2x | — | — | inc. | inc. | — | — | inc. |

Patient No. 2

The following TABLE 3 summarizes the results of clinical tests conducted on Patient No. 2. At the start of the treatment, Patient No. 2 (a 30-year old male) was HIV positive (i.e., tested positive for antibodies against HIV in an ELISA), however he did not suffer from all the symptoms of AIDS. His CD4 cell counts increased from 193 (before TF treatment) to 305 (nine months from the end of treatment). His p24 core antigen remained negative before, during and after TF treatment—indicating low viral activity. His plasma culture was converted to negative at fourth month after treatment, indicating non-infectivity of the his plasma in the in vitro assay. Increase in his humoral immunity was indicated by increases in the IgG, α-1 and α-2 macroglobulin levels. At nine months after the end of the treatment, the patient still did not show any sign of AIDS.

ment). Her p24 core antigen test was negative throughout the study. Her plasma culture converted to negative at fourth month after treatment. The increase in humoral immunity of the patient was indicated by increases in her IgG, α-1 and α-2 macroglobulins. Nine months after the end of the treatment, the patient did not show any sign of AIDS.

TABLE 3

Patient #2. HUMAN CLINICAL AND LABORATORY TEST RESULTS

| Test Performed | Pre-Treatment | Results during treatment i.m. Injection two x/week | | | Post Treatment results No other Treatment - Months | | | | | | |
|---|---|---|---|---|---|---|---|---|---|---|---|
| | | 2 | 4 | 6 | 1 | 2 | 4 | 5 | 6 | 7 | 9 |
| HIV-Ab, ELISA | ++ | +++ | +++ | +++ | — | — | +++ | ++++ | — | — | ++++ |
| CD4 abs. | 193 | 50 | 144 | 173 | — | — | 193 | 288 | — | — | 305 |
| CD8 abs. | 1348 | 298 | 755 | 840 | — | — | 1533 | 1312 | — | — | 1291 |
| P24 Ag | neg. | neg. | neg. | neg. | — | — | neg. | neg. | — | — | neg. |
| HIV-1 RNA, PCR copies per ml. | 43200 | — | — | 21100 | — | — | 9000 | — | — | — | 7000 |
| HIV-1 Plasma Culture | pos. | — | — | neg. | — | — | neg. | — | — | — | neg. |
| HIV-1 Culture Quantitative | — | — | — | — | — | — | — | — | — | — | — |
| Poly Cells × $10^3$ | 4.9 | 3.8 | 6.1 | 6.2 | — | — | 6.8 | 6.9 | — | — | 6.1 |
| alpha-1 Macro | 1.37% | 1.4% | 2.4% | 2.5% | — | — | 2.5% | 2.3% | — | — | 2.1% |
| alpha-2 Macro | 2.7% | 4.2% | 8.4% | 8.7% | — | — | 8.8% | 8.3% | — | — | 8.5% |
| IgG | 13.0% | 13.5% | 15.0% | 17.0% | — | — | 20.0% | 18.0% | — | — | 18.8% |
| delta/gamma chain | | 1.5x | 1.4x | 1.5x | — | — | inc. | Inc. | — | — | inc. |
| HLA-DR | | 1.2x | 1.2x | 2x | — | — | inc. | Inc. | — | — | inc. |

TABLE 4

Patient #3. HUMAN CLINICAL AND LABORATORY TEST RESULTS

| Test Performed | Pre-Treatment | Results during treatment i.m. Injection two x/week | | | Post Treatment results No other Treatment - Months | | | | | | |
|---|---|---|---|---|---|---|---|---|---|---|---|
| | | 2 | 4 | 6 | 1 | 2 | 4 | 5 | 6 | 7 | 9 |
| HIV-Ab, ELISA | ++ | ++ | +++ | +++ | — | — | +++ | +++ | — | — | +++ |
| CD4 abs. | 404 | 217 | 538 | 375 | — | — | 446 | 580 | — | — | 636 |
| CD8 abs. | 1544 | 1054 | 1587 | 898 | — | — | 1496 | 1381 | — | — | 1191 |
| P24 Ag | neg. | neg. | neg. | neg. | — | — | neg. | neg. | — | — | neg. |
| HIV-1 RNA, PCR copies per ml. | 51210 | — | — | 14240 | — | — | — | — | — | — | 8840 |
| HIV-1 Plasma Culture | pos. | — | — | neg. | — | — | neg. | — | — | — | neg. |
| HIV-1 Culture Quantitative | — | — | — | — | — | — | — | — | — | — | — |
| Poly Cells × $10^3$ | 3.7 | 2.9 | 5.1 | 6.9 | — | — | 6.8 | 6.6 | — | — | 6.7 |
| IgC | 12.24% | 14.4% | 17.7% | 21.0% | — | — | 19.8% | 18.01% | — | — | 18.0% |
| alpha-1 Macro | 1.2% | 1.4% | 2.6% | 2.7% | — | — | 2.7% | 2.4% | — | — | 2.4% |
| alpha-2 Macro | 4.1% | 4.1% | 5.3% | 8.3% | — | — | 8.1% | 8.2% | — | — | 8.2% |
| delta/gamma chain | | 1.2x | 1.4x | inc. | — | — | inc. | inc. | — | — | inc. |
| HLA-DR | | 1.8x | 1.4x | 1.2x | — | — | inc. | inc. | — | — | inc. |

Patient No. 3

The following TABLE 4 summarizes the results of clinical tests conducted on Patient No. 3.

At the start of the treatment, Patient No. 3 (a 24-year old female) was HIV positive (i.e., tested positive for antibodies against HIV in an ELISA), however she did not suffer from all the symptoms of AIDS. CD4 cell counts increased from 404 (pretreatment) to 636 (nine months from the end of treat- Patient No. 4

The following TABLE 5 summarizes the results of clinical tests conducted on Patient No. 4.

Before treatment, the patient (a 27-year old male) was HIV positive (i.e., tested positive for anitbodies against HIV in an ELISA), and had full blown AIDS symptoms (Grade 3, with opportunistic infections in the throat and upper part of the lung). His CD4 cell counts increased from 389 (before treatment) to 599 (nine months from the end of treatment). His p24 core antigen converted to negative after four weeks of treatment and remained negative. His HIV plasma infectivity was converted to non-infective after six weeks of treatment and remained non-infective. The increased in humoral immunity of the patient was indicated by the increase in his IgG, α-1 and α-2 macroglobulins. Twelve months after the end of the treatment, the patient did not show any sign of AIDS.

blood in the excrement. However, he did not have full blown AIDS. His CD4 cell count remained constant after treatment. His p24 core antigen was converted to negative during the fourth week of treatment and remained so by seven months after treatment. The HIV-1, RNA, PCR showed that the number of viral copies had been maintained at about 6,000-7,000 copies/ml. His plasma culture was non-infective after treat-

TABLE 5

Patient #4. HUMAN CLINICAL AND LABORATORY TEST RESULTS

| Test Performed | Pre-Treatment | Results during treatment i.m. Injection two x/week | | | Post Treatment results No other Treatment - Months | | | | | | |
|---|---|---|---|---|---|---|---|---|---|---|---|
| | | 2 | 4 | 6 | 1 | 2 | 4 | 5 | 6 | 7 | 9 |
| HIV-Ab, ELISA | + | ++ | +++ | +++ | — | — | ++++ | ++++ | — | — | ++++ |
| CD4 abs. | 389 | 322 | 507 | 394 | — | — | 393 | 573 | — | — | 599 |
| CD8 abs. | 850 | 752 | 839 | 540 | — | — | 563 | 607 | — | — | 802 |
| P24 Ag | pos. | pos. | neg. | neg. | — | — | neg. | neg. | — | — | neg. |
| HIV-1 RNA, PCR copies per ml. | 116000 | — | — | 30000 | — | — | — | — | — | — | 6600 |
| HIV-1 Plasma Culture | pos. | pos. | — | neg. | — | — | neg. | — | — | — | neg. |
| HIV-1 Culture Quantitative | — | — | — | — | — | — | — | — | — | — | — |
| Poly Cells × $10^3$ | 4.3 | 3.8 | 6.3 | 6.7 | — | — | 6.6 | 6.3 | — | — | 6.4 |
| alpha-1 Macro | 1.7% | 1.8% | 4.0% | 4.4% | — | — | 3.3% | 2.4% | — | — | 1.6% |
| alpha-2 Macro | 9.1% | 9.0% | 7.8% | 10.2% | — | — | 10.2% | 9.8% | — | — | 10.1% |
| IgC | 14.8% | 12.6% | 23.0% | 23.0% | — | — | 19.8% | 21.0% | — | — | 19.3% |
| Delta/gamma chain | | 2x | 2x | 1.5x | — | — | inc. | inc. | — | — | inc. |
| HLA-DR | | 2x | 2x | 2x | — | — | inc. | inc. | — | — | inc. | ment. His immune system produced increased of IgG, α-1 and α-2 macroglobulin. He had gained 10-12 pounds of weight. Ten months after the end of the treatment, he did not show any sign of AIDS.

TABLE 6

Patient #5. HUMAN CLINICAL AND LABORATORY TEST RESULTS

| Test Performed | Pre-Treatment | Results during treatment i.m. Injection two x/week | | | Post Treatment results No other Treatment - Months | | | | | | |
|---|---|---|---|---|---|---|---|---|---|---|---|
| | | 2 | 4 | 6 | 1 | 2 | 4 | 5 | 6 | 7 | 9 |
| HIV-Ab, | + | + | ++ | +++ | ++++ | ++++ | ++++ | ++++ | ++++ | ++++ | ++++ |
| CD4 abs. | 528 | 531 | 582 | 420 | 470 | 596 | 434 | 415 | 438 | 438 | 669 |
| CD8 abs. | nt | 1108 | 979 | 803 | 818 | 1220 | 1004 | 1150 | 926 | 909 | 890 |
| P24 Ag | pos. | pos. | neg. | neg. | neg. | neg. | neg. | neg. | neg. | neg. | neg. |
| HIV-1 RNA, PCR copies per ml, | 70000 | — | — | — | 7870 | 30928 | — | — | — | 6317 | — |
| HIV-1 Plasma Culture | pos. | pos. | pos. | neg. | neg. | neg. | neg. | neg. | neg. | neg. | neg. |
| HIV-1 Culture Quantitative | nt | nt | — | — | nt | nt | nt | nt | nt | nt | nt |
| Poly Cells × $10^3$ | 4.3 | 6.2 | 5.7 | 5.9 | 6.0 | 5.9 | 7.3 | 6.5 | 5.6 | 5.8 | 6.0 |
| alpha-1 Macro | 1.3% | 2.6% | 1.9% | 2.0% | 2.8% | 2.6% | 2.1% | 2.4% | 2.4% | 2.4% | 2.4% |
| alpha-2 Macro | 9.4% | 9.2% | 7.3% | 8.0% | 10.3% | — | 10.1% | 11.8% | 11.0% | — | 11.2% |
| IgC | 18.6% | 25.0% | 26.3% | 25.1% | 24.7% | — | 24.6% | 23.9% | 22.8% | — | 23.3% |
| Delta/gamma chain | | 1.2x | 1.6x | 2.0x | 1.5x | — | — | — | inc. | — | inc. |
| HLA-DR | | 1.2x | 1.8x | 2.0x | 2.0x | — | — | — | 1.2x | — | inc. |

Patient No. 5

This patient is the same as the one in EXAMPLE 3, above. The following TABLE 6 summarizes the results of clinical tests conducted on Patient No. 5.

Before the treatment, the patient was HIV positive (i.e., tested positive for anitbodies against HIV in an ELISA), suffering from pneumonia, vomiting, and diarrhea without Patient No. 6

The following TABLE 7 summarizes the results of clinical tests conducted on Patient No. 6.

At the start of the treatment period, the patient had f full blown AIDS (at a grade between 3 and 4, suffering from e.g., retinitis, cytomegalovirus infection, fungal infection I in the throat, lung, trachea, and bronchi, and bedridden). His CD4 count was slightly increased after two months of treatment. His p24 core antigen converted to negative after four weeks of treatment and remained negative. His plasma culture was positive before treatment and was converted to negative and non-infective after treatment. Generally, the peripheral blood cell cultures are positive in a patient with CD4 count of less than 100 and viral loads of $5 \times 10^5$. However, in the case of Patient No. 6, no HIV was detected in the peripheral blood cells at one and two months of treatment. Significantly, the viral load of the patient had decreased from $5 \times 10^5$ to $3 \times 10^4$ copies of viral RNA. This is close to a 1.5 log decrease in viral RNA. Patient No. 6 had also gained 15 pounds of weight since the start of treatment. Three months after the end of treatment, the patient did not have AIDS.

TABLE 7

HUMAN CLINICAL AND LABORATORY TEST RESULTS
PATIENT NO. 6

| Test Preformed | Pretreatment | Treatment Period 1M Injection 2x/week | | | Post Treatment Results Time With No Other Treatment | | | | | | | |
|---|---|---|---|---|---|---|---|---|---|---|---|---|
| | | 2 weeks | 4 weeks | 6 weeks | 1 month | 2 month | 3 month | 4 month | 5 month | 6 month | 7 month | 9 month |
| HIV-Ab, ELISA | + | + | + | + | + | + | | | | | | |
| CD4 abs. | 70 | | | | 79 | | | | | | | |
| CD8 abs. | 624 | | | | 700 | | | | | | | |
| P24 Ag | + | + | neg | neg | neg | neg (<5 pg/ml) | | | | | | |
| HIV-1 Plasma Culture | + | nt | nt | nt | neg | neg | | | | | | |
| HIV-1 Culture Quantitative | nt | nt | nt | nt | neg | neg | | | | | | |
| HIV-1 RNA, PCR | $5 \times 10^5$ | nt | nt | nt | 30924 | 31795 | | | | | | |
| IgC | nt | nt | nt | nt | 1413 | 1323 | | | | | | |
| IgA | nt | nt | nt | nt | 768 | 802 | | | | | | |
| IgM | nt | nt | nt | nt | 218 | 244 | | | | | | | nt = not tested; neg = negative

Conclusion

This Example shows that HIV viral activity was stopped as seen by P24 core antigen converting to less that 5 µg/ml, the limit of test method. Dramatic increase of CD4 count in the HIV patient was also shown. This increase is more dramatic over time than those observed for antiviral products commercially available in the United States, such t as AZT and others. This Example also shows dramatic decreases in viral load of the patients as determined by quantitative RNA polymerase chain reaction. The patients' plasma cultures converted to negative. In in vitro systems, the patients' blood plasma was non-infective. The patients' T-cells were unable to infect non-infected (normal) patients' T-cells in vitro. The foregoing may indicate lack of virus in the plasma. It may also indicate the patient might have been immunized, and thus unable to infect other non-infected patients.

The peripheral blood mononucleocytes (PBMC) tested negative for HIV. The treatment transformed full blown AIDS patients to patients having undetectable HIV both in their plasma and peripheral blood cells. It appeared that both humoral and cellular immunity of the patient were utilized to destroy and neutralize the virus.

EXAMPLE 5

This example presents another method of purifying TF. In this example, TF is subject to high-performance liquid chromatography ("HPLC") purification. TF was prepared from calf thymus 4 hours after sacrifice. All the buffers and solutions used in this section were sterilized by filtration. If needed, the buffers were adjusted by 0.2 N Noah or 0.1 N HCl. All the chemicals, including the distilled water, for the preparation of the buffers and solutions were USP grade.

The thymus tissue and its associated connective tissues were separated from a calf within 4 hours of its sacrifice. The tissues were washed with a solution containing 0.14 M NaCl, and 0.005 M EDTA-$Na_3$ at 4° C. for 5 minutes. The wash solution was decanted and the tissues were washed a second time under the same conditions. After decantation of the wash solution, the tissues were weighed. The tissues were homogenized in 0.14 M NaCl, 0.005 M KCl, 0.005 M $MgCl_2$, 0.003 M $CaCl_2$, 0.15 M TRIS-HCl, pH 7.6, 0.25 M sucrose with a tissue homogenizer (Brinkman Polytron Homogenizes, Brinkman Instruments, Inc., Westbury, N.Y), at 4° C. and at an rpm and for the duration of time recommended by the manufacturer of the homogenizer for removal of cell nuclei. The ratio of the tissue to the buffer was 1:4 (weight/weight).

The tissue homogenate was then filtered through a gauze pad by vacuum. The filtrate was centrifuged at 1000 g at 4° C. for 90 minutes. The supernatant was discarded. The pellet was resuspended in 0.008 NaCl, 0.003 M $CaCl_2$, 0.003 M $MgCl_2$, 0.08 M $NaH_2PO_4$, 0.002 M TRIS-HCl, 0.25 M sucrose, pH 5.2. The ratio of the pellet to the buffer was 1:4 (weight/weight). The resuspension was homogenated in a beaker with a magnetic stirrer at 200 rpm, at 4° C. for 5 minutes. The homogenate was then centrifuged at 3500 g, at 4° C. for 60 minutes. The supernatant was discarded. The pellet was resuspended in 0.014 M NaCl, 0.001 M $CaCl_2$, 0.002 M $MgCl_2$, 0.001 M EDTA-$Na_3$, 0.002 M TRIS-HCl, 0.25 M sucrose, pH 4.2 at a ratio of pellet to buffer of 1:4 (weight/weight). The resuspension was homogenated in a beaker with a magnetic stirrer at 200 rpm, at 4° C. for 5 minutes. The homogenate was then centrifuged at 8000 g, at 4° C. for 60 minutes. The supernatant was discarded.

The pellet of thymus cell nuclei was resuspended in 0.05M $Na_3C_6H_5O_7$, 0.05M $CH_3COOH$, 0.1N HCl (pH 2.6-2.8). The suspension was homogenized at 3000 rpm, at 4° C. for 1 minute. Pepsin dissolved in 20 ml of the same buffer was added to the homogenate at a pepsin to pellet ratio of 1:310 (weight/weight of pellet before homogenization). The mixture was placed in a beaker with a magnetic stirrer at 45 rpm, at 4° C. for 12 hours under nitrogen atmosphere. The resulting mixture was then centrifuged at 12,000 g, at 4° C. for 60 minutes. The pellet was discarded. The supernatant was removed and precipitated with a saturated solution of $(NH_4)_2SO_4$. The mixture was then centrifuged at 1200 g, at 4° C. for 60 minutes The supernatant was discarded. The pellet was dissolved in a minimum quantity of 0.14M NaCl. The resulting solution was dialyzed.

Figure 20:
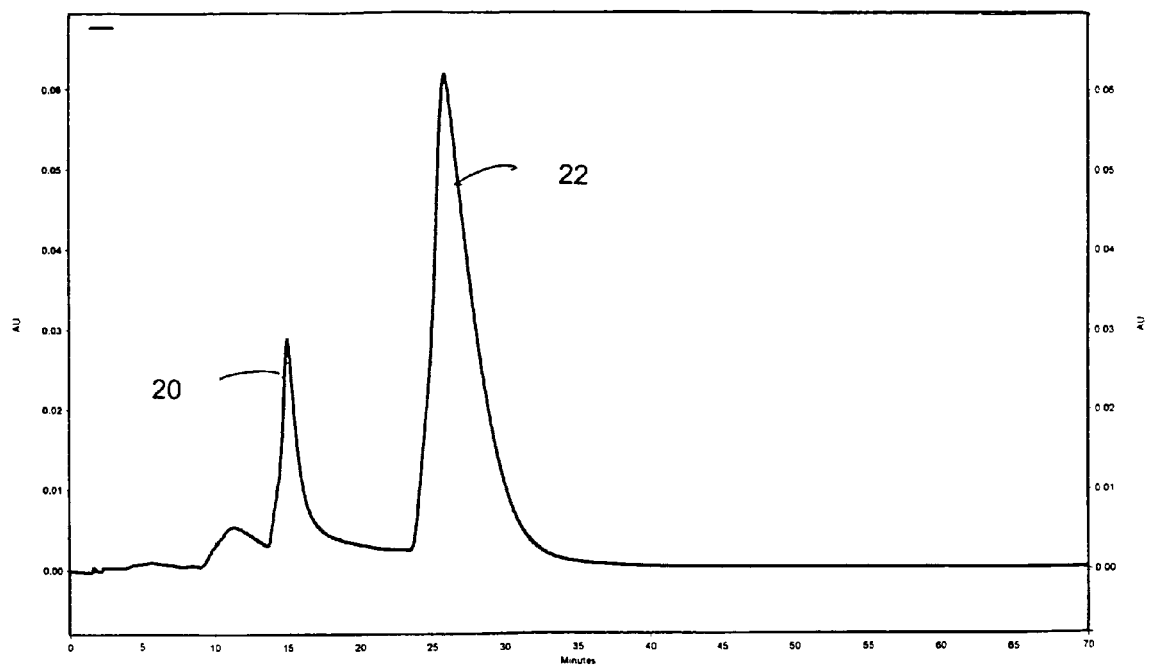
FIG. 20 is a high-performance liquid chromatography elution profile of a TF preparation.

After dialysis, the solution was centrifuged at 10,000 g (Beckman rotor) for 60 minutes at 4° C. to precipitate residual $(NH_4)_2SO_4$. The supernatant was then purified by gel filtration on Bio-gel P10 (Bio-Rad, Richmond, Calif.) or Sephadex G-50 gel (Pharmacia Uppsala, Sweden). Further purification was achieved by reversed phase high-performance liquid chromatography ("HPLC") on C-18 columns (RP Ultrasphere 10 mm Spherical 80A Preparative 21.2×150 mm). Buffer A was 1% acetonitrile diluted in sterile, HPLC-grade water; Buffer B was HPLC-grade methanol. The column was eluted with a linear gradient of 15%:85% BufferB:BufferA in 70 minutes. Detection was at 254 nm, with a flow rate of 0.850 m/min. and a solvent pH of 6.8. As shown in FIG. 20, the HPLC elution profile showed two peaks 20 and 22, which were isolated together. The final purification step involved sterile filtration with 0.45 µM filters (Nalgene).

i) Determination of Molecular Weight

The molecular weight of HPLC-purified TF was determined by silver stained 11% non-reducing SDS-PAGE as in Example 1. Two proteins, one with a molecular weight of about 12.5 Kd and the other with a molecular weight of about 14.5 Kd, were observed.

ii) Detecting and Diagnosing HIV-1 Infections

Human serum samples were provided by the AIDS Health Foundation, Los Angeles, Calif. as in EXAMPLE 2. The samples were tested for precipitation reactions with HPLC-purified TF using two-dimensional electrophoresis as in EXAMPLE 2 except that the trough for the second-dimension run was filled with HPLC-purifed TF. The results were essentially the same as for the carboxymethyl-purified TF in EXAMPLE 2.

With serum from an HIV-1 negative individual, a continuous precipitation spur similar to the precipitation spur of HIV-1 negative serum in EXAMPLE 2 was observed. The spur was positioned alongside $\alpha_2$-macroglobulin and $\beta$-macroglobulin. In contrast, sera from HIV-1 positive individuals gave rise to precipitation spurs that was less intense, non-continuous (broken) and/or no longer alongside either or both of $\alpha_2$-macroglobulin and $\beta$-macroglobulin. Sera from HIV-1 individuals with a PCR virus load of 10,000 gave broken precipitation spurs of two or more pieces. Sera from HIV-1 individuals with advanced AIDS (CD4 count less than 200) gave precipitation spurs that migrated closer to albumin in comparison with spurs from HIV-1 negative serum.

EXAMPLE 6

This example shows that TF can bind to fragment 579-601 of HIV-1 envelope protein gp41. Agarose rocket gel electrophoresis was performed. To prepare the agarose gel, 1 gram of agarose was heated in 100 ml of pH 7.6 electrophoresis buffer containing 2.42 g/l of Tris base, 1.2 ml of thiodiglycol per liter of buffer, 0.109 g/l of calcium lactate, 0.35 g/l of EDTA, 3.81 g/l of sodium tetraborate deca-hydrated, 3.75 g/l of glycine. Sample wells were loaded with HPLC-purified TF, gp41 fragment 579-601 (Sigma-Aldrich, St. Louis, Mo.), or various amounts of both proteins. The proteins were incubated at room temperature for 10 minutes before beginning electorphoresis. The gel was run at 165 V, 80 mA for 45 minutes. Following electrophoresis, the gel was fixed in ethanol:acetic acid (9:1), stained with 0.5% Brilliant blue R 250 in ethanol: acetic acid:water (4.5:1:5), then washed with 90% ethanol.

Figure 21:
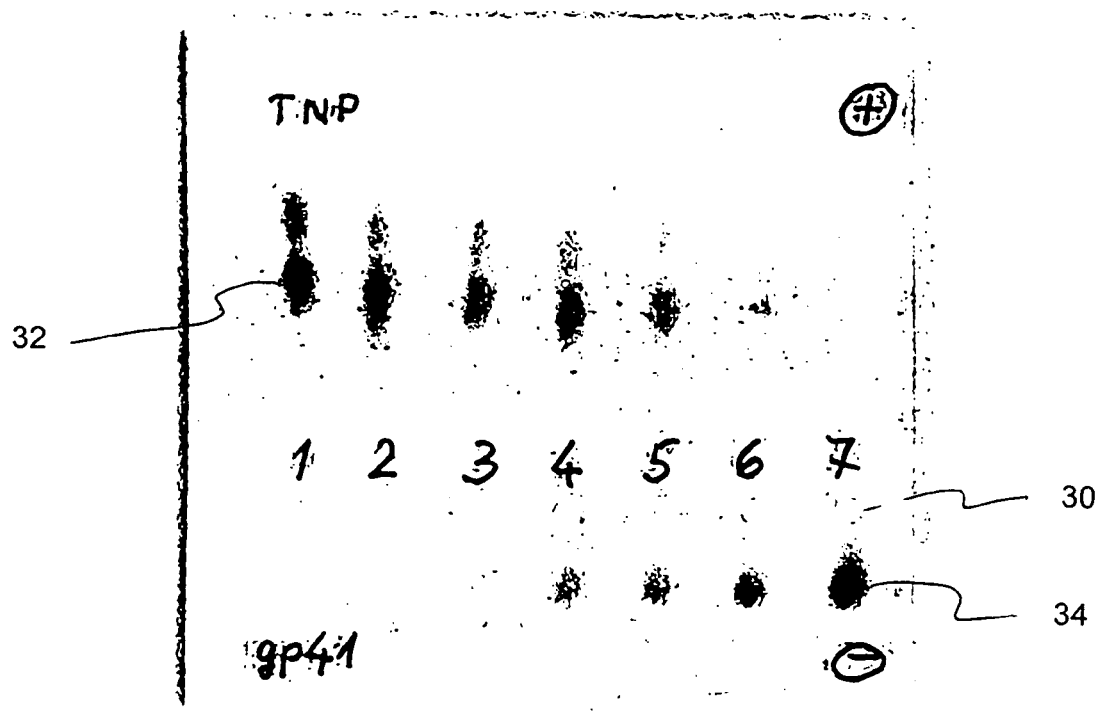
FIG. 21 is a photograph of a rocket electrophoresis gel with TF and fragment 579-601 of gp41 as samples.

FIG. 21 shows the results of the electrophoresis. Sample lanes are marked from 1-7. Sample well 30 demonstrates the location of the sample wells between the top and bottom of the gel. The sample of lane 1 contained only TF; the sample of lane 7 contained only fragment 579-601, and the samples of lanes 2-6 contained equal amounts of fragment 579-601 and decreasing amounts of TF from lane 2 to lane 6. As shown in FIG. 21, HPLC-purified TF and gp41 fragment 579-601 migrated in opposite directions when electrophoresed individually, with the TF protein band 32 migrating toward the cathode (lane 1) and the fragment 579-601 band 34 migrating toward the anode (lane 7). However, when TF was mixed with fragment 579-601, the gp41 fragment band diminished with increasing amounts of added TF. Mixing of gp41 with other proteins such as human and bovine $\alpha$ and $\beta$ lacto albumin, $\alpha_2$-macroglobulin, and chicken ovalbumen failed to produce similar results. These results indicate that TF binds to the gp41 fragment 579-601, altering the fragment's migration during electrophoresis.

EXAMPLE 7

This example provides the results of a clinical study conducted with eighteen patients in Bulgaria. The patients were treated with TF purified by carboxymethyl chromatography. TF was administered at 0.05 mg per kg body weight, bi-weekly for a total of eight weeks. This study was conducted in a single masked fashion with the study patients aware of their respective treatment received. However, the independent laboratory that generated the quantitative laboratory results was masked and was unaware of the patient treatment codes.

The patients were given a series of tests before and after the TF was administered. The tests performed were CD 4 counts, measurement of HIV-1 p24 core antigen levels, measurement of viral load by the polymerase chain reaction ("PCR"), and measurement of infectious virus by culture of peripheral blood mononuclear cells ("PBMC") and plasma. After completion of treatment, the patients were followed for eighteen months. Overall, the patients demonstrated no significant adverse effects of TF administration up to eighteen months post-treatment as judged by physical exam, subjective complaints, routine blood chemistries, and immunologic or virologic markers.

Each of the eighteen patients completed the full treatment course, with follow-up ranging from 50 to 667 days from the final injection (mean 335.3 days). Throughout the study, patients demonstrated no significant deleterious effects from the TF treatment as measured by clinical examination, subjective patient questioning, or routine blood chemistries.

As shown in the following TABLE 8, which summarizes the test results for the eighteen patients as a group, TF administration had little apparent effect on CD 4 cell counts, but HIV-1 infection status as measured by PCR and the number of infected PBMC was remarkably (and generally statistically significantly) improved. Indeed, by the fifth post-treatment visit (209-281 days after the final injection), the PCR score was reduced 86.5% from 89,125 RNA copies/ml at baseline to 12,023 (p=0.021), and the number of infected PBMC was reduced 89.0% from one in 34,674 cells to one in 316, 228 (p=0.006). The number of infectious units in plasma culture was also markedly reduced beginning with the third treatment visit (33-55 days after the first injection), but change from baseline never quite attained statistical significance for any visit. The proportion of patients with undetectable p24 antigen in their serum increased from 61.1% at baseline to 90% at post-treatment visit 5 (p=0.117), and p24 antibody was significantly increased for four patients by the second treatment visit (the only patients for whom this parameter was evaluated), persisting until the final visit at day 667 relative to the end of treatment.

Only one patient appeared to have experienced inadequate viral control after completion of TF therapy. For this patient, the number of infected PBMCs declined from 1 in 50.000 at baseline to 1 in 500,00/1,000.000 from treatment visit 2 through post-treatment visit 3, but at visit 5 (256 days after the last injection) had increased to 1 in 20.000. Similarly, over the same tune period. PCR values increased from 192,279 to 300,487 copies/ml.

TABLE 8

|  | CD4 count (% improvement) | p24 core antigen (% decrease) | PCR viral load (% decrease) | Infected PBMCs (% decrease) |
| --- | --- | --- | --- | --- |
| Treatment Group | No Decrease of CD4 Count | From 61% To 90% | 87% (p = 0.021)* | 89 p = 0.006* |

*Statistically Significant

Each patient was injected intramuscularly with 1.0 ml of a 2 mg/ml preparation of TF purified by carboxymethyl chromatography. Each patient received two injections per week, on two consecutive days, for a period of eight weeks, resulting in a total of sixteen intramuscular injections. During the treatment period, there were only transient superficial side effects which completely disappeared upon the completion of the dosing phase of the study.

The results of the study are summarized for each group in the following TABLE 9. For all groups, PCR viral loads of all patients showed dramatic decreases in HIV viral burden. Further, the decreased viral load correlated closely with viral infectivity as measured by PBMCs and by plasma culture assays. Of particular interest, all patients in all the treatment groups showed persistent HIV-1 viral suppression as measured by PCR or PBMC activity. The PCR scores were reduced by more than 90% and the PBMC scores were reduced by more than 90%, nine months after the cessation of all anti-viral treatments including TF. The results of this study are similar to the results of the study in Example 7.

TABLE 9

| Groups | MHC II/ HLA-DR Increase | Gamma/ Delta Expression | CD 4 Count | HIV-1 Antibodies | HIV-1 RNA by PCR | Quantitative HIV-1 PBMC |
| --- | --- | --- | --- | --- | --- | --- |
| Group 1 <200 CD4 | 100% | Great Increase | No Sig. Change | 400% Increase | 96%* Decrease | Decrease >90% |
| Group II 200-500 CD4 | 100% | Great Increase | No Sig. Change | 400% Increase | 95%* Decrease | Decrease >90% |
| Group III >500 CD4 | 100% | Great Increase | No Sig. Change | 400% Increase | 87%* Decrease | Decrease >90% |

*statistically significant (p = 0.021).

EXAMPLE 8

This example provides the results of a masked, randomized clinical study conducted with twenty patients in Bulgaria. The study was carried out in accordance with Good Clinical Practices and was subject to Institutional Review Board approval. The twenty patients were separated into subgroups based on the CD 4 count of the individual patient: Group I included AIDS patients with CD 4 counts of less then 200; Group II included HIV-1 patients with CD 4 counts of 200-500; and Group III included HIV-1 patients with CD 4 counts of more then 500.

Pre-treatment and post-treatment evaluations in all patients included patient history and physical examination, blood chemistries comprising a complete blood count (CBC), standard Chem 7, liver panel, and serum amylase. Further, blood analysis of T-lymphocyte CD 3, CD 4, and CD 8 was followed. Quantitative antibodies against HIV-1 by ELISA, levels of p24 core antigen, quantitative HIV-1 RNA levels in plasma by PCR, quantitative HIV-1 infectious units of virus in peripheral blood mononuclear cells (PBMCs) and quantitative HIV-1 infectious units of virus in blood plasma were also evaluated.

The results of the clinical tests conducted on the twenty patients are shown in the following TABLES 10-29, respectively. The following TABLE 30 summarizes the patients' quantitative HIV-1 RNA levels in plasma, as determined by PCR, up to 330 days from the start of the study.

The results of EXAMPLES 7 and 8 can be summarized as follows:

Increase in WBC after the third week of treatment.

Two times increase in MHC II cell expression as well as increase in HLA-DR receptors expression after the first week of treatment.

Increase in gamma/delta chain expression on T-cells after the second week of the treatment and their decrease after the fourth week.

Drop in CD4 cells count after the second week, and a gradual, uninterrupted increase thereafter.

Increase and persistent elevation of IgG level.

Ten to twenty times increase in HIV-1 antibodies after the fourth week of treatment.

Decrease in quantity of the viral load in plasma to zero.

One or two log decrease in HIV-1 RNA by PCR

Reduction of HIV-1 infected cell population to undetectable levels as measured by PBMC culture.

Full restoration of the electrophoretic pattern to that of a healthy donor.

TABLE 10

Patient No 002
Blood analysis

| | | | | | Week/Month | | | | | |
|---|---|---|---|---|---|---|---|---|---|---|
| | −1 | Base | 2w | 4w | 6w | 8w | 3m | 4m | 5m | 6m |
| INJECTION | | 0 | 4 | 8 | 12 | 16 | — | — | — | — |
| Red Blood cells count | | 4.31 | 4.4 | 3.28 | 3.69 | 3.3 | 3.13 | 3.51 | 3.6 | 3.37 |
| Hemoglobin | | 152 | 152 | 126 | 133 | 120 | 118 | 128 | 130 | 121 |
| Total WBC count | | 3.5 | 4.8 | 5.0 | 4.9 | 4.7 | 4.6 | 6.1 | 4.1 | 4.6 |
| Total St (% of WBC) | | 3 | 7 | 6 | 4 | 2 | 4 | 5 | 7 | 10 |
| Total Seg (% of WBC) | | 59 | 56 | 63 | 59 | 60 | 54 | 63 | 63 | 61 |
| Total Ly (% of WBC) | | 31 | 30 | 24 | 31 | 34 | 38 | 26 | 27 | 20 |
| Total Mo (% of WBC) | | 7 | 5 | 4 | 5 | 4 | 3 | 4 | 4 | 6 |
| Total Ba (% of WBC) | | — | — | — | — | — | — | — | — | — |
| Total Eo (% of WBC) | | 3 | 2 | 3 | 2 | — | 1 | 2 | — | 3 |
| Platelet Count | | 148 | 154 | 150 | 161 | 152 | 149 | 171 | 179 | 160 |
| ESR (Westergreen) | | 50/72 | 54/78 | 40/72 | 22/39 | 57/70 | 44/62 | 30/50 | 38/57 | 42/60 |
| Total protein | | 87 | 98 | 93 | 91 | 82 | 87 | 90 | 84 | 84 |
| Albumin | | 42 | 41 | 41 | 42 | 40 | 39 | 45 | 39 | 40 |
| ASAT (GOT) | | 28 | 35 | 25 | 31 | 23 | 40 | 18 | 21 | 19 |
| ALAT (GPT) | | 32 | 24 | 31 | 39 | 24 | 23 | 26 | 35 | 28 |
| Absolute CD3 | 1346 | 1283 | 1713 | 1294 | 1307 | 1232 | 1080 | 1388 | 1293 | 892 |
| Absolute CD4 | 201 | 162 | 263 | 168 | 186 | 161 | 147 | 178 | 165 | 103 |
| Absolute CD8 | 1072 | 1008 | 1249 | 1056 | 1031 | 1018 | 883 | 1120 | 1019 | 733 |
| CD4/CD8 Ratio | 0.19 | 0.16 | 0.20 | 0.16 | 0.18 | 0.16 | 0.17 | 0.16 | 0.16 | 0.14 |
| HIV-1 Antigen (p24) CD | | neg.(−) | neg.(−) | neg.(−) | neg.(−) | neg.(−) | neg.(−) | pos.(+) 30 pg/ml | pos.(+) 25-30 pg/ml | pos.(+) 54-4 pg/ml |
| Anti HIV-1 Antibody (Anti p24) | | | | | | | | | | |
| Non diluted serum | | 0.017 | | | 0.012 | 0.013 | 0.009 | 0.008 | 0.005 | 0.009 |
| Diluted-(1:50) | | 0.67 | | | 0.37 | 0.54 | 0.27 | 0.23 | 0.17 | 0.42 |
| Diluted-(1:2500) | | | 26.44 | 3.31 | 1.94 | 7.45 | 9.37 | 9.77 | neg.(−) | neg.(−) |
| HIV-1 RNA by PCR Quant/log/ | | 5.68 | | 5.68 | | 4.42 | 5.81 | | | 5.25 |
| HIV-1 RNA by PCR Quant -number of copies | | $4.77 \times 10^5$ | | $4.79 \times 10^5$ | | $2.66 \times 10^4$ | $6.53 \times 10^5$ | | | $1.78 \times 10^5$ |

TABLE 11

Patient No 003
Blood analysis

| | | | | | Week/Month | | | | | |
|---|---|---|---|---|---|---|---|---|---|---|
| | −1 | Base | 2w | 4w | 6w | 8w | 3m | 4m | 5m | 6m |
| INJECTION | | 0 | 4 | 8 | 12 | 16 | — | — | — | — |
| Red blood cells count | | 4.5 | 4.2 | 3.61 | 4.09 | 3.5 | 3.31 | 3.27 | 3.11 | 3.39 |
| Hemoglobin | | 140 | 135 | 132 | 146 | 128 | 128 | 130 | 128 | 128 |
| Total WBC count | | 6.4 | 6.3 | 6.3 | 5.8 | 3.9 | 3.5 | 5.5 | 6.9 | 4.9 |
| Total St (% of WBC) | | 2 | 9 | 6 | 4 | 4 | | 2 | 8 | 6 |
| Total Seg (% of WBC) | | 51 | 56 | 47 | 57 | 51 | 54 | 49 | 55 | 58 |
| Total Ly (% of WBC) | | 38 | 31 | 34 | 33 | 40 | 38 | 40 | 30 | 31 |
| Total Mo (% of WBC) | | 5 | 4 | 4 | 1 | 6 | 4 | 4 | 3 | 3 |
| Total Ba (% of WBC) | | — | — | — | — | — | — | — | — | — |
| Total Eo (% of WBC) | | 4 | 9 | 2 | 5 | 9 | 4 | 5 | 4 | 2 |
| Platelet Count | | 164 | 163 | 183 | 174 | 178 | 180 | 184 | 180 | 179 |
| ESR (Westergreen) | | 16/24 | 30/54 | 18/39 | 16/33 | 30/46 | 15/27 | 15/37 | 25/50 | 15/40 |
| Total protein | | 77 | 107 | 87 | 101 | 83 | 87 | 86 | 83 | 83 |
| Albumin | | 38 | 44 | 41 | 44 | 39 | 42 | 44 | 42 | 43 |
| ASAT (GOT) | | 8 | 15 | 29 | 20 | 22 | 12 | 16 | 22 | 24 |
| ALAT (GPT) | | 12 | 18 | 36 | 16 | 27 | 14 | 10 | 25 | 27 |
| Absolute CD3 | | 2418 | 2566 | 2195 | 2574 | 3479 | 1882 | 2616 | 1871 | 1497 |
| Absolute CD4 | 303 | 529 | 492 | 510 | 398 | 576 | 279 | 451 | 288 | 227 |
| Absolute CD8 | 1054 | 1791 | >2000 | 1586 | >2000 | >2000 | 1534 | >2000 | 1555 | 1230 |
| CD4/CD8 Ratio | 0.28 | 0.30 | <0.25 | 0.32 | <0.20 | <0.29 | 0.18 | <0.23 | 0.19 | 0.18 |
| HIV-1 Antigen (p24) CD | | neg.(−) | neg.(−) | neg.(−) | neg.(−) | neg.(−) | neg.(−) | neg.(−) | neg.(−) | neg.(−) |
| Anti HIV-1 Antibody (Anti p24) | | | | | | | | | | |
| Non diluted serum | | 0.02 | 0.028 | 0. | | 0.027 | | 0.028 | 0.01 | 0.02 |
| Diluted-(1:50) | | 1.39 | 0.63 | | | 1.32 | | 1.29 | 1.19 | 1.17 | 1.24 |

TABLE 11-continued

Patient No 003
Blood analysis

| | −1 | Base | 2w | 4w | 6w | 8w | 3m | 4m | 5m | 6m |
|---|---|---|---|---|---|---|---|---|---|---|
| Diluted-(1:2500) | | 5.74 | 7.50 | 9.42 | 49.81 | 13.34 | 10.09 | 12.51 | 15.40 | 18.21 |
| HIV-1 RNA by PCR Quant | | 3.22 | | 3.88 | | 3.67 | 3.62 | | | 3.31 |
| HIV-1 RNA by PCR Quant -number of copies | | $1.65 \times 10^3$ | | $7.56 \times 10^3$ | | $4.70 \times 10^3$ | $4.21 \times 10^3$ | | | $2.05 \times 10^3$ |

TABLE 12

Patient No 005
Blood analysis

| | −1 | Base | 2w | 4w | 6w | 8w | 3m | 4m | 5m | 6m |
|---|---|---|---|---|---|---|---|---|---|---|
| INJECTION | | 0 | 4 | 8 | 12 | 16 | — | — | — | |
| Red blood cells count | | 3.71 | 3.3 | 3.31 | 3.09 | 3.3 | 3.12 | 3.27 | | |
| Hemoglobin | | 128 | 116 | 116 | 108 | 115 | 109 | 112 | | |
| Total WBC count | | 8.1 | 6.0 | 5.7 | 5.3 | 3.9 | 4.2 | 5.4 | | |
| Total St(% of WBC) | | 8 | 7 | 2 | 8 | 5 | 6 | 4 | | |
| Total Seg (% of WBC) | | 59 | 52 | 54 | 54 | 63 | 64 | 57 | | |
| Total Ly (% of WBC) | | 28 | 35 | 38 | 28 | 21 | 20 | 31 | | |
| Total Mo (% of WBC) | | 5 | 5 | 6 | 10 | 4 | 8 | 3 | | |
| Total Ba (% of WBC) | | — | — | — | — | — | — | — | | |
| Total Eo (% of WBC) | | — | 1 | — | 4 | 7 | 2 | 5 | | |
| Platelet Count | | 195 | 190 | 185 | 189 | 190 | 196 | 179 | | |
| ESR (Westergreen) | | 6/10 | 14/21 | 7/18 | 19/39 | 12/26 | 5/10 | 8/17 | | |
| Total protein | | 87 | 68 | 82 | 86 | 78 | 79 | 76 | | |
| Albumin | | 42 | 40 | 42 | 43 | 41 | 40 | 40 | | |
| ASAT (GOT) | | 27 | 27 | 31 | 10 | 24 | 24 | 14 | | |
| ALAT (GPT) | | 21 | 17 | 17 | 15 | 30 | 30 | 16 | | |
| Absolute CD3 | | 1639 | 2772 | 2613 | 2977 | 2306 | 2625 | 1840 | | 2352 |
| Absolute CD4 | 503 | 570 | 724 | 766 | 803 | 509 | 593 | 414 | | 432 |
| Absolute CD8 | 966 | 952 | 1866 | 1683 | 1952 | 1605 | 1869 | 1353 | | 1795 |
| CD4/CD8 Ratio | 0.52 | 0.60 | 0.39 | 0.46 | 0.41 | 0.32 | 0.32 | 0.31 | | |
| HIV-1 Antigen (p24) CD | | neg.(−) | neg.(−) | neg.(−) | neg.(−) | neg.(−) | neg.(−) | neg.(−) | | neg.(−) |
| Anti HIV-1 Antibody (Anti p24) | | | | | | | | | | |
| Non diluted serum | | | | | 0.036 | 0.017 | | 0.01 | | 0.01 |
| Diluted-(1:50) | | 1.25 | 1.01 | | 1.74 | 0.98 | | 0.71 | | 0.73 |
| Diluted-(1:2500) | | | 2.02 | 51.01 | 34.74 | 49.26 | neg.(−) | neg.(−) | | |
| HIV-1 RNA by PCR Quant | | 3.72 | | 3.68 | | 3.15 | 2.76 | | | 3.30 |
| HIV-1 RNA by PCR Quant -number of copies | | $5.3 \times 10^3$ | | $4.77 \times 10^3$ | | $1.40 \times 10^3$ | $5.78 \times 10^2$ | | | $1.98 \times 10^3$ |

TABLE 13

Patient No 006
Blood analysis

| | −1 | Base | 2w | 4w | 6w | 8w | 3m | 4m | 5m | 6m |
|---|---|---|---|---|---|---|---|---|---|---|
| INJECTION | | 0 | 4 | 8 | 12 | 16 | — | — | — | — |
| Red blood cells count | | 3.09 | 3.21 | 3.3 | 3.44 | 3.4 | 3.27 | 3.4 | 3.61 | 3.3 |
| Hemoglobin | | 124 | 108 | 128 | 124 | 126 | 112 | 120 | 126 | 122 |
| Total WBC count | | 5.2 | 3.3 | 4.0 | 5.0 | 4.8 | 3.4 | 4.5 | 4.7 | 5.1 |
| Total St(% of WBC) | | 8 | 3 | 7 | 6 | 6 | 2 | 6 | 7 | 8 |
| Total Seg (% of WBC) | | 67 | 63 | 52 | 65 | 55 | 52 | 47 | 54 | 61 |
| Total Ly (% of WBC) | | 22 | 25 | 37 | 23 | 34 | 40 | 39 | 35 | 20 |
| Total Mo (% of WBC) | | 3 | 4 | 4 | 4 | 5 | 6 | 7 | 3 | 7 |
| Total Ba (% of WBC) | | — | — | — | — | — | — | — | — | — |
| Total Eo (% of WBC) | | — | 2 | — | 2 | — | — | 1 | 1 | 4 |
| Platelet Count | | 158 | 182 | 162 | 174 | 168 | 177 | 170 | 178 | 178 |

TABLE 13-continued

Patient No 006
Blood analysis

| | | | | | Week/Month | | | | | |
|---|---|---|---|---|---|---|---|---|---|---|
| | −1 | Base | 2w | 4w | 6w | 8w | 3m | 4m | 5m | 6m |
| ESR (Westergreen) | | 8/18 | 29/56 | 22/52 | 21/41 | 22/40 | 8/18 | 8/16 | 8/19 | 8/16 |
| Total protein | | 98 | 87 | 86 | 91 | 79 | 74 | 72 | 78 | 77 |
| Albumin | | 42 | 40 | 43 | 43 | 40 | 39 | 44 | 43 | 40 |
| ASAT (GOT) | | 11 | 20 | 26 | 15 | 12 | 8 | 12 | 8 | 10 |
| ALAT (GPT) | | 7 | 36 | 33 | 17 | 24 | 17 | 13 | 10 | 21 |
| Absolute CD3 | | 1110 | 1393 | 1473 | 1752 | 2074 | 1406 | 1661 | 1546 | 1182 |
| Absolute CD4 | 196 | 198 | 226 | 253 | 250 | 248 | 230 | 219 | 211 | 176 |
| Absolute CD8 | 882 | 846 | 1007 | 1155 | 1436 | 1795 | 1129 | 1346 | 1294 | 972 |
| CD4/CD8 Ratio | 0.22 | 0.23 | 0.22 | 0.22 | 0.17 | 0.14 | 0.20 | 0.16 | 0.16 | 0.18 |
| HIV-1 Antigen (p24) CD | | neg.(−) | neg.(−) | neg.(−) | neg.(−) | neg.(−) | neg.(−) | neg.(−) | neg.(−) | neg.(−) |
| Anti HIV-1 Antibody | | | | | | | | | | |
| (Anti p24) | | | | | | | | | | |
| Non diluted serum | | 0.027 | | | 0.017 | | | 0.017 | 0.01 | 0.01 |
| Diluted-(1:50) | | 1.07 | | | 0.68 | | 0.91 | 0.53 | 0.71 | 0.56 |
| Diluted-(1:2500) | | 1278 | 14.71 | 9.54 | 4.92 | 18.65 | 15.82 | 7.79 | 12.66 | 69.8 |
| HIV-1 RNA by PCR | | 5.06 | | 4.75 | | 4.24 | 3.64 | | | 4.35 |
| Quant | | | | | | | | | | |
| HIV-1 RNA by PCR | | $1.14 \times 10^3$ | | $5.62 \times 10^4$ | | $1.76 \times 10^4$ | $4.37 \times 10^3$ | | | $2.22 \times 10^4$ |
| Quant -number of copies | | | | | | | | | | |

TABLE 14

Patient No 008
Blood analysis

| | | | | | Week/Month | | | | | |
|---|---|---|---|---|---|---|---|---|---|---|
| | −1 | Base | 2w | 4w | 6w | 8w | 3m | 4m | 5m | 6m |
| INJECTION | | 0 | 4 | 8 | 12 | 16 | — | — | — | — |
| Red blood cells count | | 3.68 | 3.19 | 3.3 | 3.44 | 3.5 | 3.39 | 3.44 | 3.36 | 3.94 |
| Hemoglobin | | 136 | 122 | 132 | 124 | 130 | 129 | 130 | 128 | 132 |
| Total WBC count | | 6.0 | 3.6 | 4.0 | 5.0 | 4.0 | 3.7 | 4.8 | 4.8 | 3.6 |
| Total St(% of WBC) | | 4 | 7 | 7 | 6 | 2 | 3 | 10 | 7 | 7 |
| Total Seg (% of WBC) | | 66 | 58 | 59 | 65 | 66 | 59 | 63 | 63 | 59 |
| Total Ly (% of WBC) | | 25 | 30 | 27 | 23 | 24 | 30 | 24 | 21 | 28 |
| Total Mo (% of WBC) | | 4 | 3 | 4 | 4 | 4 | 4 | 2 | 4 | 8 |
| Total Ba (% of WBC) | | — | — | — | — | — | — | — | — | — |
| Total Eo (% of WBC) | | 1 | 2 | 3 | 2 | 4 | 4 | 1 | — | — |
| Platelet Count | | 156 | 198 | 175 | 174 | 177 | 190 | 177 | 175 | 180 |
| ESR (Westergreen) | | 8/16 | 20/45 | 15/40 | 20/41 | 20/40 | 20/32 | 15/31 | 5/12 | 10/19 |
| Total protein | | 75 | 73 | 78 | 82 | 79 | 84 | 79 | 89 | 84 |
| Albumin | | 42 | 40 | 41 | 40 | 41 | 44 | 41 | 44 | 41 |
| ASAT (GOT) | | 41 | 19 | 30 | 12 | 22 | 12 | 14 | 9 | 10 |
| ALAT (GPT) | | 30 | 19 | 25 | 23 | 24 | 20 | 23 | 14 | 15 |
| Absolute CD3 | | 2555 | 2367 | 2122 | 1580 | 2383 | 1550 | 1810 | 1005 | 2307 |
| Absolute CD4 | 92 | 206 | 199 | 188 | 159 | 192 | 165 | 188 | 147 | 248 |
| Absolute CD8 | 646 | 1966 | 1934 | 1704 | 1229 | 1843 | 1216 | 1382 | 745 | 1836 |
| CD4/CD8 Ratio | 0.14 | 0.10 | 0.10 | 0.11 | 0.13 | 0.10 | 0.14 | 0.14 | 0.20 | 0.14 |
| HIV-1 Antigen (p24) CD | | neg.(−) | neg.(−) | neg.(−) | neg.(−) | neg.(−) | neg.(−) | neg.(−) | neg.(−) | neg.(−) |
| Anti HIV-1 Antibody | | | | | | | | | | |
| (Anti p24) | | | | | | | | | | |
| Non diluted serum | | | | | | | | 0.02 | HL | 0.02 |
| Diluted-(1:50) | | | | | | | | 1.39 | 1.42 | 1.34 |
| Diluted-(1:2500) | | 10.79 | 15.61 | 30.4 | 68.28 | 70.98 | 28.28 | 18.13 | 15.17 | −14.94 |
| HIV-1 RNA by PCR | | | | | | | | | | |
| Quant | | | | | | | | | | |
| HIV-1 RNA by PCR | | | | | | | | | | |
| Quant -number of copies | | | | | | | | | | |

TABLE 15

Patient No 009
Blood analysis

| | -1 | Base | 2w | 4w | 6w | 8w | 3m | 4m | 5m | 6m |
|---|---|---|---|---|---|---|---|---|---|---|
| | | | | | | | | | Week/Month | |
| INJECTION | | 0 | 4 | 8 | 12 | 16 | — | | | |
| Red blood cells count | | 3.91 | 3.35 | 3.6 | 3.39 | 3.7 | 4.31 | | | |
| Hemoglobin | | 164 | 144 | 140 | 140 | 139 | 142 | | | |
| Total WBC count | | 7.2 | 4.7 | 5.0 | 3.6 | 4.5 | 4.2 | | | |
| Total St(% of WBC) | | 4 | 8 | 4 | 10 | 4 | 9 | | | |
| Total Seg (% of WBC) | | 67 | 48 | 57 | 48 | 59 | 57 | | | |
| Total Ly (% of WBC) | | 24 | 32 | 32 | 32 | 30 | 29 | | | |
| Total Mo (% of WBC) | | 3 | 7 | 7 | 10 | 4 | 4 | | | |
| Total Ba (% of WBC) | | — | — | — | — | — | — | | | |
| Total Eo (% of WBC) | | 2 | 2 | — | — | — | 1 | | | |
| Platelet Count | | 144 | 148 | 150 | 138 | 154 | 160 | | | |
| ESR (Westergreen) | | 4/8 | 6/17 | 5/11 | 9/20 | 10/18 | 17/31 | | | |
| Total protein | | 60 | 73 | 79 | 87 | 80 | 84 | | | |
| Albumin | | 41 | 43 | 41 | 44 | 40 | 41 | | | |
| ASAT (GOT) | | 12 | 15 | 27 | 20 | 20 | 18 | | | |
| ALAT (GPT) | | 27 | 28 | 47 | 23 | 30 | 9 | | | |
| Absolute CD3 | | 1002 | 1377 | 1562 | 1552 | 1335 | 1073 | | | 1365 |
| Absolute CD4 | 319 | 300 | 445 | 458 | 399 | 351 | 322 | | | 370 |
| Absolute CD8 | 732 | 647 | 882 | 992 | 1098 | 936 | 715 | | | 948 |
| CD4/CD8 Ratio | 0.44 | 0.46 | 0.50 | 0.46 | 0.36 | 0.38 | 0.45 | | | 0.39 |
| HIV-1 Antigen (p24) CD | | neg.(−) | neg.(−) | pos.(+) 10 pg/ml | neg.(−) | pos.(+) 20 pg/ml | neg.(−) | | | pos.(+) 50 pg/ml |
| Anti HIV-1 Antibody (Anti p24) | | | | | | | | | | |
| Non diluted serum | | 0.002 | | | | | 0.083 | | | neg.(−) |
| Diluted-(1:50) | | | | | | 0.24 | 0.48 | | | neg.(−) |
| Diluted-(1:2500) | | | | | | | 2.11 | | | neg.(−) |
| HIV-1 RNA by PCR Quant | | 5.34 | | 5.39 | | 5.65 | 5.27 | | | 5.19 |
| HIV-1 RNA by PCR Quant -number of copies | | 2.25 × 10³ | | 2.44 × 10⁵ | | 4.45 × 10⁵ | 1.86 × 10⁵ | | | 1.56×10⁵ |

TABLE 16

Patient No 010
Blood analysis

| | -1 | Base | 2w | 4w | 6w | 8w | 3m | 4m | 5m | 6m |
|---|---|---|---|---|---|---|---|---|---|---|
| | | | | | | | | | Week/Month | |
| INJECTION | | 0 | 4 | 8 | 12 | 16 | — | — | — | — |
| Red blood cells count | | 3.309 | 3.1 | 3.2 | 3.07 | 3.2 | 3.29 | 3.3 | 3.32 | 3.5 |
| Hemoglobin | | 129 | 120 | 120 | 118 | 118 | 104 | 116 | 116 | 120 |
| Total WBC count | | 3.6 | 4.4 | 5.0 | 5.3 | 4.2 | 4.3 | 6.8 | 6.6 | 5.1 |
| Total St(% of WBC) | | 2 | 7 | 2 | 8 | 2 | 4 | 6 | 5 | 2 |
| Total Seg (% of WBC) | | 51 | 51 | 60 | 46 | 56 | 50 | 58 | 62 | 54 |
| Total Ly (% of WBC) | | 32 | 32 | 32 | 38 | 32 | 37 | 33 | 26 | 34 |
| Total Mo (% of WBC) | | 5 | 7 | 4 | 6 | 4 | 5 | 3 | 6 | 7 |
| Total Ba (% of WBC) | | — | — | — | — | — | — | — | — | — |
| Total Eo (% of WBC) | | 2 | 3 | 2 | 2 | 6 | 4 | — | 1 | 3 |
| Platelet Count | | 152 | 155 | 160 | 154 | 165 | 160 | 164 | 198 | 178 |
| ESR (Westergreen) | | 5/10 | 20/36 | 10/17 | 8/18 | 20/30 | 8/16 | 10/18 | 12/26 | 10/19 |
| Total protein | | 79 | 80 | 76 | 83 | 75 | 84 | 78 | 80 | 83 |
| Albumin | | 43 | 39 | 44 | 42 | 39 | 40 | 41 | 44 | 42 |
| ASAT (GOT) | | 28 | 19 | 17 | 19 | 14 | 30 | 15 | 12 | |
| ALAT (GPT) | | 24 | 27 | 32 | 28 | 24 | 19 | 13 | 10 | 29 |
| Absolute CD3 | | 1105 | 1186 | 1415 | 1495 | 1305 | 1153 | 1205 | 1526 | 1122 |
| Absolute CD4 | 474 | 599 | 637 | 685 | 631 | 620 | 517 | 544 | 742 | 547 |
| Absolute CD8 | 313 | 457 | 476 | 677 | 765 | 604 | 585 | 600 | 731 | 513 |
| CD4/CD8 Ratio | 1.51 | 1.31 | 1.34 | 1.01 | 0.82 | 1.03 | 0.88 | 0.91 | 1.02 | 1.07 |
| HIV-1 Antigen (p24) CD | | neg.(−) | neg.(−) | neg.(−) | neg.(−) | neg.(−) | neg.(−) | neg.(−) | neg.(−) | neg.(−) |
| Anti HIV-1 Antibody (Anti p24) | | | | | | | | | | |
| Non diluted serum | | | | | | | | 0.02 | 0.01 | 0.02 |
| Diluted-(1:50) | | 1.52 | | | | | | 1.29 | 1.19 | 1.14 |
| Diluted-(1:2500) | | 14.43 | 17.3 | 37.78 | 21.23 | 50.13 | | 28.74 | 35.51 | 31.88 |

TABLE 16-continued

Patient No 010
Blood analysis

| | -1 | Base | 2w | 4w | 6w | 8w | 3m | 4m | 5m | 6m |
|---|---|---|---|---|---|---|---|---|---|---|
| HIV-1 RNA by PCR Quant | | 4.12 | | 5.29 | | 5.15 | 3.85 | | | 3.67 |
| HIV-1 RNA by PCR Quant -number of copies | | $1.32 \times 10^4$ | | $1.97 \times 10^5$ | | $1.42 \times 10^5$ | $7.06 \times 10^3$ | | | $4.72 \times 10^3$ |

TABLE 18

Patient No 12
Blood analysis

| | -1 | Base | 2w | 4w | 6w | 8w | 3m | 4m | 5m | 6m |
|---|---|---|---|---|---|---|---|---|---|---|
| INJECTION | | 0 | 4 | 8 | 12 | 16 | — | — | — | — |
| Red blood cells count | | 3.21 | 4.0 | 3.24 | 3.3 | 3.5 | 3.7 | 3.44 | 3.42 | 3.31 |
| Hemoglobin | | 116 | 136 | 128 | 128 | 134 | 136 | 136 | 134 | 130 |
| Total WBC count | | 4.9 | 6.3 | 4.2 | 5.1 | 5.2 | 6.0 | 5.6 | 4.3 | 6.6 |
| Total St(% of WBC) | | 4 | 6 | 9 | 4 | 8 | 3 | 9 | 8 | 1 |
| Total Seg (% of WBC) | | 50 | 55 | 54 | 55 | 59 | 62 | 52 | 45 | 71 |
| Total Ly (% of WBC) | | 36 | 33 | 28 | 31 | 25 | 29 | 28 | 40 | 22 |
| Total Mo (% of WBC) | | 6 | 4 | 5 | 6 | 3 | 3 | 6 | 5 | 6 |
| Total Ba (% of WBC) | | — | — | !PI-1 | — | — | — | — | — | — |
| Total Eo (% of WBC) | | 4 | 2 | 3 | 4 | 5 | 3 | 5 | 2 | — |
| Platelet Count | | 200 | 148 | 163 | 158 | 152 | 150 | 160 | 173 | 165 |
| ESR (Westergreen) | | 7/17 | 6/12 | 15/33 | 14/30 | 22/30 | 7/16 | 10/16 | 8/18 | 5/10 |
| Total protein | | 81 | 74 | 89 | 90 | 88 | 86 | 86 | 84 | 80 |
| Albumin | | 41 | 42 | 46 | 40 | 42 | 42 | 43 | 44 | 42 |
| ASAT (GOT) | | 24 | 22 | 33 | 23 | 12 | 20 | 12 | 14 | 19 |
| ALAT (GPT) | | 15 | 54 | 60 | 34 | 30 | 29 | 10 | 25 | 26 |
| Absolute CD3 | | 2250 | 2647 | 3500 | 2439 | 2560 | 2534 | 2720 | 2456 | 2797 |
| Absolute CD4 | 584 | 843 | 1108 | 1316 | 817 | 871 | 851 | 809 | 913 | 953 |
| Absolute CD8 | 1018 | 1308 | 1443 | >2000 | 1546 | 1623 | 1576 | 1831 | 1495 | 1784 |
| CD4/CD8 Ratio | 0.57 | 0.64 | 0.77 | <0.66 | 0.53 | 0.54 | 0.54 | 0.44 | 0.61 | 0.53 |
| HIV-1 Antigen (p24) CD | | neg.(-) | neg.(-) | neg.(-) | neg.(-) | neg.(-) | neg.(-) | neg.(-) | neg.(-) | neg.(-) |
| Anti HIV-1 Antibody (Anti p24) | | | | | | | | | | |
| Non diluted serum | | 0.002 | | | 0.001 | 0.002 | 0.003 | 0.02 | 0.02 | 0.002 |
| Diluted-(1:50) | | | 0.02 | 0.032 | neg.(-) | | neg.(-) | 0.09 | neg.(-) | neg.(-) |
| Diluted-(1:2500) | | | | | | | neg.(-) | neg.(-) | neg.(-) | neg.(-) |
| HIV-1 RNA by PCR Quant | | 4.77 | 4.89 | | 5.21 | 4.51 | | | 4.44 | |
| HIV-1 RNA by PCR Quant -number of copies | | $5.86 \times 10^4$ | $7.71 \times 10^4$ | | $1.64 \times 10^5$ | $3.23 \times 10^4$ | | | $2.79 \times 10^4$ | |

TABLE 19

Patient NO 013
Blood analysis

| | -1 | Base | 2w | 4w | 6w | 8w | 3m | 4m | 5m | 6m |
|---|---|---|---|---|---|---|---|---|---|---|
| INJECTION | | 0 | 4 | 8 | 12 | 16 | — | — | — | — |
| Red blood cells count | | 3.07 | 3.10 | 3.09 | 3.2 | 3.2 | 3.3 | 3.21 | 3.32 | 3.31 |
| Hemoglobin | | 98 | 108 | 98 | 110 | 112 | 120 | 124 | 126 | 123 |
| Total WBC count | | 3.6 | 4.5 | 3.3 | 3.6 | 4.8 | 3.7 | 3.3 | 4.3 | 4.1 |
| Total St(% of WBC) | | 2 | 4 | 2 | 7 | 8 | 2 | 6 | 3 | 7 |
| Total Seg (% of WBC) | | 66 | 56 | 59 | 48 | 47 | 58 | 52 | 50 | 52 |
| Total Ly (% of WBC) | | 28 | 34 | 34 | 36 | 35 | 36 | 33 | 40 | 36 |
| Total Mo (% of WBC) | | 2 | 4 | 3 | 5 | 6 | 4 | 6 | 5 | 4 |
| Total Ba (% of WBC) | | — | — | — | — | — | — | — | — | — |
| Total Eo (% of WBC) | | 2 | 2 | 2 | 4 | 4 | — | 3 | 2 | 1 |
| Platelet Count | | 151 | 158 | 162 | 160 | 150 | 161 | 170 | 165 | 177 |

TABLE 19-continued

Patient NO 013
Blood analysis

| | −1 | Base | 2w | 4w | 6w | 8w | 3m | 4m | 5m | 6m |
|---|---|---|---|---|---|---|---|---|---|---|
| ESR (Westergreen) | | 6/12 | 17/34 | 17/30 | 18/28 | 20/38 | 20/38 | 18/34 | 28/40 | 10/26 |
| Total protein | | 87 | 80 | 90 | 78 | 89 | 76 | 78 | 74 | 80 |
| Albumin | | 44 | 43 | 42 | 39 | 39 | 37 | 43 | 44 | 40 |
| ASAT (GOT) | | 23 | 11 | 21 | 18 | 12 | 26 | 23 | 12 | 24 |
| ALAT (GPT) | | 23 | 25 | 25 | 28 | 39 | 14 | 12 | 13 | 20 |
| Absolute CD3 | | 812 | 844 | 929 | 810 | 1017 | 703 | 963 | 832 | 898 |
| Absolute CD4 | 265 | 229 | 270 | 181 | 219 | 274 | 220 | 274 | 208 | 302 |
| Absolute CD8 | 601 | 554 | 563 | 713 | 570 | 733 | 468 | 657 | 612 | 596 |
| CD4/CD8 Ratio | 0.44 | 0.41 | 0.48 | 0.25 | 0.38 | 0.37 | 0.47 | 0.42 | 0.34 | 0.51 |
| HIV-1 Antigen (p24) CD | | neg.(−) | neg.(−) | neg.(−) | neg.(−) | neg.(−) | neg.(−) | neg.(−) | neg.(−) | neg.(−) |
| Anti HIV-1 Antibody (Anti p24) | | | | | | | | | | |
| Non diluted serum | | | | | | | 0.02 | 0.01 | 0.02 | 0.03 |
| Diluted-(1:50) | | 1.48 | | | | | 1.38 | 0.96 | 1.37 | 1IL |
| Diluted-(1:2500) | | 24.61 | 25.85 | 36.57 | 30.38 | 41.99 | 22.79 | 26.21 | 25.55 | 42.13 |
| HIV-1 RNA by PCR Quant | | 3.51 | | 3.40 | | 4.77 | 3.85 | | | 4.40 |
| HIV-1 RNA by PCR Quant -number of copies | | $3.24 \times 10^3$ | | $2.51 \times 10^3$ | | $5.89 \times 10^4$ | $7.03 \times 10^3$ | | | $2.48 \times 10^4$ |

TABLE 20

Patient No 014
Blood analysis

| | −1 | Base | 2w | 4w | 6w | 8w | 3m | 4m | 5m | 6m |
|---|---|---|---|---|---|---|---|---|---|---|
| INJECTION | | 0 | 4 | 8 | 12 | 16 | — | — | — | |
| Red blood cells count | | 4.6 | 4.2 | 3.88 | 3.9 | 3.8 | 3.51 | 3.4 | 3.42 | 3.34 |
| Hemoglobin | | 156 | 136 | 134 | 138 | 136 | 134 | 136 | 135 | 121 |
| Total WBC count | | 3.5 | 4.0 | 6.0 | 6.0 | 4.8 | 5.3 | 6.1 | 4.2 | 6.0 |
| Total St(% of WBC) | | 2 | 5 | 8 | 9 | 4 | 12 | 6 | 7 | 2 |
| Total Seg (% of WBC) | | 49 | 43 | 42 | 53 | 57 | 43 | 53 | 44 | 66 |
| Total Ly (% of WBC) | | 38 | 40 | 37 | 34 | 33 | 37 | 30 | 38 | 31 |
| Total Mo (% of WBC) | | 3 | 8 | 8 | 4 | 4 | 3 | 5 | 6 | 1 |
| Total Ba (% of WBC) | | — | — | — | — | — | — | — | — | — |
| Total Eo (% of WBC) | | 8 | 4 | 5 | — | — | 5 | 6 | 5 | — |
| Platelet Count | | 147 | 171 | 165 | 179 | 174 | 157 | 162 | 171 | 179 |
| ESR (Westergreen) | | 6/12 | 10/32 | 15/28 | 16/20 | 16/22 | 10/19 | 8/15 | 10/18 | 5/10 |
| Total protein | | 80 | 89 | 79 | 77 | 74 | 74 | 68 | 70 | 79 |
| Albumin | | 39 | 42 | 40 | 39 | 41 | 39 | 37 | 37 | 42 |
| ASAT (GOT) | | 17 | 21 | 17 | 14 | 14 | 17 | 17 | 18 | 27 |
| ALAT (GPT) | | 18 | 47 | 24 | 20 | 18 | 23 | 17 | 28 | 30 |
| Absolute CD3 | | 1696 | 2197 | 3500 | 1927 | 1751 | 2370 | 3007 | 2113 | 2468 |
| Absolute CD4 | 782 | 789 | 1092 | 1732 | 849 | 898 | 1165 | 1347 | 989 | 1441 |
| Absolute CD8 | 1006 | 852 | 1025 | 1827 | 958 | 795 | 1103 | 1475 | 999 | 1253 |
| CD4/CD8 Ratio | 0.78 | 0.93 | 1.07 | 0.95 | 0.89 | 1.13 | 1.06 | 0.91 | 0.99 | 0.91 |
| HIV-1 Antigen (p24) CD | | neg.(−) | neg.(−) | neg.(−) | neg.(−) | neg.(−) | neg.(−) | neg.(−) | neg.(−) | neg.(−) |
| Anti HIV-1 Antibody (Anti p24) | | | | | | | | | | |
| Non diluted serum | | neg.(−) | neg.(−) | | neg.(−) | neg.(−) | 0.0008 | neg.(−) | neg.(−) | 0.005 |
| Diluted-(1:50) | | neg.(−) | neg.(−) | | neg.(−) | neg.(−) | neg.(−) | neg.(−) | neg.(−) | neg.(−) |
| Diluted-(1:2500) | | neg.(−) | neg.(−) | 3.74 | neg.(−) | neg.(−) | neg.(−) | neg.(−) | neg.(−) | neg.(−) |
| HIV-1 RNA by PCR Quant | | 3.71 | | 3.06 | | 2.35 | neg.(−) | | | 2.82 |
| HIV-1 RNA by PCR Quant -number of copies | | $5.15 \times 10^3$ | | $1.14 \times 10^3$ | | $2.25 \times 10^2$ | | | | $6.58 \times 10^2$ |

TABLE 21

Patient No 015
Blood analysis

| | | | | | Week/Month | | | | |
|---|---|---|---|---|---|---|---|---|---|
| | −1 | Base | 2w | 4w | 6w | 8w | 3m | 4m | 5m | 6m |
| INJECTION | | 0 | 4 | 8 | 12 | 16 | — | — | — | |
| Red blood cells count | | 3.7 | 3.21 | 3.2 | 3.3 | 3.3 | 3.09 | 3.1 | 3.27 | |
| Hemoglobin | | 120 | 118 | 120 | 124 | 120 | 118 | 120 | 118 | |
| Total WBC count | | 4.3 | 2.9 | 4.0 | 4.8 | 3.4 | 4.0 | 5.4 | 3.2 | |
| Total St(% of WBC) | | 9 | 7 | 7 | 4 | 8 | 6 | 6 | 12 | |
| Total Seg (% of WBC) | | 60 | 58 | 51 | 56 | 57 | 58 | 62 | 42 | |
| Total Ly (% of WBC) | | 24 | 31 | 36 | 33 | 22 | 26 | 29 | 40 | |
| Total Mo (% of WBC) | | 5 | 4 | 3 | 3 | 7 | 8 | 3 | 4 | |
| Total Ba (% of WBC) | | — | — | — | — | — | — | — | — | |
| Total Eo (% of WBC) | | 2 | — | 3 | 4 | 6 | 2 | 3 | 2 | |
| Platelet Count | | 164 | 171 | 168 | 159 | 149 | 167 | 152 | 170 | |
| ESR (Westergreen) | | 24/39 | 20/32 | 12/24 | 16/28 | 30/54 | 47/63 | 50/70 | 10/20 | |
| Total protein | | 83 | 82 | 80 | 80 | 82 | 87 | 80 | 83 | |
| Albumin | | 40 | 42 | 41 | 40 | 41 | 42 | 42 | 41 | |
| ASAT (GOT) | | 17 | 21 | 14 | 22 | 21 | 18 | 15 | 27 | |
| ALAT (GPT) | | 25 | 27 | 13 | 23 | 24 | 24 | 23 | 32 | |
| Absolute CD3 | | 660 | 660 | 833 | 663 | 569 | 473 | 520 | 505 | 801 |
| Absolute CD4 | 100 | 89 | 69 | 81 | 74 | 69 | 60 | 62 | 47 | 48 |
| Absolute CD8 | 816 | 494 | 539 | 659 | 559 | 463 | 365 | 417 | 420 | 678 |
| CD4/CD8 Ratio | 0.12 | 0.18 | 0.13 | 0.12 | 0.13 | 0.15 | 0.16 | 0.15 | 0.11 | 0.07 |
| HIV-1 Antigen (p24) CD | | neg.(−) | neg.(−) | neg.(−) | neg.(−) | neg.(−) | neg.(−) | neg.(−) | neg.(−) | neg.(−) |
| Anti HIV-1 Antibody (Anti p24) | | | | | | | | | | |
| Non diluted serum | | | | | | | 0.01 | 0.01 | 0.02 | 0.01 |
| Diluted-(1:50) | | 0.77 | 0.58 | 0.45 | 0.52 | 0.88 | 0.49 | 0.59 | 0.57 | 0.39 |
| Diluted-(1:2500) | | | 1.98 | 4.49 | neg.(−) | neg.(−) | neg.(−) | neg.(−) | neg.(−) | neg.(−) |
| HIV-1 RNA by PCR Quant | | 4.32 | | 5.16 | | 5.11 | 4.79 | | | 5.33 |
| HIV-1 RNA by PCR Quant -number of copies | | $2.08 \times 10^4$ | | $1.45 \times 10^3$ | | $1.30 \times 10^5$ | $6.14 \times 10^4$ | | | $2.14 \times 10^3$ |

TABLE 22

Patient No 016
Blood analysis

| | | | | | Week/Month | | | | |
|---|---|---|---|---|---|---|---|---|---|
| | −1 | Base | 2w | 4w | 6w | 8w | 3m | 4m | 5m | 6m |
| INJECTION | | 0 | 4 | 8 | 12 | 16 | — | — | — | |
| Red blood cells count | | 4.8 | 4.71 | 4.7 | 4.7 | 4.7 | 4.31 | 4.32 | 4.32 | |
| Hemoglobin | | 148 | 146 | 144 | 145 | 144 | 140 | 140 | 143 | |
| Total WBC count | | 3.9 | 3.0 | 3.7 | 4.0 | 3.5 | 6.6 | 4.1 | 6.6 | |
| Total St(% of WBC) | | 4 | 9 | 4 | 3 | 7 | 2 | 3 | 2 | |
| Total Seg (% of WBC) | | 47 | 54 | 44 | 55 | 46 | 51 | 47 | 46 | |
| Total Ly (% of WBC) | | 35 | 29 | 39 | 32 | 32 | 31 | 40 | 41 | |
| Total Mo (% of WBC) | | 8 | 5 | 4 | 3 | 8 | 6 | 7 | 9 | |
| Total Ba (% of WBC) | | — | — | — | — | — | — | — | — | |
| Total Eo (% of WBC) | | 6 | 3 | 9 | 7 | 7 | 10 | 3 | 2 | |
| Platelet Count | | 124 | 131 | 140 | 160 | 154 | 128 | 165 | 152 | |
| ESR (Westergreen) | | 9/15 | 32/50 | 24/38 | 28/42 | 20/40 | 9/16 | 10/18 | 15/24 | |
| Total protein | | 69 | 89 | 79 | 79 | 78 | 73 | 76 | 86 | |
| Albumin | | 40 | 42 | 40 | 39 | 40 | 40 | 43 | 42 | |
| ASAT (GOT) | | 21 | 52 | 13 | 18 | 10 | 10 | 21 | 21 | |
| ALAT (GPT) | | 19 | 30 | 12 | 20 | 21 | 24 | 23 | 30 | |
| Absolute CD3 | | 1926 | 3463 | 2198 | 3468 | 2868 | 3395 | 2464 | 3190 | 3058 |
| Absolute CD4 | 248 | 302 | 455 | 280 | 455 | 408 | 523 | 350 | 337 | 343 |
| Absolute CD8 | 1596 | 1656 | >2000 | >2000 | >2000 | >2000 | >2000 | >2000 | >2000 | >2000 |
| CD4/CD8 Ratio | 0.16 | 0.18 | 0.23 | <0.14 | <0.23 | <0.20 | <0.26 | 0.17 | <0.17 | <0.17 |
| HIV-1 Antigen (p24) CD | | neg.(−) | neg.(−) | neg.(−) | neg.(−) | neg.(−) | neg.(−) | neg.(−) | neg.(−) | neg.(−) |
| Anti HIV-1 Antibody (Anti p24) | | | | | | | | | | |
| Non diluted serum | | | | | | | 0.024 | 0.03 | 0.03 | 0.03 |
| Diluted-(1:50) | | 1.48 | 1.18 | 1.18 | 1.17 | | 1.18 | 1.44 | 1.45 | 1.43 |
| Diluted-(1:2500) | | 38.0 | 29.04 | 32.52 | 33.17 | 39.85 | 21.18 | 29.84 | 25.94 | 34.82 |

TABLE 22-continued

Patient No 016
Blood analysis

| | −1 | Base | 2w | 4w | 6w | 8w | 3m | 4m | 5m | 6m |
|---|---|---|---|---|---|---|---|---|---|---|
| HIV-1 RNA by PCR Quant | | 3.22 | | 3.32 | | 2.89 | 3.13 | | | 3.68 |
| HIV-1 RNA by PCR Quant -number of copies | | $1.68 \times 10^3$ | | $2.09 \times 10^3$ | | $7.74 \times 10^2$ | $1.35 \times 10^3$ | | | $4.82 \times 10^3$ |

TABLE 23

Patient No 017
Blood analysis

| | −1 | Base | 2w | 4w | 6w | 8w | 3m | 4m | 5m | 6m |
|---|---|---|---|---|---|---|---|---|---|---|
| INJECTION | | 0 | 4 | 8 | 12 | 16 | — | — | — | — |
| Red blood cells count | | 3.19 | 3.09 | 3.0 | 3.1 | 3.2 | 3.31 | 3.30 | 3.29 | 3.2 |
| Hemoglobin | | 112 | 108 | 106 | 115 | 110 | 126 | 124 | 125 | 122 |
| Total WBC count | | 4.6 | 3.0 | 6.0 | 4.5 | 5.7 | 11.3 | 7.6 | 6.9 | 4.0 |
| Total St(% of WBC) | | 4 | 2 | 4 | 4 | 4 | 7 | 6 | 3 | 2 |
| Total Seg (% of WBC) | | 50 | 59 | 63 | 44 | 51 | 60 | 44 | 61 | 58 |
| Total Ly (% of WBC) | | 37 | 29 | 22 | 39 | 30 | 25 | 39 | 31 | 32 |
| Total Mo (% of WBC) | | 3 | 6 | 3 | 3 | 3 | 3 | 3 | 3 | 4 |
| Total Ba (% of WBC) | | — | — | — | — | — | — | — | — | — |
| Total Eo (% of WBC) | | 6 | 4 | 8 | 7 | 12 | 5 | 7 | 2 | — |
| Platelet Count | | 194 | 200 | 202 | 198 | 163 | 207 | 174 | 179 | 168 |
| ESR (Westergreen) | | 35/60 | 20/36 | 18/32 | 18/34 | 20/38 | 20/32 | 18/32 | 20/30 | 5/10 |
| Total protein | | 88 | 93 | 83 | 78 | 78 | 75 | 77 | 87 | 76 |
| Albumin | | 40 | 42 | 40 | 41 | 42 | 42 | 42 | 41 | 41 |
| ASAT (GOT) | | 19 | 22 | 17 | 10 | 10 | 20 | 13 | 19 | 14 |
| ALAT (GPT) | | 20 | 29 | 20 | 15 | 15 | 21 | 18 | 29 | 13 |
| Absolute CD3 | | 1546 | 1855 | 1082 | 1478 | 2302 | 1253 | | 1265 | 1467 |
| Absolute CD4 | 180 | 402 | 393 | 252 | 309 | 532 | 274 | | 268 | 332 |
| Absolute CD8 | 581 | 1084 | 1338 | 784 | 1102 | 1669 | 896 | | 949 | 1068 |
| C04/CD8 Ratio | 0.31 | 0.37 | 0.29 | 0.32 | 0.28 | 0.32 | 0.31 | | 0.28 | 0.31 |
| HIV-1 Antigen (p24) CD | | neg.(−) | neg.(−) | neg.(−) | neg.(−) | neg.(−) | neg.(−) | | neg.(−) | neg.(−) |
| Anti HIV-1 Antibody (Anti p24) | | | | | | | | | | |
| Non diluted serum | | | | | | | 0.02 | 0.016 | 0.02 | 0.02 |
| Diluted-(1:50) | | 0.33 | 0.52 | 0.45 | 0.40 | 0.73 | 0.75 | 0.81 | 0.72 | 0.58 |
| Diluted-(1:2500) | | 4.77 | 3.24 | 3.46 | neg.(−) | neg.(−) | neg.(−) | 8.54 | neg.(−) | 3.78 |
| HIV-1 RNA by PCR Quant | | 4.53 | | 4.86 | | 5.33 | 4.82 | | | 5.09 |
| HIV-1 RNA by PCR Quant -number of copies | | $3.38 \times 10^4$ | | $7.18 \times 10^4$ | | $2.16 \times 10^3$ | $6.66 \times 10^4$ | | | $1.23 \times 10^5$ |

TABLE 24

Patient No 018
Blood analysis

| | −1 | Base | 2w | 4w | 6w | 8w | 3m | 4m | 5m | 6m |
|---|---|---|---|---|---|---|---|---|---|---|
| INJECTION | | 0 | 4 | 8 | 12 | 16 | — | — | — | |
| Red blood cells count | | 4.10 | 3.8 | 4.1 | 4.2 | 4.3 | 4.1 | 3.67 | 3.6 | |
| Hemoglobin | | 142 | 138 | 140 | 142 | 140 | 138 | 134 | 136 | |
| Total WBC count | | 3.4 | 5.4 | 5.1 | 3.9 | 3.7 | 4.5 | 4.3 | 4.0 | |
| Total St(% of WBC) | | 9 | 7 | 2 | 8 | 3 | 5 | 3 | 4 | |
| Total Seg (% of WBC) | | 46 | 54 | 52 | 54 | 51 | 62 | 57 | 53 | |
| Total Ly (% of WBC) | | 34 | 32 | 39 | 32 | 39 | 25 | 34 | 30 | |
| Total Mo (% of WBC) | | 7 | 5 | 3 | 3 | 3 | 6 | 5 | 3 | |
| Total Ba (% of WBC) | | — | — | — | — | — | — | — | — | |
| Total Eo (% of WBC) | | 4 | 2 | 4 | 3 | 4 | 2 | 1 | — | |
| Platelet Count | | 150 | 166 | 161 | 164 | 158 | 167 | 192 | 194 | |
| ESR (Westergreen) | | 15/34 | 10/24 | 20/38 | 22/44 | 28/44 | 30/50 | 45/60 | 30/60 | |

TABLE 24-continued

Patient No 018
Blood analysis

|  | −1 | Base | 2w | 4w | 6w | 8w | 3m | 4m | 5m | 6m |
|---|---|---|---|---|---|---|---|---|---|---|
| Total protein |  | 108 | 98 | 98 | 90 | 85 | 80 | 78 | 84 |  |
| Albumin |  | 45 | 45 | 42 | 40 | 41 | 42 | 40 | 40 |  |
| ASAT (GOT) |  | 9 | 18 | 18 | 20 | 11 | 12 | 27 | 17 |  |
| ALAT (GPT) |  | 12 | 24 | 18 | 34 | 25 | 24 | 30 | 25 |  |
| Absolute CD3 |  | 2197 | 2347 | 1525 | 1887 | 2765 | 1952 | 2506 | 1722 | 1556 |
| Absolute CD4 |  | 793 | 888 | 692 | 806 | 1169 | 758 | 830 | 701 | 662 |
| Absolute CD8 |  | 1349 | 1418 | 822 | 1044 | 1508 | 1169 | 1647 | 953 | 891 |
| CD4/CD8 Ratio |  | 0.59 | 0.63 | 0.84 | 0.77 | 0.78 | 0.65 | 0.50 | 0.74 | 0.70 |
| HIV-1 Antigen (p24) CD |  | neg.(−) | neg.(−) | neg.(−) | neg.(−) |  | neg.(−) | neg.(−) | neg.(−) | neg.(−) |
| Anti HIV-1 Antibody (Anti p24) |  |  |  |  |  |  |  |  |  |  |
| Non diluted serum |  |  |  |  |  |  | 0.009 | 0.01 | 0.01 | 0.009 |
| Diluted-(1:50) |  | 0.35 | 0.11 | 0.22 | 0.16 | 0.31 | 0.26 | 0.33 | 0.31 | 0.38 |
| Diluted-(1:2500) |  | 1.94 | neg.(−) | neg.(−) | neg.(−) | neg.(−) | neg.(−) | neg.(−) | neg.(−) | neg.(−) |
| HIV-1 RNA by PCR Quant |  | 3.57 |  | 4.78 |  | 3.80 | 4.37 |  |  | 4.76 |
| HIV-1 RNA by PCR Quant -number of copies |  | $3.69 \times 10^3$ |  | $3.99 \times 10^4$ |  | $6.35 \times 10^3$ | $2.32 \times 10^4$ |  |  | $5.70 \times 10^4$ |

TABLE 25

Patient No 019
Blood analysis

|  | −1 | Base | 2w | 4w | 6w | 8w | 3m | 4m | 5m | 6m |
|---|---|---|---|---|---|---|---|---|---|---|
| INJECTION |  | 0 | 4 | 8 | 12 | 16 | — | — | — | — |
| Red blood cells count |  | 3.21 | 3.24 | 3.3 | 3.3 | 3.29 | 3.37 | 3.4 | 3.46 | 3.24 |
| Hemoglobin |  | 120 | 112 | 122 | 120 | 116 | 120 | 122 | 120 | 116 |
| Total WBC count |  | 3.7 | 3.7 | 3.6 | 4.1 | 3.8 | 4.6 | 4.0 | 3.9 | 4.7 |
| Total St(% of WBC) |  | 12 | 8 | 3 | 7 | 2 | 4 | 4 | 7 | 6 |
| Total Seg (% of WBC) |  | 64 | 61 | 65 | 57 | 55 | 66 | 59 | 60 | 70 |
| Total Ly (% of WBC) |  | 18 | 26 | 26 | 29 | 37 | 23 | 33 | 26 | 21 |
| Total Mo (% of WBC) |  | 6 | 4 | 4 | 3 | 4 | 3 | 3 | 4 | 3 |
| Total Ba (% of WBC) |  | — | — | — | — | — | — | — | — | — |
| Total Eo (% of WBC) |  | — | 1 | 2 | 4 | 2 | 4 | 1 | 3 | — |
| Platelet Count |  | 197 | 185 | 201 | 198 | 188 | 189 | 181 | 190 | 170 |
| ESR (Westergreen) |  | 18/35 | 16/26 | 20/40 | 26/44 | 20/40 | 26/41 | 10/20 | 20/34 | 20/31 |
| Total protein |  | 91 | 96 | 88 | 84 | 79 | 75 | 76 | 78 | 76 |
| Albumin |  | 40 | 42 | 41 | 41 | 40 | 45 | 40 | 43 | 40 |
| ASAT (GOT) |  | 11 | 21 | 10 | 22 | 21 | 16 | 11 | 12 | 8 |
| ALAT (GPT) |  | 20 | 25 | 12 | 30 | 20 | 20 | 9 | 23 | 12 |
| Absolute CD3 |  | 849 | 1002 | 1041 | 1064 | 1115 | 1067 | 1106 | 1009 | 932 |
| Absolute CD4 |  | 178 | 205 | 180 | 242 | 200 | 191 | 202 | 199 | 192 |
| Absolute CD8 |  | 644 | 770 | 829 | 780 | 876 | 855 | 904 | 751 | 732 |
| CD4/CD8 Ratio |  | 0.28 | 0.27 | 0.22 | 0.31 | 0.23 | 0.22 | 0.22 | 0.26 | 0.26 |
| HIV-1 Antigen (p24) CD |  | neg.(−) | neg.(−) | neg.(−) | neg.(−) | neg.(−) | neg.(−) | neg.(−) | neg.(−) | neg.(−) |
| Anti HIV-1 Antibody (Anti p24) |  |  |  |  |  |  |  |  |  |  |
| Non diluted serum |  | 0.0009 | 0.003 | 0.0014 | 0.006 | 0.002 | 0.009 | 0.002 | 0.003 | 0.007 |
| Diluted-(1:50) |  | neg.(−) | neg.(−) | neg.(−) | neg.(−) | 0.04 | 0.56 | neg.(−) | neg.(−) | 0.07 |
| Diluted-(1:2500) |  | neg.(−) | neg.(−) | neg.(−) | neg.(−) | neg.(−) | neg.(−) | neg.(−) | neg.(−) | neg.(−) |
| HIV-1 RNA by PCR Quant |  | 4.18 |  | 3.28 |  | 3.48 | 3.73 |  |  | 2.94 |
| HIV-1 RNA by PCR Quant -number of copies |  | $1.51 \times 10^4$ |  | $1.90 \times 10^3$ |  | $3.03 \times 10^3$ | $5.33 \times 10^3$ |  |  | $8.80 \times 10^2$ |

TABLE 26

Patient No 020
Blood analysis

| | -1 | Base | 2w | 4w | 6w | 8w | 3m | 4m | 5m | 6m |
|---|---|---|---|---|---|---|---|---|---|---|
| INJECTION | | 0 | 4 | 8 | 12 | 16 | — | — | — | — |
| Red blood cells count | | 3.39 | 3.77 | 3.8 | 3.8 | 4.04 | 3.9 | 3.94 | 3.5 | 3.49 |
| Hemoglobin | | 128 | 136 | 134 | 132 | 138 | 136 | 136 | 136 | 136 |
| Total WBC count | | 3.8 | 4.6 | 5.6 | 4.0 | 4.7 | 4.0 | 7.0 | 5.8 | 6.0 |
| Total St(% of WBC) | | 5 | 6 | 9 | 4 | 7 | 7 | 5 | 7 | 7 |
| Total Seg (% of WBC) | | 51 | 62 | 63 | 54 | 54 | 52 | 44 | 63 | 58 |
| Total Ly (% of WBC) | | 29 | 27 | 22 | 37 | 35 | 30 | 39 | 25 | 27 |
| Total Mo (% of WBC) | | 8 | 5 | 3 | 3 | 4 | 3 | 7 | 4 | 5 |
| Total Ba (% of WBC) | | — | — | — | — | — | — | — | — | — |
| Total Eo (% of WBC) | | 7 | — | 3 | 2 | — | 8 | 5 | 1 | 3 |
| Platelet Count | | 144 | 151 | 150 | 140 | 157 | 142 | 158 | 163 | 189 |
| ESR (Westergreen) | | 8/17 | 5/16 | 16/30 | 12/26 | 18/30 | 12/24 | 20/32 | 5/10 | 10/26 |
| Total protein | | 91 | 89 | 85 | 78 | 93 | 76 | 74 | 82 | 87 |
| Albumin | | 43 | 41 | 42 | 40 | 40 | 40 | 39 | 43 | 40 |
| ASAT (GOT) | | 20 | 21 | 18 | 15 | 15 | 20 | 22 | | 17 |
| ALAT (GPT) | | 21 | 21 | 20 | 17 | 17 | 29 | 25 | 20 | 10 |
| Absolute CD3 | | 861 | 1240 | 809 | 801 | 792 | 1054 | 866 | 868 | 941 |
| Absolute CD4 | | 216 | 251 | 167 | 166 | 153 | 215 | 152 | 151 | 133 |
| Absolute CD8 | | 604 | 963 | 608 | 585 | 621 | 760 | 692 | 675 | 774 |
| CD4/CD8 Ratio | | 0.30 | 0.26 | 0.27 | 0.28 | 0.25 | 0.28 | 0.22 | 0.22 | 0.17 |
| HIV-1 Antigen (p24) CD | | pos.(+) 10 pg/ml | pos.(+) 12.5 pg/ml | pos.(+) 25 pg/ml | pos.(+) 30 pg/ml | pos.(+) 48 pg/ml | pos.(+) 10 pg/ml | pos.(+) 200 pg/ml | pos.(+) 148.2 pg/ml | pos.(+) 175.6 pg/ml |
| Anti HIV-1 Antibody (Anti p24) | | | | | | | | | | |
| Non diluted serum | | neg.(−) | neg.(−) | neg.(−) | neg.(−) | 0.0008 | 0.0001 | 0.0003 | 0.002 | 0.001 |
| Diluted-(1:50) | | neg.(−) | neg.(−) | neg.(−) | neg.(−) | neg.(−) | 0.006 | 0.03 | 0.08 | neg.(−) |
| Diluted-(1:2500) | | | neg.(−) | | neg.(−) | neg.(−) | 0.32 | 0.45 | 2.11 | neg.(−) |
| HIV-1 RNA by PCR Quant | | 4.75 | | 5.00 | | 5.35 | 5.33 | | | 5.07 |
| HIV-1 RNA by PCR Quant -number of copies | | $5.65 \times 10^4$ | | $1.01 \times 10^3$ | | $2.23 \times 10^5$ | $2.15 \times 10^5$ | | | $1.17 \times 10^5$ |

TABLE 27

Patient No 021
Blood analysis

| | -1 | Base | 2w | 4w | 6w | 8w | 3m | 4m | 5m | 6m |
|---|---|---|---|---|---|---|---|---|---|---|
| INJECTION | | 0 | 4 | 8 | 12 | 16 | — | — | — | — |
| Red blood cells count | | 3.21 | 3.4 | 3.5 | 3.31 | 3.71 | 3.31 | 4.02 | 3.29 | |
| Hemoglobin | | 104 | 114 | 120 | 119 | 107 | 122 | 130 | 124 | |
| Total WBC count | | 3.9 | 4.2 | 4.2 | 2.9 | 3.9 | 7.4 | 5.6 | 4.3 | |
| Total St(% of WBC) | | 6 | 7 | 4 | 2 | 4 | 6 | 1 | 4 | |
| Total Seg (% of WBC) | | 68 | 52 | 63 | 52 | 62 | 63 | 53 | 56 | |
| Total Ly (% of WBC) | | 22 | 34 | 21 | 39 | 26 | 27 | 35 | 32 | |
| Total Mo (% of WBC) | | 4 | 3 | 4 | 5 | 3 | 4 | 9 | 4 | |
| Total Ba (% of WBC) | | — | — | — | — | — | — | — | — | |
| Total Eo (% of WBC) | | — | 4 | 8 | 2 | 5 | — | 2 | 2 | |
| Platelet Count | | 170 | 174 | 180 | 177 | 186 | 178 | 184 | 167 | |
| ESR (Westergreen) | | 8/16 | 18/30 | 14/24 | 16/29 | 16/24 | 4/12 | 4/8 | 4/8 | |
| Total protein | | 82 | 80 | 78 | 88 | 82 | 86 | 87 | 89 | |
| Albumin | | 43 | 39 | 40 | 42 | 42 | 43 | 43 | 43 | |
| ASAT (GOT) | | 58 | 37 | 26 | 20 | 4 | 13 | 14 | | |
| ALAT (GPT) | | 70 | 45 | 38 | 19 | 9 | 9 | 10 | 39 | |
| Absolute CD3 | | 2228 | 1525 | 1733 | 2280 | 2068 | 1808 | 1999 | 1903 | 2194 |
| Absolute CD4 | 608 | 798 | 515 | 658 | 761 | 741 | 644 | 721 | 696 | 806 |
| Absolute CD8 | 1245 | 1533 | 1081 | 1148 | 1667 | 1394 | 1209 | 1406 | 1257 | 1459 |
| C04/CD8 Ratio | 0.49 | 0.52 | 0.48 | 0.57 | 0.46 | 0.53 | 0.53 | 0.51 | 0.55 | 0.55 |
| HIV-1 Antigen (p24) CD | | neg.(−) | neg.(−) | neg.(−) | neg.(−) | neg.(−) | neg.(−) | neg.(−) | neg.(−) | |
| Anti HIV-1 Antibody (Anti p24) | | | | | | | | | | |
| Non diluted serum | | | | | | 0.02 | 0.03 | 0.03 | 0.02 | 0.02 |
| Diluted-(1:50) | | 1.15 | 1.08 | 1.07 | 1.09 | 1.20 | 1.10 | 1.11 | 1.16 | 1.20 |

TABLE 27-continued

Patient No 021
Blood analysis

| | −1 | Base | 2w | 4w | 6w | 8w | 3m | 4m | 5m | 6m |
|---|---|---|---|---|---|---|---|---|---|---|
| Diluted-(1:2500) | | neg.(−) | neg.(−) | neg.(−) | 2.87 | neg.(−) | neg.(−) | neg.(−) | neg.(−) | neg.(−) |
| HIV-1 RNA by PCR Quant | | 3.94 | | 4.06 | | 3.93 | 3.65 | | | 4.66 |
| HIV-1 RNA by PCR Quant -number of copies | | $8.76 \times 10^3$ | | $1.15 \times 10^4$ | | $8.48 \times 10^3$ | $4.50 \times 10^3$ | | | $4.59 \times 10^4$ |

TABLE 28

Patient No 022
Blood analysis

| | −1 | Base | 2w | 4w | 6w | 8w | 3m | 4m | 5m | 6m |
|---|---|---|---|---|---|---|---|---|---|---|
| INJECTION | | 0 | 4 | 8 | 12 | 16 | — | — | — | |
| Red blood cells count | | 3.2 | 3.4 | 3.5 | 4.31 | 4.1 | 3.29 | 3.3 | 3.3 | |
| Hemoglobin | | 126 | 130 | 130 | 128 | 120 | 130 | 132 | 128 | |
| Total WBC count | | 6.0 | 4.5 | 4.9 | 4.2 | 5.1 | 3.7 | 4.7 | 5.9 | |
| Total St(% of WBC) | | 5 | 4 | 4 | 6 | 8 | 7 | 6 | 8 | |
| Total Seg (% of WBC) | | 54 | 74 | 65 | 66 | 63 | 67 | 57 | 42 | |
| Total Ly (% of WBC) | | 34 | 20 | 24 | 24 | 25 | 22 | 33 | 36 | |
| Total Mo (% of WBC) | | 4 | 2 | 3 | 4 | 4 | 2 | 4 | 9 | |
| Total Ba (% of WBC) | | — | — | — | — | — | — | — | — | |
| Total Eo (% of WBC) | | 3 | — | 4 | — | — | — | — | 5 | |
| Platelet Count | | 194 | 198 | 190 | 173 | 169 | 180 | 184 | 188 | |
| ESR (Westergreen) | | 18/27 | 20/24 | 28/34 | 20/33 | 22/36 | 7/12 | 17/26 | 5/14 | |
| Total protein | | 91 | 80 | 77 | 86 | 78 | 68 | 84 | 89 | |
| Albumin | | 44 | 42 | 42 | 46 | 43 | 40 | 43 | 41 | |
| ASAT (GOT) | | 32 | 16 | 12 | 14 | 12 | 17 | 10 | 17 | |
| ALAT (GPT) | | 46 | 29 | 22 | 19 | 14 | 10 | 14 | 24 | |
| Absolute CD3 | | 1853 | 1630 | 1674 | 1563 | 1461 | 1501 | 1522 | 1735 | 1484 |
| Absolute CD4 | | 713 | 565 | 724 | 612 | 581 | 610 | 586 | 608 | 470 |
| Absolute CD8 | | 1093 | 1015 | 915 | 866 | 845 | 876 | 898 | 1110 | 995 |
| C04/CD8 Ratio | | 0.65 | 0.56 | 0.79 | 0.71 | 0.69 | 0.70 | 0.65 | 0.55 | 0.47 |
| HIV-1 Antigen (p24) CD | | neg.(−) | neg.(−) | neg.(−) | neg.(−) | neg.(−) | neg.(−) | neg.(−) | neg.(−) | |
| Anti HIV-1 Antibody (Anti p24) | | | | | | | | | | |
| Non diluted serum | | | | | | 0.009 | 0.01 | 0.01 | 0.01 | 0.01 |
| Diluted-(1:50) | | | | 0.21 | 0.68 | 0.51 | 0.49 | 0.51 | 0.52 | 0.48 |
| Diluted-(1:2500) | | 3.99 | 3.40 | neg.(−) | 2.82 | neg.(−) | neg.(−) | neg.(−) | neg.(−) | neg.(−) |
| HIV-1 RNA by PCR Quant | | 3.88 | | 3.95 | | 3.85 | | | | 4.33 |
| HIV-1 RNA by PCR Quant -number of copies | | $7.63 \times 10^3$ | | $9.00 \times 10^3$ | | $7.05 \times 10^3$ | | | | $2.15 \times 10^4$ |

TABLE 29

Patient No 024
Blood analysis

| | −1 | Base | 2w | 4w | 6w | 8w | 3m | 4m | 5m | 6m |
|---|---|---|---|---|---|---|---|---|---|---|
| INJECTION | | 0 | 4 | 8 | 12 | 16 | — | — | — | — |
| Red blood cells count | | 3.5 | 3.6 | 3.7 | 3.24 | 3.37 | 3.51 | 3.54 | 3.34 | |
| Hemoglobin | | 120 | 124 | 128 | 132 | 124 | 130 | 133 | 123 | |
| Total WBC count | | 7.0 | 4.8 | 3.5 | 4.0 | 6.6 | 8.5 | 6.4 | 4.5 | |
| Total St(% of WBC) | | 6 | 6 | 4 | 1 | 4 | 8 | 4 | 6 | |
| Total Seg (% of WBC) | | 52 | 54 | 57 | 51 | 64 | 68 | 60 | 64 | |
| Total Ly (% of WBC) | | 37 | 30 | 28 | 36 | 22 | 33 | 28 | 24 | |
| Total Mo (% of WBC) | | 2 | 4 | 4 | 5 | 3 | 5 | 4 | 5 | |
| Total Ba (% of WBC) | | — | — | — | — | — | — | — | — | |
| Total Eo (% of WBC) | | 3 | 6 | 7 | 7 | 7 | 6 | 4 | 1 | |
| Platelet Count | | 174 | 178 | 180 | 183 | 169 | 164 | 181 | 183 | |

TABLE 29-continued

Patient No 024
Blood analysis

| | | | | | Week/Month | | | | |
|---|---|---|---|---|---|---|---|---|---|
| | −1 | Base | 2w | 4w | 6w | 8w | 3m | 4m | 5m | 6m |
| ESR (Westergreen) | | 7/15 | 10/18 | 8/18 | 20/40 | 26/38 | 12/26 | 20/32 | 8/15 | |
| Total protein | | 103 | 93 | 88 | 80 | 91 | 86 | 81 | 89 | |
| Albumin | | 48 | 42 | 41 | 40 | 42 | 41 | 42 | 41 | |
| ASAT (GOT) | | 24 | 16 | 20 | 24 | 33 | 11 | 10 | 19 | |
| ALAT (GPT) | | 28 | 24 | 30 | 26 | 33 | 16 | 12 | 31 | |
| Absolute CD3 | | 1922 | 1412 | 1664 | 1655 | 2113 | 1607 | 1546 | 1556 | 1670 |
| Absolute CD4 | | 856 | 651 | 834 | 802 | 1025 | 808 | 763 | 707 | 774 |
| Absolute CD8 | | 977 | 708 | 794 | 792 | 1058 | 715 | 734 | 776 | 837 |
| C04/CD8 Ratio | | 0.88 | 0.92 | 1.05 | 1.01 | 0.97 | 1.13 | 1.04 | 0.91 | 0.92 |
| HIV-1 Antigen (p24) CD | | neg.(−) | neg.(−) | neg.(−) | neg.(−) | neg.(−) | neg.(−) | neg.(−) | neg.(−) | neg.(−) |
| Anti HIV-1 Antibody | | | | | | | | | | |
| (Anti p24) | | | | | | | | | | |
| Non diluted serum | | | | | | 0.02 | 0.02 | 0.02 | 0.02 | 0.02 |
| Diluted-(1:50) | | 0.38 | 0.57 | 0.36 | 1.09 | 1.06 | 1.01 | 0.92 | 0.94 | 0.86 |
| Diluted-(1:2500) | | neg.(−) | neg.(−) | 3.26 | 3.61 | 3.70 | 3.12 | neg.(−) | neg.(−) | neg.(−) |
| HIV-1 RNA by PCR Quant | | 4.40 | | 5.21 | | 4.50 | 3.90 | | | 4.78 |
| HIV-1 RNA by PCR Quant -number of copies | | $2.50 \times 10^4$ | | $1.61 \times 10^5$ | | $3.17 \times 10^4$ | $8.03 \times 10^3$ | | | $6.08 \times 10^4$ |

TABLE 30

ANTIVIRAL EFFECTS OF TNG
VIRAL GENETICS, INC./VITAL-PHE LTD.
LOG VALUES

| | | | DURING TREATMENT | | POST TREATMENT | | |
|---|---|---|---|---|---|---|---|
| | | | | | 1 month | 4 months | 9 months |
| PATIENT NO. | GROUP NO. | BASELINE PCR | 30 DAYS PCR | 60 DAYS PCR | 90 DAYS PCR | 180 DAYS PCR | 330 DAYS PCR |
| 002 | GROUP 1 | 5.68 | 5.68Δ0 | 4.42Δ1.26 | 5.81Δ + 0.13 | 5.25Δ0.43 | 4.09Δ1.59 |
| 006 | CD4 < 200 | 5.06 | 4.75Δ0.31 | 4.24Δ0.82 | 3.64Δ1.42 | 4.35Δ0.71 | 2.89Δ2.71 |
| 015 | CELLS/CMM | 4.32 | 5.16Δ + 0.84 | 5.11Δ + 0.79 | 4.79Δ + 0.47 | 5.33Δ + 1.01 | 4.02Δ0.30 |
| 019 | | 4.18 | 3.28Δ0.90 | 3.48Δ0.70 | 3.73Δ0.45 | 2.94Δ1.24 | 2.63Δ1.55 |
| PCR DETECTION | LIMIT = 500 | AV = 4.81 | 4.72Δ0.09 | 4.31Δ0.50 | 4.490Δ0.032 | 4.47Δ0.34 | 3.41 AV 1.40 |
| 008 | GROUP 2 | 5.45 | 5.07Δ0.38 | 5.36Δ0.09 | | | 3.06Δ2.39 |
| 009 | CD4 = 200-500 | 5.35 | 5.39Δ + 0.04 | 5.65Δ + 0.3 | 5.27Δ0.08 | 5.19Δ0.16 | 3.88Δ1.47 |
| 009 | CELLS/CMM | 5.35 | 5.39Δ + 0.04 | 5.65Δ + 0.3 | 5.27Δ0.08 | 5.19Δ0.16 | 3.88Δ1.47 |
| 013 | | 3.51 | 3.40Δ0.11 | 4.77Δ + 1.37 | 3.85Δ + 0.34 | 4.40Δ + 1.00 | 2.88Δ0.63 |
| 016 | | 3.23 | 3.32Δ + 0.09 | 2.89Δ0.34 | 3.13Δ0.10 | 3.68Δ + 0.45 | 2.71Δ 0.52 |
| 017 | | 4.53 | 4.86Δ + 0.33 | 5.33Δ + 0.80 | 4.82Δ + 0.29 | 5.09Δ + 0.56 | 3.66Δ 0.87 |
| 020 | | 4.75 | 5.00Δ + 0.25 | 5.35Δ + 0.60 | 5.33Δ + 0.58 | 5.07Δ + 0.32 | 4.11Δ0.64 |
| | | AV = 447 | 4.51Δ0 | 4.89Δ + 0.42 | 4.48Δ0 | 3.90Δ0.57 | 3.38 AV 1.08 |
| 003 | GROUP 3 | 3.22 | 3.88Δ + 0.66 | 3.67Δ + 0.45 | 3.62Δ + 0.40 | 3.31Δ + 0.09 | 2.91Δ0.31 |
| 005 | CD4 > 500 | 3.72 | 3.68Δ0.04 | 3.15Δ0.57 | 2.76Δ0.96 | 3.30Δ0.42 | 2.81Δ0.91 |
| 010 | CELLS/CMM | 4.12 | 5.29Δ + 1.17 | 5.15Δ + 1.03 | 3.85Δ0.27 | 3.67Δ0.45 | 2.91Δ1.21 |
| 011 | | 4.32 | 3.36Δ0.96 | 3.81Δ0.51 | | 2.61Δ1.71 | 2.51Δ1.81 |
| 012 | | 4.77 | 4.89Δ + 0.12 | 5.21Δ + 0.44 | 4.51Δ0.26 | 4.44Δ0.33 | 3.12Δ1.65 |
| 014 | | 3.71 | 3.06Δ0.65 | 2.35Δ1.36 | Negative | 2.82Δ0.89 | 2.58Δ1.13 |
| 018 | | 3.57 | 4.78Δ + 1.21 | 3.80Δ + 0.23 | 4.37Δ + 0.80 | 4.76Δ + 1.19 | 3.43Δ0.14 |
| 021 | | 3.94 | 4.06Δ + 0.12 | 3.93Δ 0 | 3.65Δ0.29 | 4.66Δ + 0.72 | 4.03Δ0.09 |
| 022 | | 3.88 | 3.95Δ + 0.07 | 3.85Δ0 | | 4.33Δ + 0.45 | 3.06Δ0.82 |
| 024 | | 4.40 | 5.21Δ + 0.81 | 4.50Δ + 0.10 | 3.90Δ0.50 | 4.78Δ + 0.38 | 2.99Δ1.41 |
| | | AV = 3.97 | 4.22Δ + 0.25 | 3.94Δ0 | 3.80Δ0.17 | 3.86Δ0.11 | 3.04 AV 0.94 |

EXAMPLE 9

This example provides the results of a clinical study conducted with ten patients in Mexico. The ten HIV-1 infected and fulminate AIDS patients had developed resistance to multi-antiviral drug cocktail therapies. The study was approved by the Mexican Ministry of Health, and the study was carried out in accordance with Good Clinical Practices (GCPs) and Institutional Review Board review and approval. The patients were entered into this study only after they had clearly understood and signed individual Informed Consent Forms and Bill of Rights Forms. In addition, patients qualified to participate in this study met the Inclusion/Exclusion Criteria of the study protocol.

Pre-treatment and post-treatment evaluations in all patients included patient history and physical examination. blood chemistries comprising a complete blood count (CBC), and standard Chem 7. Further, blood analysis of T-lymphocyte CD 3. CD 4, and CD 8 was followed. Quantitative levels of p24 core antigen, quantitative I-IIV-1 RNA levels in plasma by PCR and quantitative HIV-1 infectious units of virus in PBMCs were also evaluated.

Each patient was injected intramuscularly with 2.0 ml of TF purified by carboxymethyl chromatography. The dose was 0.10 mg TF per kg body weight. Each patient received two injections per week, on two consecutive days, for a period of eight weeks, resulting in a total of sixteen intramuscular injections. Overall, the ten patients, who were experiencing severe weight loss before treatment, started to gain weight upon treatment with TF. No significant adverse effects were demonstrated by physical exam, subjective complaints, routine blood chemistries, or by immunologic or virologic markers, at up to twelve months post-treatment.

The following TABLE 31 summarizes the weight gain or loss of the patients at three months post TF treatment. The following TABLE 32 summarizes the results of viral load measurements by quantitative HIV-1 PCR and virus infectivity measurements of PBMCs, for the study patients.

The results of the study can be summarized as follows:

There was significant improvement in the clinical condition of all ten patients, with nine patients experiencing weight loss stabilization or substantial weight gain.

Five of the patients experienced significant improvement in their laboratory results and the remaining patients had great improvement in their laboratory results.

d) Only two patients did not show a decrease in viral load.

Most of the treated patients experienced a steady improvement in their immunological status as measured by CD 4 counts.

The patients experienced a steady increase of total lymphocyte counts, up to 30% regeneration of the immunologically competent cells.

The general condition of all patients improved; all patients expressed satisfaction with their improved clinical condition, good appetite, and lack of new symptoms of AIDS.

There were only transient superficial side effects (temporary swelling and pain at site of injection) during treatment, which completely disappeared upon the completion of the dosing phase of the study.

TF treatment of HIV infected and fulminant AIDS patients was found to be safe as determined by follow-up clinical examinations and routine blood tests.

TABLE 31

| Body Weight - Gain/Loss | | 3 Months Post - Treatment |
| --- | --- | --- |
| Weight Gain | >3 kg | 2 Patients |
| Weight Gain | 2-3 kg | 1 Patient |
| Weight Gain | 1-2 kg | 2 Patients |
| Weight Gain | 0.1-1 kg | 4 Patients |
| Weight Loss | >1 kg | 1 Patient |

TABLE 32

| Patient | CD4 Count (cells/cmm) | HIV-1 RNA* | | Infectivity of PBMCs[+] | |
| --- | --- | --- | --- | --- | --- |
| | | Baseline | 3 Months Post Treatment | Baseline | 3 Months Post Treatment |
| 001 | 304 | 2,748 | 2,215 | 1:200,000 | 1:200,000 |
| 002 | 52 | 4,166 | 40 | 1:40,000 | 1:1,000,000 |
| 003 | 137 | 10,870 | 31,106 | 1:200,000 | 1:1,000,000 |
| 004 | 86 | 3,219 | 40 | 1:40,000 | 1:1,000,000 |
| 005 | 141 | 7,027 | 40 | 1:1,600 | 1:1,000,000 |
| 006 | 30 | 40,000 | 40,000 | 1:40,000 | 1:200,000 |
| 007 | 180 | 2,113 | 40 | 1:8,000 | 1:500,000 |
| 008 | 84 | 19,230 | 40,000 | 1:40,000 | 1:40,000 |
| 009 | 154 | 1,923 | 40 | 1:1,600 | 1:200,000 |
| 010 | 167 | 9,301 | 8,312 | 1:4,000 | 1:500,000 |
| Average | — | — | — | 1:57,500 | 1:564,000 |

*Detection limit for PCR = 40
[+]Detection limit for HIV-1 in PMBCs = 1:1,000,000.

At three months post TF treatment, the viral loads of five patients, measured by quantitative PCR, showed dramatic decreases in quantitative HIV-1 viral burden to undetectable levels.

At three months post TF treatment, the viral load of all patients was measured by quantitative HIV-1 in the PBMC, with the following results:

a) No virus found in four of the patients (1:1,000,000);

b) Viral load significantly decreased to 1:500,000 in two patients;

c) Viral load greatly decreased to 1:200,000 in two patients;

EXAMPLE 10

This example reports the interaction of TF with sera from children. Fourty-five sera of children from different age groups were tested against TF, staphylococcal toxin, streptolysin, and lipopolysaccharide from Gram-negative bacteria. The samples were tested by two-dimensional gel electrophoresis similar to the method described herein.

The results showed that precipitation spurs are barely discernable in serum samples of newborns, and that precipitation spurs characteristic of sera from healthy, adult humans are attained from about one month to five years of age. The results indicate that precipitation patterns of TF with sera can be used as a measure of immune maturation, either in young children or in persons with compromised immune systems.

The present invention has been described with reference to specific embodiments. However, this application is intended to cover those changes and substitutions which may be made by those skilled in the art without departing from the spirit and scope of the appended claims

What is claimed:

1. A composition comprising a protein obtained by extraction of a lysine-rich histone fraction from non-human mammalian thymus cell nuclei by pepsin enzymatic degradation resulting in the formation of peptides having substantially reduced sizes compared to the undegraded thymus cell nuclei, said composition comprising an unmethylated protein of about 35 kilo dalton as determined by 11% non-reducing sodium dodecyl sulfate-polyacrylamide gel electrophoresis and a methylated protein of about 28 kilodalton as determined by 11% nonreducing sodium dodecyl sulfate-polyacrylamide gel electrophoresis, and having properties recited in the following (a) and (b) on a two-dimensional electrophoretic gel:
   (a) ability to precipitate a single continuous precipitation adjacent to β, α1-, α2-macro globulins from serum of a healthy human; and
   (b) inability to precipitate a single continuous precipitation adjacent to β, α1-, α2-macro globulins from serum of an AIDS patient,
the composition being useful for the treatment and diagnosis of HIV infection.

2. The composition of claim 1, wherein the composition comprises two proteins of about 12.5 and 14.5 kilodaltons as determined by 11% non-reducing sodium dodecyl sulfate-polyacrylamide gel electrophoresis.

3. The composition of claim 1, wherein the protein has an isoelectric point of about 5.6.

4. The composition of claim 3, wherein the composition has a pH of between about 7.64 and 8.6.

5. A composition of Thymus Factor ("TF") protein prepared by a method comprising the steps of:
   a) extracting and purifying a lysine-rich histone fraction by pepsin enzymatic degradation resulting in the formation of peptides having substantially reduced sizes compared to the undegraded thymus cell nuclei, and separation from non-human mammalian thymus cell nuclei;
   b) contacting the lysine-rich histone fraction with a cation exchange chromatographic material for a time sufficient for the Thymus Factor protein to bind to the cation exchange chromatographic material; and
   c) eluting an eluate comprising the Thymus Factor protein from the cation chromatographic material by contacting the chromatographic material with an aqueous salt solution,
wherein the composition comprises an unmethylated protein of about 35 kilo dalton as determined by 11% non-reducing sodium dodecyl sulfate-polyacrylamide gel electrophoresis and a methylated protein of about 28 kilodalton as determined by 11% nonreducing sodium dodecyl sulfate-polyacrylamide gel electrophoresis, and is characterized by the properties recited in the following (a) and (b) on a two-dimensional electrophoretic gel:
   (a) ability to precipitate a single continuous precipitation adjacent to β, α1-, α2-macro globulins from serum of a healthy human; and
   (b) inability to precipitate a single continuous precipitation adjacent to β, α1-, α2-macro globulins from serum of an AIDS patient.

6. The composition of claim 5, wherein the cation exchange chromatographic material is a carboxymethyl column chromatography and the carboxymethyl column is washed and the TF protein is eluted by applying a linear gradient of sodium chloride in 0.05 M sodium acetate at pH 6.8.

7. The composition of claim 5, wherein the composition of Thymus Factor protein has an isoelectric point of about 5.6 and a pH of between about 7.64 and 8.6.

8. A composition of Thymus Factor ("TF") protein prepared by a method comprising the steps of:
   a) extracting and purifying a lysine-rich histone fraction by pepsin enzymatic resulting in the formation of peptides having substantially reduced sizes compared to the undegraded thymus cell nuclei;
   b) contacting the lysine-rich histone fraction with a reverse phase high-performance liquid chromatography material for a time sufficient for the Thymus Factor protein to bind to the material; and
   c) eluting an eluate comprising the Thymus Factor protein from the high-performance liquid chromatography material by contacting the material with an acetonitrile solution,
wherein the composition comprises an unmethylated protein of about 35 kilo dalton as determined by 11% non-reducing sodium dodecyl sulfate-polyacrylamide gel electrophoresis and a methylated protein of about 28 kilodalton as determined by 11% nonreducing sodium dodecyl sulfate-polyacrylamide gel electrophoresis, and is characterized by the properties recited in the following (a) and (b) on a two-dimensional electrophoretic gel:
   (a) ability to precipitate a single continuous precipitation adjacent to β, α1-, α2-macro globulins from serum of a healthy human; and
   (b) inability to precipitate a single continuous precipitation adjacent to β, α1-, α2-macro globulins from serum of an AIDS patient.

9. The composition of claim 8, further comprising the step of collecting the eluate comprising two proteins of about 12.5 and 14.5 kilodaltons as determined by 11% nonreducing sodium dodecyl sulfate-polyacrylamide gel electrophoresis.

10. The composition of claim 9, wherein the high-performance liquid chromatography material is C-18 resin in a column, and the TF protein is eluted by applying a gradient of acetonitrile at a pH of about 6.8.

11. The composition of claim 10, wherein the TF protein interacts with HIV-1 envelope protein gp41.

12. The composition of claim 9, wherein the composition of Thymus Factor protein has an isoelectric point of about 5.6 and a pH of between about 7.64 and 8.6.

* * * * *

UNITED STATES PATENT AND TRADEMARK OFFICE
CERTIFICATE OF CORRECTION

PATENT NO. : 7,625,565 B2 Page 1 of 1
APPLICATION NO. : 10/336512
DATED : December 1, 2009
INVENTOR(S) : Zhabilov et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1016 days.

Signed and Sealed this

Second Day of November, 2010

David J. Kappos
*Director of the United States Patent and Trademark Office*